United States Patent [19]

Pyne et al.

[11] Patent Number: 4,545,810
[45] Date of Patent: Oct. 8, 1985

[54] HERBICIDAL AND PLANT GROWTH REGULANT DIPHENYLPYRIDAZINONES

[75] Inventors: William J. Pyne, Painesville; John Lowbridge, Cleveland Heights; In-Kook Chang, Painesville, all of Ohio; Florian Knotz, Graz, Austria; Larry J. Powers, Madison, Ohio

[73] Assignee: SDS Biotech Corporation, Painesville, Ohio

[21] Appl. No.: 478,689

[22] Filed: Mar. 25, 1983

Related U.S. Application Data

[60] Division of Ser. No. 288,531, Jul. 30, 1981, abandoned, which is a continuation-in-part of Ser. No. 176,082, Aug. 7, 1980, abandoned.

[51] Int. Cl.$^4$ .................. A01N 43/58; C07D 237/14
[52] U.S. Cl. .................................. 71/92; 71/65; 71/67; 71/74; 71/76; 71/78; 544/239; 544/240
[58] Field of Search ..................... 71/92; 544/239, 240

[56] References Cited

U.S. PATENT DOCUMENTS

| | | | |
|---|---|---|---|
| 2,805,926 | 9/1957 | Schoene et al. | 71/2.5 |
| 2,839,532 | 6/1958 | Druey et al. | 260/250 A |
| 3,652,562 | 3/1972 | Reicheneder et al. | 260/250 A |
| 3,709,885 | 1/1973 | Ebner et al. | 260/250 A |
| 3,870,502 | 3/1975 | Fischer | 71/92 |
| 4,013,658 | 3/1977 | Abdulla | 260/250 A |
| 4,229,205 | 10/1980 | Theobald et al. | 71/92 |
| 4,238,490 | 12/1980 | Powers et al. | 424/250 |
| 4,242,121 | 12/1980 | Hawkins et al. | 71/93 |
| 4,256,884 | 3/1981 | Hoffmann et al. | 71/92 |

OTHER PUBLICATIONS

Knotz, *Sci. Pharm.*, 41 (1973), 9–18.
Nannini et al., *Eur. J. Med. Chem.-Chimica Therapeutica*, Jan.-Feb., 1979-14, pp. 53–60.
Aydin et al., *Chim. Acta. Tur.*, 7 (1979), 121–140.
Willemot, *Plant Physiol.*, 60, (1977), 1–4.
John et al., *Plant Physiol.*, 57, (1976), 257–259.
Vaisberg et al., *Plant Physiol.*, 57, (1976), 260–269.
Elnagdi et al., *Tetrahedron*, 31, (1975), 63–67.
Ismail et al., *Revue Roumaine de Chimie*, 24, (6), (1979), 899–905.

*Primary Examiner*—Robert T. Bond
*Attorney, Agent, or Firm*—John P. Hazzard

[57] ABSTRACT

Novel compounds of the general formula

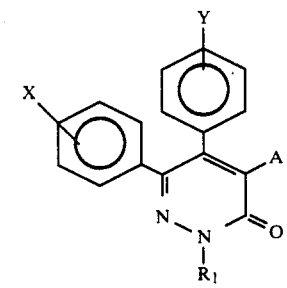

as well as novel compositions thereof and methods of using same are described. These compounds have been found to be valuable for controlling, modifying and inhibiting the growth of plants.

8 Claims, No Drawings

HERBICIDAL AND PLANT GROWTH REGULANT DIPHENYLPYRIDAZINONES

CROSS-REFERENCE TO RELATED APPLICATION

This is a division of application Ser. No. 288531 filed July 30, 1981 which application is a continuation-in-part of copending application Ser. No. 176,082 filed Aug. 7, 1980, both now abandoned.

BACKGROUND OF THE INVENTION

(1) Field of the Invention

This invention relates generally to diphenylpyridazinone derivatives which exhibit valuable herbicidal and plant growth regulant properties. This invention also relates to novel agricultural chemical compositions and methods for controlling, inhibiting and modifying the growth of a broad spectrum of plant life.

More specifically, the class of compounds of the present invention has been found to be effective both in controlling unwanted plants as well as influencing the growth and development of valuable agricultural crops and aesthetic or ornamental plants.

(2) State of the Art

A few diphenylpyridazinone derivatives which fall within the scope of this invention have been disclosed in the literature. In U.S. Pat. No. 2,839,532, June 17, 1958, 4-cyano-5,6-diphenylpyridazinone-(3) having pharmaceutical activity is disclosed. No agricultural or similar utility is disclosed. Nannini et al., *Eur. J. Med. Chem.-Chimica Therapeutica*, Jan.-Feb., 1979-14, pp. 53–60 discloses analogous diphenylpyridazinone derivatives which evidence pharmaceutical activity, specifically anti-inflammatory activity. No agricultural or similar utility is disclosed. Knotz, *Sci. Pharm.*, 41 (1973) 9–18, discloses selected N-2-substituted 5,6-diphenyl-3-oxo-4-cyano-2,3-dihydropyridazine species. The article does not disclose any agricultural or like utilities. Also, selected diphenylpyridazinones of the present invention are disclosed in application U.S. Ser. No. 11,416, filed Feb. 12, 1979, now U.S. Pat. No. 4,238,490, which compounds demonstrate pharmaceutical activity and, more particularly, are shown to be effective hypertensive agents.

U.S. Pat. Nos. 2,805,926, 3,652,562, 3,709,885, 3,870,502, 4,013,658, 4,229,205, 4,242,121 and 4,256,884 and the literature references Willemot, *Plant Physiol.*, 60 (1977) pp. 1–4, and John et al., *Plant Physiol.*, 57 (1976) pp. 257–59, disclose pyridazinone compounds having herbicidal and/or plant growth regulant utility.

SUMMARY OF THE INVENTION

It has now been discovered, in accordance with the present invention, novel diphenylpyridazinones of the general formula:

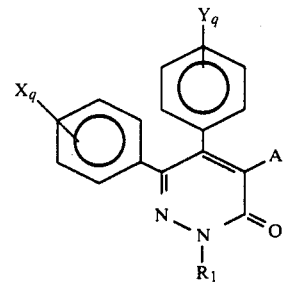

Further in accordance with the invention, active diphenylpyridazinones of the above general formula are formulated into novel compositions for selectively controlling and combating unwanted plant systems or for modifying the growth of various plant life.

Still further in accordance with the present invention, a novel method for the preparation of various acid and ester species of the diphenylpyridazinones is contemplated.

These and other aspects and advantages of the invention will be appreciated by those skilled in the art upon the reading and understanding of the specification.

DESCRIPTION OF THE PREFERRED EMBODIMENTS

A novel class of compounds has now been discovered which compounds are found to be highly active as both herbicides and plant growth regulants.

The compounds of the present invention are various substituted diphenylpyridazinones of the general formula I below

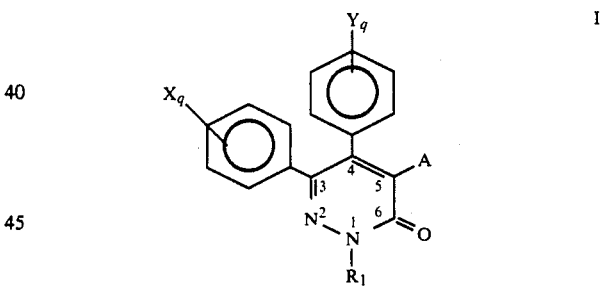

or the salts and the water hydrates thereof wherein $R_1$ is hydrogen, hydroxyalkyl, hydroxyalkoxyalkyl, alkoxyalkyl, alkylthioalkyl, alkenyloxyalkyl, alkynyloxyalkyl, alkylsulfinylalkyl, alkylsulfonylalkyl, sulfonic acidalkyl, cyanoalkyl, cyanoalkenyl, dialkylaminoalkyl, piperidinylalkyl, dimethylpyrrolidinylmethyl, phenoxyalkyl, pyrrolidinylalkyl, imidazoalkyl, haloimidazoalkyl, alkylimidazoalkyl, triazoloalkyl, halotriazoloalkyl, alkyltriazoloalkyl, tetrazoloalkyl, substitutedtetrazoloalkyl with at least one substituent selected from the group consisting of alkyl, halo, alkoxycarbonylalkyl, arylthioalkyl and alkylthioalkyl, polyoxyalkylenealkyl, $C_1$–$C_{30}$alkylpolyoxyalkylenealkyl, phenylpolyoxyalkylenealkyl, substitutedphenylpolyoxyalkylenealkyl with at least one phenyl substituent selected from the group consisting of halo and trifluoromethyl, and haloalkylpolyoxyalkylenealkyl wherein said polyoxyalkylene moiety in all cases hereinabove contains up to 50 oxyalkylene repeating units and said alkylene moiety represents 2 or 3 carbon atoms, or a member selected from the group consisting of (a) $+CH_2)_nCH=O$ where n is 1–3, inclusive;

(b)

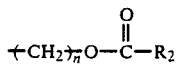

where n is 1 to 3, inclusive, and $R_2$ is alkyl, cycloalkyl, haloalkyl, carboxyalkyl, phenyl, phenyl substituted with at least one member selected from halo or alkyl;

(c)

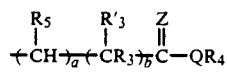

where a is 0 to 4, inclusive, b is 0 or 1, and Z and Q are the same or different and independently represent O or S; and when a is 1 to 4, $R_5$ is hydrogen, cyano or carboxy and b is 0, $R_4$ is hydrogen, $C_1-C_{30}$alkyl, allyl, alkoxyalkyl, chloro, halo($C_1-C_{30}$)alkyl, alkenyl, alkynyl, alkylthioalkyl, cycloalkyl, hydroxyalkyl, phenyl, halophenyl, alkoxyalkoxyalkyl, alkylcarboxyalkyl, phenylalkyl, alkenylcarboxyalkyl, cyanoalkyl, polyoxyalkylene, $C_1-C_{30}$alkylpolyoxyalkylene, chloropolyoxyalkylenealkyl, $C_1-C_{10}$alkylphenylpolyoxyalkylene wherein said polyoxyalkylene moiety in all cases hereinabove contains up to 50 oxyalkylene repeating units and said alkylene moiety represents 2 or 3 carbon atoms, $C_1-C_{30}$-alkylsulfonyl($C_1-C_{14}$)alkyl, $C_1-C_{30}$alkylsulfinyl($C_1-C_{14}$)alkyl, phenyl- or substitutedphenylsulfonyl($C_1-C_{14}$)alkyl with at least one phenyl substituent selected from the group consisting of halo, nitro, trifluoromethyl, methoxy, methylthio and cyano, or phenyl- or substitutedphenylsulfinyl($C_1-C_{14}$)alkyl with at least one phenyl substituent selected from the group consisting of halo, nitro, trifluoromethyl, methoxy, methylthio and cyano; or when a and b are both 0, $R_4$ is hydrogen or $C_1-C_{30}$alkyl; or when a is 1 or 2 and b is 1, $R_4$ is hydrogen, $C_1-C_{30}$alkyl or allyl, $R_3$ is alkyl, carboxy, cyanoalkyl or together with $R_5$ of the adjacent carbon atom represents a pi bond, $R'_3$ is hydrogen or alkyl, and $R_5$ is hydrogen, alkyl or together with $R_3$ represents a pi bond; or when a is 0 and b is 1, $R_4$ is hydrogen or $C_1-C_{30}$alkyl, $R'_3$ is hydrogen or alkyl and $R_3$ is alkyl, cyanoalkyl, alkanoyl or phenyl;

(d)

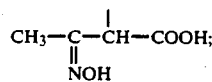

(e)

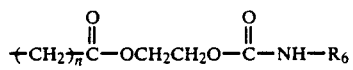

where n is 1–3 and $R_6$ is alkyl, haloalkyl, phenyl, halophenyl, alkylphenyl or trifluoromethylphenyl;

(f)

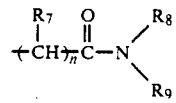

where n is 0, 1 or 2, $R_7$ is hydrogen or alkyl and $R_8$ and $R_9$ independently are hydrogen, alkyl, hydroxyalkyl, alkoxycarbonylalkyl, alkoxyalkyl, carboxyalkyl or carboxyalkylaminocarbonylalkyl;

(g)

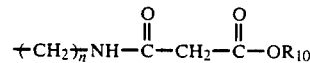

where n is 1–3 and $R_{10}$ is alkyl;

(h)

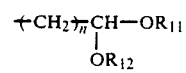

where n is 1–3 and $R_{11}$ and $R_{12}$ independently represent alkyl;

(i)

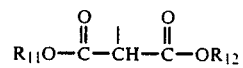

where $R_{11}$ and $R_{12}$ are the same as defined above;

(j)

where n is 1–3, inclusive; and where $R_{13}$ is hydrogen or alkyl; $R_{14}$ is hydrogen, alkoxycarbonyl, alkoxycarbonylalkylamido, amido, carboxy, polyoxyalkylenecarbonyl, $C_1-C_{30}$alkylpolyoxyalkylenecarbonyl, alkoxyalkylpolyoxyalkylenecarbonyl, $C_1-C_{10}$alkylphenylpolyoxyalkylenecarbonyl wherein said polyoxyalkylene moiety in all cases hereinabove contains up to 50 oxyalkylene repeating units and saidh alkylene moiety represents 2 or 3 carbon atoms, amidoalkyl, alkyl, imidazoalkyl, hydroxyalkyl, alkylthioalkyl, amidoalkylcarbonylalkyl, alkylcarbonylalkyl, hydroxyalkylcarbonylalkyl, N-carboxymethyleneN-amidomethylmethyleneamidoalkyl; and $R_{15}$ is alkoxycarbonyl, carboxy, carboxyalkylamidoalkylamido, 2-carboxypyrrolidinylN-carbonyl, hydroxyalkyl, alkyl, amidoalkyl, phenylalkyl, hydroxyphenylalkyl, phenylalkoxycarbonylaminoalkyl, carboxyalkyl, carboxyalkylamido, alkoxycarbonylalkylamido, 2-carboxy4-hydroxypyrrolidinylN-carbonyl, 2-carboxy3-hydroxypyrrolidinylN-carbonyl, 2-carboxy4-methylpyrrolidinylN-carbonyl, 2-carboxy4-methylenepyrrolidinylN-carbonyl, 2-carboxypiperidinylN-carbonyl, 2-carboxy5-hydroxypiperidinylN-carbonyl, 2-carboxy4-hydroxypiperidinylN-carbonyl, amino, alkylamino, acylamino, phenylamino, aminoalkylcarbonylamino, aminoalkylcarbonylaminoalkylcarbonylamino, or is a member selected from the group consisting of:

(i) $+CR_{16}R_{17})_xCONR_{18}R_{19}$ where x is 1 or 2, $R_{16}$ and $R_{17}$ are both hydrogen or together represent $=CH_2$ or $=CHCH_3$, $R_{18}$ is hydrogen or alkyl and $R_{19}$ is hydrogen, alkyl, hydroxyalkyl, phenyl, p-hydroxyphenyl or p-methoxyphenyl and (ii)

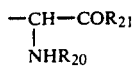

where $R_{20}$ is hydrogen, alkyl, acyl, phenyl, aminoalkylcarbonyl or aminoalkylcarbonylaminoalkylcarbonyl and $R_{21}$ is hydroxyalkyl, alkyl, amidoalkyl or N-carboxymethyleneN-amidomethylmethyleneamino;

(k) $-(CH_2)_n SO_2 R_{22}$ where n is 1 or 2 and $R_{22}$ is alkyl;

(l)

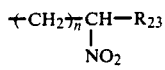

where n is 1-3 and $R_{23}$ is alkyl;

(m)

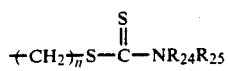

where n is 1-3 and $R_{24}$ and $R_{25}$ independently represent hydrogen and alkyl;

(n)

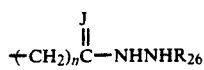

where n is 1-3, inclusive, J is O or S and $R_{26}$ is hydrogen, phenyl, trifluoromethylphenyl, halophenyl, alkyl or is the group

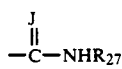

where J is the same as previously defined and $R_{27}$ is hydrogen, alkyl, phenyl, trifluoromethylphenyl or halophenyl;

(o)

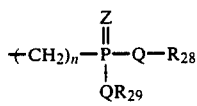

where n is 1-5, inclusive, Z and Q are the same or different and independently represent O or S and $R_{28}$ and $R_{29}$ are the same or different and independently represent hydrogen or $C_1$-$C_{30}$-alkyl;

(p)

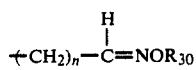

where n is 1-5, inclusive, and $R_{30}$ is hydrogen, alkylaminocarbonyl, $C_1$-$C_{30}$alkylcarbonyl, $C_1$-$C_{30}$-alkylthionyl, phenylaminocarbonyl or substitutedphenylaminocarbonyl with at least one phenyl substituent selected from the group consisting of halo, methoxy, methylthio, nitro and trifluoromethyl;

(q)

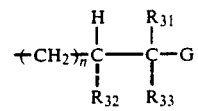

where n is 1-5, inclusive, $R_{31}$ is hydrogen or alkyl, and $R_{32}$ and $R_{33}$ together represent a pi bond or $R_{32}$ is halo, trichloromethyl, trichloromethylthio, $C_1$-$C_{30}$alkylthio, $C_1$-$C_{30}$alkylsulfonyl, phenyl- or substitutedphenylthio with at least one phenyl substituent selected from the group consisting of halo, methoxy and methylthio, phenyl- or substitutedphenylsulfinyl with at least one phenyl substituent selected from the group consisting of halo, methoxy and methylthio, $R_{33}$ is hydrogen or halo and G is $-NO_2$ or $NHR_{34}$ where $R_{34}$ is hydrogen; alkyl; alkylaminocarbonyl; phenyl- or substitutedphenylaminocarbonyl with at least one phenyl substituent selected from the group consisting of halo, methoxy, methylthio, nitro and trifluoromethyl; methylsulfonyl; chloroacetyl; dichloroacetyl; trichloroacetyl; pyrrolydinylN-carbonyl; morpholinoN-carbonyl; N-methylpiperazinylN-carbonyl; hydrazinocarbonyl; hydrazinothionyl; dialkylhydrazinocarbonyl; dialkylhydrazinothionyl; or phenyl- or substitutedphenylsulfonyl with at least one phenyl substituent selected from the group consisting of halo, methoxy, methylthio, trifluoromethyl and nitro;

(r) $-(CH_2)_m(O-(CH_2)_a)_b T$ where n is 0-5, inclusive, a is 1-3, inclusive, b is 1-50, inclusive, and T is $C_1$-$C_{30}$alkylcarbonyl; chloroacetyl; dichloroacetyl; $C_1$-$C_{30}$alkoxycarbonyl; $C_1$-$C_{30}$alkylaminocarbonyl; phenyl- or substitutedphenylaminocarbonyl with at least one phenyl substituent selected from the group consisting of halo, methoxy, methylthio, trifluoromethyl and nitro; halo; cyano; thiocyano; nitro; carboxy; chlorocarbonyl; amido; dimethylamido; $C_1$-$C_{30}$alkylsulfinyl; phenyl- or substitutedphenylsulfinyl with at least one phenyl substituent selected from the group consisting of halo, nitro, trifluoromethyl, methoxy, methylthio, cyano, carboxy and ethoxycarbonyl; $C_1$-$C_{30}$alkylsulfonyl; phenyl- or substituted phenylsulfonyl with at least one phenyl substituent selected from the group consisting of halo, nitro, trifluoromethyl, methoxy, methylthio, cyano, carboxy and ethoxycarbonyl; or a member selected from the group consisting of

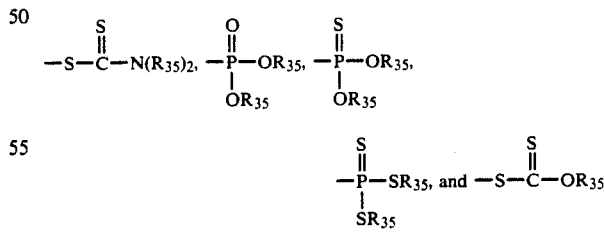

where $R_{35}$ is alkyl;

A is cyano, carboxy, trifluoromethyl, aminocarbonyl, dimethylaminocarbonyl or ethoxycarbonylmethyl, nitro, acetyl, ethoxycarbonyl, methylsulfonyl, or $NHR_{36}$ where $R_{36}$ is hydrogen, alkyl, acetyl, chloroacetyl, dichloroacetyl, trichloroacetyl, alkylaminocarbonyl, pyrrolidinylN-carbonyl, piperidinylN-carbonyl, dialkylaminoalkyl, methylsulfonyl, phenyl- or substitutedphenylsulfonyl with at least one phenyl substituent selected from the group consisting of halo, nitro, methoxy, methylthio and trifluoromethyl, or phenyl- or substitutedphenylaminocarbonyl with at least one phenyl substituent selected from the group consisting of halo, nitro, methoxy, methylthio, and trifluoromethyl;

$X_q$ and $Y_q$ are the same or different and independently represent a member selected from the group consisting of halogen, nitro, $C_1$-$C_4$alkylthio, $C_1$-$C_4$alkoxy and trifluoromethyl where q is 0, 1 or 2.

The compounds of the present invention have been found to be effective in controlling or inhibiting the growth of unwanted plants, e.g., broadleaf weeds and grasses. The present invention contemplates methods for both preemergence control and postemergence control of undesired plants by applying to the plant, the plant situs or general growth environment, a herbicidally effective amount of an active diphenylpyridazinone compound of the invention, alone or in combination with a preselected carrier or adjuvant.

The compounds of the invention, other than use for combatting undesired plants, may be used to effect the growth of a desired plant. As used herein, the expression "plant growth regulant" or "plant regulator" is defined as a substance which accelerates, retards, or otherwise alters the natural growth, development or maturation of plants. Such observable plant growth regulant effects include, for example, yield enhancement, root or top growth stimulation or inhibition, tolerance to temperature extremes, nonphytotoxic herbicide-like responses and the like. The compounds of the present invention have been found to be effective for regulating or modifying the growth of a wide variety of plant life including, ornamental plants, turf grasses, cotton, soybeans and tobacco. These effects range from yield enhancement of a variety of plants including soybeans, cotton and potatoes to control of the tobacco sucker. The nonphytotoxic effects, as will be recognized by those skilled in the art, are dependent on a variety of factors other than the specific compound employed. Thus, in general, to obtain the desired plant growth regulant effect, such factors as plant species, the stage of growth of the plant, soil conditions, mode of application, formulation of the regulator composition as well as weather conditions and the like must be considered. In general, the herbicidally-active compound of the present invention will be applied in an amount sufficient to be phytotoxic to the unwanted plant species whereas less than herbicidal amounts will be applied to promote nonphytotoxic plant growth regulant responses.

Therefore, for herbicidal applications, the herbicidally-active diphenylpyridazinones of this invention generally will be applied at between about 0.03 kg/hectare to about 8.00 kg/hectare; preferably, 0.25 kg/hectare to 4.00 kg/hectare and, most preferably, 0.5 kg/hectare to 2.00 kg/hectare. The desired plant growth regulant effects are obtained at application rates of between about 0.01 kg/hectare to 8.00 kg/hectare, preferably, 0.125 kg/hectare to 2.00 kg/hectare and, most preferably, 0.25 kg/hectare to 2.00 kg/hectare.

Exemplary of preferred compounds for use in the compositions and methods of the present invention are compounds of the above general formula I wherein $R_1$ is hydrogen, hydroxyalkyl, hydroxyalkoxyalkyl, alkoxyalkyl, alkylthioalkyl, alkenyloxyalkyl, alkynyloxyalkyl, alkylsulfinylalkyl, alkylsulfonylalkyl, cyanoalkyl, cyanoalkenyl, piperidinylalkyl, dimethylpyrrolidinylmethyl, phenoxyalkyl, pyrrolidinylalkyl, or a member selected from the group consisting of (a) $+CH_2\!\!\frac{}{n}CH=O$ where n is 1 or 2;

(b)

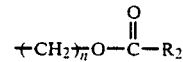

where n is 1 to 3, inclusive, and $R_2$ is alkyl, haloalkyl, carboxyalkyl, phenyl, phenyl substituted with at least one member selected from halo or alkyl;

(c)

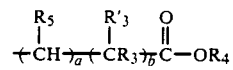

where a is 0 to 4, inclusive, and b is 0 or 1; and when a is 1 or 2 and b is 0, $R_4$ is hydrogen, $C_1$-$C_{30}$alkyl, allyl, alkoxyalkyl, chloro, halo($C_1$-$C_{30}$)alkyl, alkenyl, alkynyl, alkylthioalkyl, cycloalkyl, hydroxyalkyl, phenyl, halophenyl, alkoxyalkoxyalkyl, alkylcarboxyalkyl, phenylalkyl, alkenylcarboxyalkyl, cyanoalkyl, polyoxyalkylene, $C_1$-$C_{30}$alkylpolyoxyalkylene or $C_1$-$C_{10}$alkylphenylpolyoxyalkylene wherein said polyoxyalkylene moiety in all cases hereinabove contain up to 50 oxyalkylene repeating units and said alkylene moiety represents 2 or 3 carbon atoms, and $R_5$ is hydrogen or cyano; or when a and b are both 0, $R_4$ is hydrogen or alkyl; or when a is 3 or 4, and b is 0, $R_4$ is hydrogen or $C_1$-$C_{30}$alkyl and $R_5$ is hydrogen; or when a is 1 or 2 and b is 1, $R_4$ is hydrogen, $C_1$-$C_{30}$alkyl or allyl, $R'_3$ is hydrogen or alkyl, $R_3$ is alkyl or together with $R_5$ of the adjacent carbon atom represents a pi bond and $R_5$ is hydrogen, alkyl or together with $R_3$ represents a pi bond; or when a is 0 and b is 1, $R_4$ is hydrogen or $C_1$-$C_{30}$alkyl, $R'_3$ is hydrogen or alkyl and $R_3$ is alkyl, alkanoyl or phenyl;

(d)

$$CH_3-\underset{\underset{NOH}{\|}}{C}-CH-COOH;$$

(e)

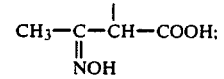

where n is 1–3 and $R_6$ is alkyl, haloalkyl, phenyl, halophenyl, alkylphenyl or trifluoromethylphenyl;

(f)

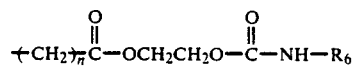

where n is 0, 1 or 2, $R_7$ is hydrogen and alkyl and $R_8$ and $R_9$ independently are hydrogen, alkyl, hydroxyalkyl, alkoxycarbonylalkyl, alkoxyalkyl, carboxyalkyl or carboxyalkylaminocarbonylalkyl;

(g)

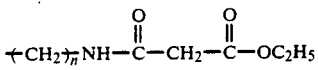

where n is 1-3;
(h)

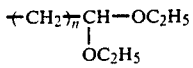

where n is 1-3;
(i)

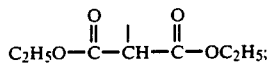

(j)

where n is 1-3 and where $R_{13}$ is hydrogen, $R_{14}$ is hydrogen, alkoxycarbonyl, alkoxycarbonylalkylamido, amido or carboxy and $R_{15}$ is alkoxycarbonyl, carboxy, carboxyalkylamidoalkylamido, 2-carboxypyrrolidinyl N-carbonyl, hydroxyalkyl, alkyl, amidoalkyl, phenylalkyl, hydroxyphenylalkyl, phenylalkoxycarbonylaminoalkyl, carboxyalkyl;

(k) —$(CH_2)_n SO_2 CH_2 CH_3$ where n is 1 or 2;

(l)

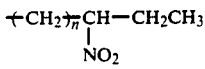

where n is 1-3;
(m)

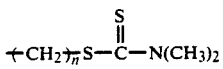

where n is 1-3;
(n)

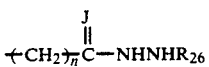

where n is 1-3, inclusive, J is O or S and $R_{26}$ is hydrogen, phenyl, trifluoromethylphenyl, halophenyl, alkyl or is the group

where J is the same as previously defined and $R_{27}$ is hydrogen, phenyl, trifluoromethylphenyl, halophenyl or alkyl;

A is cyano, carboxy, trifluoromethyl, aminocarbonyl, dimethylaminocarbonyl, ethoxycarbonylmethyl or nitro;

$X_q$ and $Y_q$ independently represent fluoro or chloro, and q is 0 or 1; subject to the provisos that when A is other than cyano, $R_1$ is said

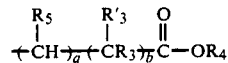

group where a is 1 or 2, b is 0, $R_5$ is hydrogen, $R_4$ is $(C_1-C_{30})$alkyl and $X_q-Y_q$ are independently fluoro if q is 1, and when A is carboxy, $R_1$ is carboxyalkyl.

As specifically preferred compounds of the aforementioned general formula for use as herbicides, there may be especially mentioned Ethanol, 2-(5-cyano-1,6-dihydro-6-oxo-3,4-diphenylpyridazin-1-yl); Acetic Acid, 5-cyano-1,6-dihydro-6-oxo-3,4-diphenylpyridazin-1-yl; Acetic Acid, 5-cyano-1,6-dihydro-6-oxo-3,4-diphenylpyridazin-1-yl ethyl ester; Propionic Acid, 3-(5-cyano-1,6-dihydro-6-oxo-3,4-diphenylpyridazin-1-yl); Propionic Acid, 3-(5-cyano-1,6-dihydro-6-oxo-3,4-diphenylpyridazin-1-yl)ethyl ester; Propionic Acid, 3-(5-cyano-1,6-dihydro-6-oxo-3,4-diphenylpyridazin-1-yl)ethoxy ethyl ester; Acetic Acid, 5-cyano-1,6-dihydro-6-oxo-3,4-diphenylpyridazin-1-yl-methoxy ethyl ester; Acetic Acid, 5-cyano-1,6-dihydro-6-oxo-3,4-diphenylpyridazin-1-yl-2-propenyl ester; Acetic Acid, 5-cyano-1,6-dihydro-6-oxo-3,4-diphenylpyridazin-1-yl-3-methoxy butyl ester; 1-Pyridazineacetylchloride, 5-cyano-1,6-dihydro-6-oxo-3,4-diphenyl; Acetic Acid, 5-cyano-1,6-dihydro-6-oxo-3,4-diphenyl pyridazin-1-yl-1-pentyl ester; Acetic Acid, 5-cyano-1,6-dihydro-6-oxo-3,4-diphenylpyridazin-1-yl-2-methyl-2-propenyl ester; Acetic Acid, 5-cyano-1,6-dihydro-6-oxo-3,4-diphenyl-pyridazin-1-yl-1-butyl ester; Acetic Acid, 5-cyano-1,6-dihydro-6-oxo-3,4-diphenylpyridazin-1-yl-2-ethyl-1-butyl ester; Acetic Acid, 5-cyano-1,6-dihydro-6-oxo-3,4-diphenylpyridazin-1-yl cyclohexyl ester; Acetic Acid, 5-cyano-1,6-dihydro-6-oxo-3,4-diphenylpyridazin-1-yl-3-methyl-3-butenyl ester; Acetic Acid, 5-cyano-1,6-dihydro-6-oxo-3,4-diphenylpyridazin-1-yl diethanol amine salt; Propionic Acid, 3-(5-cyano-1,6-dihydro-6-oxo-3,4-diphenylpyridazin-1-yl)potassium salt; Ethanol, 2-(5-cyano-1,6-dihydro-6-oxo-3,4-diphenylpyridazin-1-yl)phenylether; Acetic Acid, 5-cyano-1,6-dihydro-6-oxo-3,4-diphenylpyridazin-1-yl-2-propynyl ester; and Acetic Acid, 5-cyano-1,6-dihydro-6-oxo-3,4-diphenyl-pyridazin-1-yl-1-hexadecyl ester.

As representative preferred plant growth regulant compounds of this invention, there may be mentioned Acetic Acid, 5-cyano-1,6-dihydro-6-oxo-3,4-diphenylpyridazin-1-yl; Acetic Acid, 5-cyano-1,6-dihydro-6-oxo-3,4-diphenylpyridazin-1-yl ethyl ester; Propionic Acid, 3-(5-cyano-1,6-dihydro-6-oxo-3,4-diphenylpyridazin-1-yl); Propionic Acid, 3-(5-cyano-1,6-dihydro-6-oxo-3,4-diphenylpyridazin-1-yl)ethyl ester; Propionic Acid, 3-(5-cyano-1,6-dihydro-6-oxo-3,4-diphenylpyridazin-1-yl)-1-propyl ester; Propionic Acid, 3(5-cyano-1,6-dihydro-6-oxo-3,4-diphenylpyridazin-1-yl)diethanol amine salt; Acetic Acid, 5-cyano-1,6-dihydro-6-oxo-3,4-diphenylpyridazin-1-yl diethanol amine salt; Propionic Acid, 3-(5-cyano-1,6-dihydro-6-oxo-3,4-diphenylpyridazin-1-yl)methoxy ethyl ester; Propionic Acid, 3-(5-cyano-1,6-dihydro-6-oxo-3,4-diphenylpyridazin-1-yl)sodium salt; Acetic Acid, 5-cyano-1,6-dihydro-6-oxo-3,4-diphenylpyridazin-1-yl sodium salt; Propionic Acid, 3-(5-cyano-1,6-dihydro-6-oxo-3,4-diphenylpyridazin-1-yl)potassium salt; Acetic Acid, 5-cyano-1,6-dihydro-6-oxo-3,4-diphenylpyridazin-1-yl potassium salt; Propionic Acid, 3-(5-cyano-1,6-dihydro-6-oxo-3,4-diparafluorophenylpyridazin-1-yl)ethyl ester; Acetic Acid, 5-cyano-1,6-dihydro-6-oxo-3,4-diphenylpyridazin-1-yl methyl ester; Acetic Acid, 5-cyano-1,6-dihydro-6-oxo-3,4-diphenylpyridazin-1-yl isobutyl ester; Acetic Acid, 5-cyano-1,6-dihydro-6-oxo-3,4-diphenylpyridazin-1-yl n-propyl ester; Acetic Acid, 5-cyano-1,6-dihydro-6-oxo-3,4-diphenylpyridazin-1-yl-methoxy ethyl ester; Acetic Acid, 5-cyano-1,6-dihydro-6-oxo-3,4-diphenylpyridazin-1-yl-2-propenyl ester; Acetic Acid, 5-cyano-1,6-dihydro-6-oxo-3,4-diphenylpyridazin-1-yl-3-methoxy-1-butyl ester; Acetic Acid, 5-cyano-1,6-dihydro-6-oxo-3,4-diphenylpyridazin-1-yl-methoxymethyleneoxy ethyl ester; Acetic Acid, 5-cyano-1,6-dihydro-6-oxo-3,4-diphenylpyridazin-1-yl-1-pentyl ester; Acetic acid, 5-cyano-1,6-dihydro-6-oxo-3,4-diphenylpyridazin-1-yl-1-butyl ester; Acetic Acid, 5-cyano-1,6-dihydro-6-oxo-3,4-diphenylpyridazin-1-yl-1-hexadecyl ester; Acetic Acid, 5-cyano-1,6-dihydro-6-oxo-3,4-diphenylpyridazin-1-yl-1-hexyl ester; Acetic Acid, 5-cyano-1,6-dihydro-6-oxo-3,4-diphenylpyridazin-1-yl-4-chloro-1-butyl ester; Acetic Acid, 5-cyano-1,6-dihydro-6-oxo-3,4-diphenylpyridazin-1-yl-ethoxy ethyl ester; and Acetic Acid, 5-cyano-1,6-dihydro-6-oxo-3,4-diphenylpyridazin-1-yl-phenoxy ethyl ester.

As previously indicated, specific diphenylpyridazinone compounds set forth hereinabove in formula (I) usable in accordance with the practice of the present invention have heretofore been described (Knotz, Sci. Pharm., 41 (1973) pp. 9-18 and Druey et al, U.S. Pat. No. 2,839,532), however, the following compound species of the general formula (I) (see above) are novel herbicidal and plant growth regulant active compounds wherein $R_1$ is hydroxyalkoxyalkyl, alkoxyalkyl, alkylthioalkyl, alkenyloxyalkyl, alkynyloxyalkyl, alkylsulfinylalkyl, alkylsulfonylalkyl, sulfonic acidalkyl, cyanoalkyl, cyanoalkenyl, dimethylpyrrolidinylmethyl, phenoxyalkyl, pyrrolidinylalkyl, imidazoalkyl, haloimidazoalkyl, alkylimidazoalkyl, triazoloalkyl, halotriazoloalkyl, alkyltriazoloalkyl, tetrazoloalkyl, substitutedtetrazoloalkyl with at least one substituent selected from the group consisting of alkyl, halo, alkoxycarbonylalkyl, arylthioalkyl and alkylthioalkyl, polyoxyalkylenealkyl, $C_1$-$C_{30}$alkylpolyoxyalkylenealkyl, phenylpolyoxyalkylenealkyl, substitutedphenylpolyoxyalkylenealkyl with at least one phenyl substituent selected from the group consisting of halo and trifluoromethyl, and haloalkylpolyoxyalkylenealkyl wherein said polyoxyalkylene moiety in all cases hereinabove contains up to 50 oxyalkylene repeating units and said alkylene moiety represents 2 or 3 carbon atoms, or a member selected from the group consisting of (a) —$(CH_2)_n$CH=O wherein n is 1-3, inclusive;

(b)

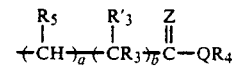

where n is 1 to 3, inclusive, and $R_2$ is alkyl, cycloalkyl, haloalkyl, carboxyalkyl, phenyl, phenyl substituted with at least one member selected from halo or alkyl, with the proviso that when n is 2, $R_2$ is other than carboxyalkyl;

(c)

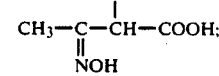

where a is 0 to 4, inclusive, b is 0 or 1, and Z and Q are the same or different and independently represent O or S; and when a is 1 to 4, $R_5$ is hydrogen, cyano or carboxy and b is 0, $R_4$ is hydrogen, $C_1$-$C_{30}$alkyl, allyl, alkoxyalkyl, chloro, halo($C_1$-$C_{30}$)alkyl, alkenyl, alkynyl, alkylthioalkyl, cycloalkyl, hydroxyalkyl, phenyl, halophenyl, alkoxyalkoxyalkyl, alkylcarboxyalkyl, phenylalkyl, alkenylcarboxyalkyl, cyanoalkyl, polyoxyalkylene, $C_1$-$C_{30}$alkylpolyoxyalkylene, chloropolyoxyalkylenealkyl, $C_1$-$C_{10}$alkylphenylpolyoxyalkylene wherein said polyoxyalkylene moiety in all cases hereinabove contains up to 50 oxyalkylene repeating units and said alkylene moiety represents 2 or 3 carbon atoms, $C_1$-$C_{30}$alkylsulfonyl($C_1$-$C_{14}$)alkyl, $C_1$-$C_{30}$alkylsulfinyl($C_1$-$C_{14}$)alkyl, phenyl- or substitutedphenylsulfonyl($C_1$-$C_{14}$)alkyl with at least one phenyl substituent selected from the group consisting of halo, nitro, trifluoromethyl, methoxy, methylthio and cyano, or phenyl- or substitutedphenylsulfinyl($C_1$-$C_{14}$)alkyl with at least one phenyl substituent selected from the group consisting of halo, nitro, trifluoromethyl, methoxy, methylthio and cyano; or when a and b are both 0, $R_4$ is hydrogen or $C_1$-$C_{30}$alkyl; or when a is 1 or 2 and b is 1, $R_4$ is hydrogen, $C_1$-$C_{30}$alkyl or allyl, $R_3$ is alkyl, carboxy, cyanoalkyl or together with $R_5$ of the adjacent carbon atom represents a pi bond, $R'_3$ is hydrogen or alkyl, and $R_5$ is hydrogen, alkyl or together with $R_3$ represents a pi bond; or when a is 0 and b is 1, $R_4$ is hydrogen or $C_1$—$C_{30}$ alkyl, $R'_3$ is hydrogen or alkyl and $R_3$ is alkyl, cyanoalkyl, alkanoyl or phenyl, subject to the provisos that when a is 1, b is 0, Z and Q are both O and A is cyano, $R_4$ is other than ethyl and when Z and Q are both O, a is 1 to 4, b is 0 or 1, $R_5$ is hydrogen, $R_3$ is alkyl with b=1, $R'_3$ is hydrogen or alkyl with b=1, A is cyano and $X_q$ and $Y_q$ are halo with q being at least 1, $R_4$ is other than hydrogen;

(d)

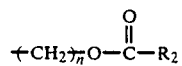

(e)

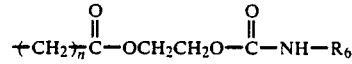

where n is 1-3 and $R_6$ is alkyl, haloalkyl, phenyl, halophenyl, alkylphenyl or trifluoromethylphenyl;

(f)

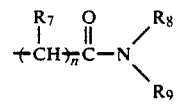

where n is 0, 1 or 2, $R_7$ is hydrogen or alkyl and $R_8$ and $R_9$ independently are hydrogen, alkyl, hydroxyalkyl, alkoxycarbonylalkyl, alkoxyalkyl, carboxyalkyl or carboxyalkylaminocarbonylalkyl;

(g)

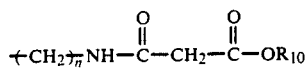

where n is 1-3 and $R_{10}$ is alkyl;

(h)

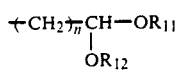

where n is 1-3 and $R_{11}$ and $R_{12}$ independently represent alkyl;

(i)

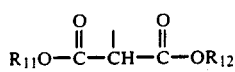

where $R_{11}$ and $R_{12}$ are the same as defined above;

(j)

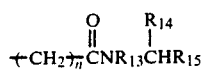

where n is 1-3, inclusive; and where $R_{13}$ is hydrogen or alkyl; $R_{14}$ is hydrogen, alkoxycarbonyl, alkoxycarbonylalkylamido, amido, carboxy, polyoxyalkylenecarbonyl, $C_1-C_{30}$alkylpolyoxyalkylenecarbonyl, alkoxyalkylpolyoxyalkylenecarbonyl, $C_1-C_{10}$alkylphenylpolyoxyalkylenecarbonyl wherein said polyoxyalkylene moiety in all cases hereinabove contains up to 50 oxyalkylene repeating units and said alkylene moiety represents 2 or 3 carbon atoms, amidoalkyl, alkyl, imidazoalkyl, hydroxyalkyl, alkylthioalkyl, amidoalkylcarbonylalkyl, alkylcarbonylalkyl, hydroxyalkylcarbonylalkyl, N-carboxymethyleneN-amidomethylmethyleneamidoalkyl; and $R_{15}$ is alkoxycarbonyl, carboxy, carboxyalkylamidoalkylamido, 2-carboxypyrrolidinylN-carbonyl, hydroxyalkyl, alkyl, amidoalkyl, phenylalkyl, hydroxyphenylalkyl, phenylalkoxycarbonylaminoalkyl, carboxyalkyl, carboxyalkylamido, alkoxycarbonylalkylamido, 2-carboxy4-hydroxypyrrolidinylN-carbonyl, 2-carboxy3-hydroxypyrrolidinylN-carbonyl, 2-carboxy4-methylpyrrolidinylN-carbonyl, 2-carboxy4-methylenepyrrolidinylN-carbonyl, 2-carboxypiperidinylN-carbonyl, 2-carboxy5-hydroxypiperidinylN-carbonyl, 2-carboxy4-hydroxypiperidinylN-carbonyl, amino, alkylamino, acylamino, phenylamino, aminoalkylcarbonylamino, aminoalkylcarbonylaminoalkylcarbonylamino, or is a member selected from the group consisting of:

(i) $+CR_{16}R_{17})_xCONR_{18}R_{19}$ where x is 1 or 2, $R_{16}$ and $R_{17}$ are both hydrogen or together represent $=CH_2$ or $=CHCH_3$, $R_{18}$ is hydrogen or alkyl and $R_{19}$ is hydrogen, alkyl, hydroxyalkyl, phenyl, p-hydroxyphenyl or p-methoxyphenyl and (ii)

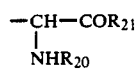

where $R_{20}$ is hydrogen, alkyl, acyl, phenyl, aminoalkylcarbonyl or aminoalkylcarbonylaminoalkylcarbonyl and $R_{21}$ is hydroxyalkyl, alkyl, amidoalkyl or N-carboxymethyleneN-amidomethylmethyleneamino;

(k) $-CH_2)_nSO_2R_{22}$ where n is 1 or 2 and $R_{22}$ is alkyl;

(l)

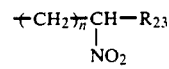

where n is 1-3 and $R_{23}$ is alkyl;

(m)

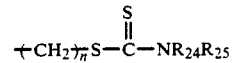

where n is 1-3 and $R_{24}$ and $R_{25}$ independently represent hydrogen and alkyl;

(n)

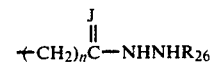

where n is 1-3, inclusive, J is O or S and $R_{26}$ is hydrogen, phenyl, trifluoromethylphenyl, halophenyl, alkyl or is the group

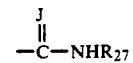

where J is the same as previously defined and $R_{27}$ is hydrogen, alkyl, phenyl, trifluoromethylphenyl or halophenyl;

(o)

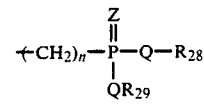

where n is 1-5, inclusive, Z and Q are the same or different and independently represent O or S and $R_{28}$ and $R_{29}$ are the same or different and independently represent hydrogen or $C_1-C_{30}$alkyl;

(p)

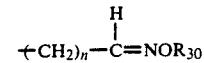

where n is 1-5, inclusive, and $R_{30}$ is hydrogen, alkylaminocarbonyl, $C_1-C_{30}$alkylcarbonyl, $C_1-C_{30}$alkylthionyl, phenylaminocarbonyl or substituted-phenylaminocarbonyl with at least one phenyl substituent selected from the group consisting of halo, methoxy, methylthio, nitro and trifluoromethyl;

(q)

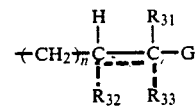

where n is 1-5, inclusive, $R_{31}$ is hydrogen or alkyl, and $R_{32}$ and $R_{33}$ together represent a pi bond or $R_{32}$ is halo, trichloromethyl, trichloromethylthio, $C_1-C_{30}$alkylthio, $C_1$-$C_{30}$alkylsulfonyl, phenyl- or substitutedphenylthio with at least one phenyl substituent selected from the group consisting of halo, methoxy and methylthio, phenyl- or substitutedphenylsulfinyl with at least one phenyl substituent selected from the group consisting of halo, methoxy and methylthio, $R_{33}$ is hydrogen or halo and G is —$NO_2$ or $NHR_{34}$ where $R_{34}$ is hydrogen; alkyl; alkylaminocarbonyl; phenyl- or substitutedphenylaminocarbonyl with at least one phenyl substituent selected from the group consisting of halo, methoxy, methylthio, nitro and trifluoromethyl; methylsulfonyl; chloroacetyl; dichloroacetyl; trichloroacetyl; pyrrolydinylN-carbonyl; morpholinoN-carbonyl; N-methylpiperazinylN-carbonyl; hydrazinocarbonyl; hydrazinothionyl; dialkylhydrazinocarbonyl; dialkylhydrazinothionyl; or phenyl- or substitutedphenylsulfonyl with at least one phenyl substituent selected from the group consisting of halo, methoxy, methylthio, trifluoromethyl and nitro;

(r) $+CH_2)_n(O+CH_2)_a)_b T$ where n is 0–5, inclusive, a is 1–3, inclusive, b is 1–50, inclusive, and T is $C_1$-$C_{30}$alkylcarbonyl; chloroacetyl; dichloroacetyl; $C_1$-$C_{30}$alkoxycarbonyl; $C_1$-$C_{30}$alkylaminocarbonyl; phenyl- or substitutedphenylaminocarbonyl with at least one phenyl substituent selected from the group consisting of halo, methoxy, methylthio, trifluoromethyl and nitro; halo; cyano; thiocyano; nitro; carboxy; chlorocarbonyl; amido; dimethylamido; $C_1$-$C_{30}$alkylsulfinyl; phenyl- or substitutedphenylsulfinyl with at least one phenyl substituent selected from the group consisting of halo, nitro, trifluoromethyl, methoxy, methylthio, cyano, carboxy and ethoxycarbonyl; $C_1$-$C_{30}$alkylsulfonyl; phenyl- or substituted phenylsulfonyl with at least one phenyl substituent selected from the group consisting of halo, nitro, trifluoromethyl, methoxy, methythio, cyano, carboxy and ethoxycarbonyl; or a member selected from the group consisting of

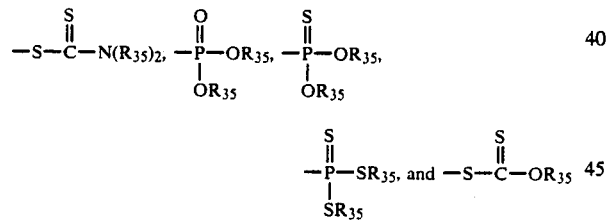

A is cyano, carboxy, trifluoromethyl, aminocarbonyl, dimethylaminocarbonyl or ethoxycarbonylmethyl, nitro, acetyl, ethoxycarbonyl, methysulfonyl, or $NHR_{36}$ where $R_{36}$ is hydrogen, alkyl, acetyl, chloroacetyl, dichloroacetyl, trichloroacetyl, alkylaminocarbonyl, pyrrolidinylN-carbonyl, piperidinylN-carbonyl, dialkyklaminoalkyl, methylsulfonyl, phenyl- or substitutedphenylsulfonyl with at least one phenyl substituent selected from the group consisting of halo, nitro, methoxy, methylthio and trifluoromethyl, or phenyl- or substitutedphenylaminocarbonyl with at least one phenyl substituent selected from the group consisting of halo, nitro, methoxy, methylthio, and trifluoromethyl;

$X_q$ and $Y_q$ are the same or different and independently represent a member selected from the group consisting of halogen, nitro, $C_1$-$C_4$alkylthio, $C_1$-$C_4$alkoxy and trifluoromethyl where q is 0, 1 or 2;

subject to provisos that when A is acetyl, $R_1$ is one of the members identified hereinabove by the designations (n), (o), (p), (q), (r), or any hereinabove identified $R_1$ member containing a polyoxyalkylene moiety and when A is nitro and Q is 0, $R_1$ is other than hydrogen.

For the purposes of this invention, the following terms, as used herein, are defined as follows: "alkyl" represents 1 to 8 carbon atoms, unless otherwise specified and includes all straight chain and branch chain moieties; "alkenyl" and "alkynyl" represent 2 to 6 carbon atoms unless otherwise specified and includes all straight chain and branch chain moieties; and the term "salts" includes alkali metal salts, alkaline earth metal salts, acid addition salts, quaternary ammonium salts and amino acid salts.

The diphenylpyridazinones of the present invention may be prepared by several alternative acceptable methods. However, all the compounds of this invention can be derived ultimately from Compound IV or Compound V below which compounds can be prepared according to the general reaction scheme set out below. The benzil (II) starting material below can be purchased commercially or prepared from the desired benzaldehyde compound by any well known or conventional technique.

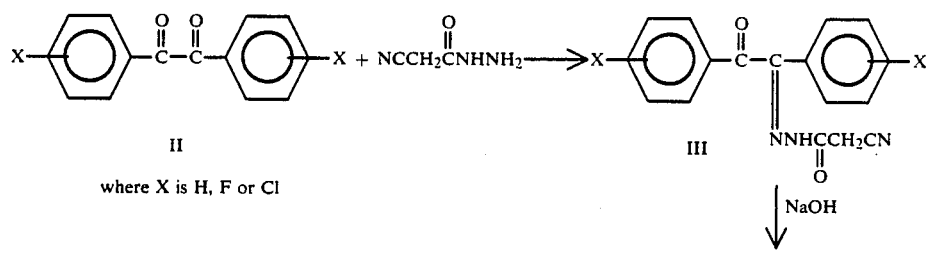

where X is H, F or Cl

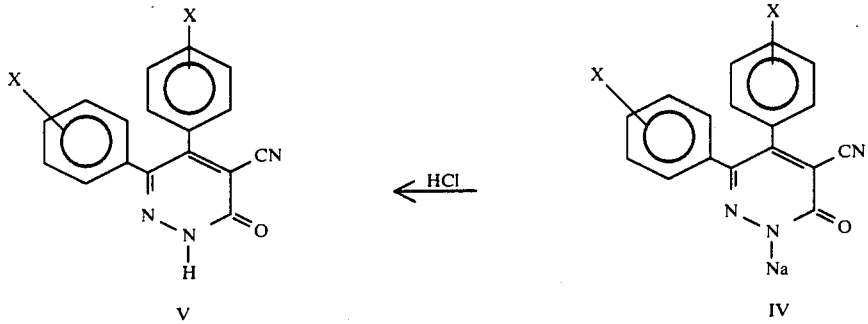

V   ←HCl   IV

Other compounds of this invention can then be derived by, for example, treating IV with a halogenated alcohol or by treating V with ethylene carbonate to obtain the hydroxyalkyl derivatives. The hydroxyalkyl derivatives can further be used to prepare, for example, the various ester derivatives by treatment with the requisite anhydride; or the various carbamate derivates can be prepared from the hydroxyalkyl derivative by treatment with the requisite isocyanate. The various ester derivatives can be further hydrolyzed to the corresponding acid derivatives or used in preparing the amino acid ester derivatives of this invention. In general, the desired diphenylpyridazinone derivative can be obtained by appropriate selection of the particular alkyl, alkoxy, alkoxycarbonyl, hydroxyalkyl, alkenyl, and the like reactant. A few of the foregoing preparative procedures are set out in Knotz, *Sci. Pharm.*, 41, (1973) pp. 9–18. The specific reactants, procedures and conditions are further to be illustrated in the examples that follow this discussion.

It has been discovered, however, in accordance with this invention a specific method for the preparation of specific ester derivatives given by formula VI below by reacting V above the appropriate α, β unsaturated acid or ester given by formula VII below:

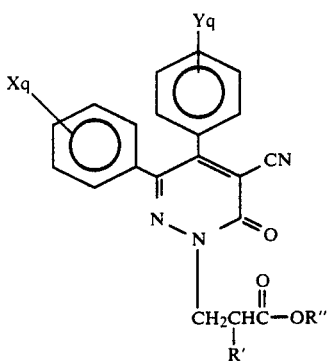   VI where R' is hydrogen or methyl, R" is hydrogen or alkyl and Xq and Yq independently represent fluoro or chloro and q is 0, 1 or 2; and

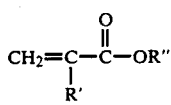   VII where R' and R" are the same as previously defined. While similar synthetic methods have been disclosed in the literature, e.g, Elnagdi et al., *Tetrahedron*, 31, (1975) pp. 63–67 and Ismail et al., *Revue Roumaine de Chemie*, 24, 899–905 (1979), the specific diphenylpyridazinone ester derivatives (formula VI) have not been heretofore prepared by this method.

The active compounds according to the instant invention may be utilized, if desired or necessary, in the form of acceptable formulations or compositions containing liquid or solid inert pesticidal carriers or adjuvants in addition to the active agent(s) to provide solutions, emulsions, suspensions, dusts, wettable powders, etc., which facilitate the use and application of the compounds of the invention to preselected substrates. The aforesaid compositions and formulations may be prepared in a known manner, for instance, by admixing the active compounds of the invention with dispersible liquid diluents and carriers optionally in combination with other vehicles, such as surface-active agents, including emulsifying agents or dispersing agents and suitable solubilizing or diluting solvents as described in the above-mentioned U.S. Pat. Nos. 3,960,542 and 4,050,921. As suitable carriers or vehicles, there may be mentioned aromatic hydrocarbons (e.g., benzene, toluene, xylene, etc.), halogenated aromatic hydrocarbons (e.g., chlorobenzenes), paraffins (e.g., petroleum fractions), chlorinated aliphatic hydrocarbons (e.g., methylene chloride, etc.), alcohols (e.g., methanol, ethanol, propanol, butanol, etc.), ethers and ether alcohols (e.g., glycol monomethyl ether, etc.), amines (e.g., ethanolamine, etc.), amides (e.g., dimethylformamide, etc.), ketones (e.g., acetone, etc.) and water as well as other conventional solvents. Moreover, solid inert carriers such as kaolins, alumina, silica, calcium carbonate, talc or kieselguhr may be employed. Appropriate nonionic and anionic emulsifying agents or surface active agents, such as polyethylene oxide esters of fatty acids and fatty alcohols, alkyl sulfonates and aryl sulfonates may be used in conjunction with the aforesaid carriers, vehicles, adjuvants and solvents.

The compositions in accordance with the present invention may also contain other compatible growth regulants, fungicides, nematocides, insecticides, fertilizers and other known herbicides. According to the accepted practices in the formulating art, when combined with other active agents or with carriers, vehicles and the like, the compositions of the invention contain from about 0.01 percent to about 99 percent, by weight, of the instant compounds as the active components thereof.

The active compounds and formulated compositions of the invention may be applied, for example, by spraying, atomizing, dusting, soil injection, seed pretreatment, etc., to obtain the desired herbicidal and plant growth regulant responses.

Various features and aspects of the present invention will be further illustrated in the examples that follow. While these examples are presented to show one skilled in the art how to operate within the scope of this invention, they are not to serve as a limitation of the scope of the invention where such scope is only defined in the claims.

COMPOUND PREPARATION

The following examples illustrate the preparation of the compounds of the present invention.

Examples 1 through 6A illustrate the reactant compound precursors from which the pyridazinone derivatives were synthesized. These compound predecessors are summarized in Table I and may be synthesized in situ or may in some cases be purchased commercially.

EXAMPLE 1

4-Cyano-5,6-diphenyl-3-(2H)-pyridazinone

Benzil 63.1 grams (0.3 mole) along with 30 grams (0.3 mole) of cyanoacetohydrazide in 200 mls of dimethylformamide was heated at 110° C: for five hours. The solution was cooled and the precipitant solid was filtered and washed with ethyl alcohol. The filtrate was vacuum distilled and the residual solid was washed with ethyl alcohol and filtered. There was isolated 74.5 grams, a 95% yield, of a solid which melted at 280°–281° C. Calculated for $C_{17}H_{11}N_3O$, C, 74.7; H, 4.1; N, 15.4. Found: C, 74.4; H, 4.16; N, 15.2. The infrared spectra showed the nitrile at 4.5μ; the

band for an amide at 6.0μ.

EXAMPLE 2

4-Carboxy-5,6-diphenyl-3-(2H)-pyridazinone 50 grams (0.183 mole) of the product of Example 1 was reacted with a mixture of 250 mls of conc. sulfuric acid and 50 mls of distilled water. This solution was heated to 150° C. for 6 hours, cooled and the mixture poured into ice. The precipitant solid was filtered, washed with water and air dried. This solid was recrystallized from absolute ethyl alcohol to give 4.0 grams (7.5%) yield of a white solid that melts at 243°–244° C. Calculated for $C_{17}H_{12}N_2O_3$ C, 68.6; H, 4.04; N, 9.5. Found: C, 69.8; H, 4.13; N, 9.59.

EXAMPLE 3

4,5-Diphenyl-3-trifluoromethyl-3-(2H)-pyridazinone

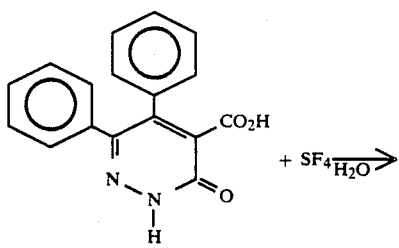

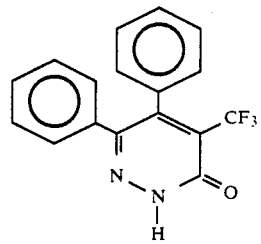

A one liter monel metal bomb was charged with 40 g (0.136 mole) of the product of Example 2 and 9.5 mls of distilled water. The bomb was sealed and chilled in dry ice and acetone bath. The system was evacuated with a vacuum pump. About 190 grams (2.0 mole) of sulfur tetrafluoride gas was injected into the bomb and sealed. The bomb was placed on a rocker apparatus, allowed to warm to room temperature, then heated to 50° C. and agitated overnight. The bomb was allowed to cool, vented and scrubbed with Nitrogen before opening. The content, a purple liquid, was dissolved in chloroform, washed with water and dried. The solvent was distilled at reduced pressure and the residual material poured down a silica column. The resulting crude material was recrystallized from absolute ethyl alcohol to give 5.0 grams of a yellow solid which melted at 235°–237° C. Calculated for $C_{17}H_{11}F_3N_2O$, C, 64.6; H, 3.5; N, 8.9. Found: C, 64.6; H, 3.7; N, 8.8.

EXAMPLE 4

N,N-Dimethyl-2,3-dihydro-3-oxo-5,6-diphenyl-4-pyridazinecarboxamide

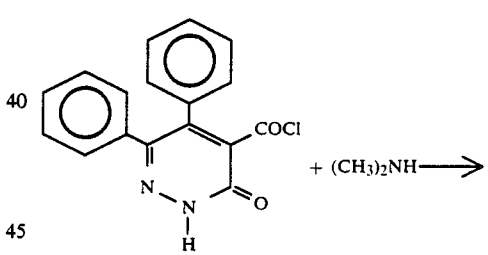

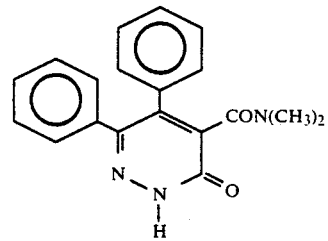

8.0 grams (0.0275 mole) of the acid chloride of the product of Example 2 was reacted with excess dimethylamine in 200 mls of toluene. This solution was heated on a steam bath for 2 hours. The solution was filtered and the filtrate distilled at reduced pressure. The residual solid was filtered, washed with petroleum ether and air dried. There was isolated 5.0 grams of a solid which when recrystallized from absolute ethyl alcohol gave 2.5 grams of a white solid that melted at 278° C. The infrared spectrum showed two carbonyl bands one at 6.0μ, the other a 6.1μ. Analysis calculated for $C_{19}H_{17}N_3O_2 \cdot 1H_2O$, C, 70.4; H, 5.4; N, 12.9. Found: C, 70.1; H, 5.5; N, 12.9.

EXAMPLE 5

4-Cyano-5,6-bis(p-fluorophenyl)-3-(2H)-pyridzainone

13.01 grams (0.05 mole) of 4,4'-difluorobenzilmonohydrazone and 6.22 grams (0.055 mole) of ethyl cyanoacetate were charged to a dry flask in 250 ml absolute ethanol. While stirring the mixture, 3.74 grams (0.055 mole) of sodium ethoxide were added portionwise. When addition was complete, the reaction was heated to reflux for 5 hours. 25% excess of base and ester were added and reaction refluxed for 5 more hours. The hot solution was quenched in an equal volume of 1N HCl. Subsequent refrigeration caused a solid to precipitate. This was filtered and washed with ether, recrystallized from acetonitrile/methanol and dried over IPA overnight. Calculated for $C_{17}H_9F_2N_3O_1$, C, 66.01; H, 2.93; N, 13.58. Found: C, 66.32; H, 3.02; N, 13.0.

EXAMPLE 6

Sodium Salt of 5,6-diphenyl-4-cyano-3-(2H)-pyridazinone

Benzilmonocyanoacetohydrazide, 12.9 grams (0.044 mole), was heated to reflux in 25 mls of 8% sodium hydroxide and 50 mls of distilled water for 45 minutes. The solution was filtered hot and allowed to cool slowly and finally chilled in an ice bath. There was isolated 11.5 grams (88.5%) yield of a yellow solid; M.W.=295.26 with the formula of $C_{17}H_{10}N_3ONa$.

EXAMPLE 6A

4-Nitro-5,6-diphenyl-(2H)-pyridazin-3-one\*

\*Aydin et al., *Chim. Acta Tur.*, 7 (1979) 121–140.

8.96 g (0.040 mole) of benzilmonohydrazone, 5.3 g (0.040 mole) of ethylnitroacetate and 4.8 g (0.056 mole) of piperidine in 100 mL of benzene were heated in a round bottom flask with a Dean-Stark trap and condenser for 24 hrs.

The mixture was evaporated to dryness in vacuo and the residue treated with a 10% solution of acetic acid and stirred at room temperature for approximately one hr.

The organic portion was refluxed in approximately 400 mL of benezene unit all was in solution then filtered (hot) through paper.

The resulting precipitate from pet. ether was suction filtered and air dried to give 2.0 g of the title compound.

TABLE I

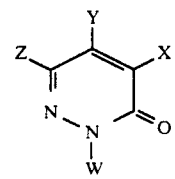

| Example Number | W | X | Y | Z |
|---|---|---|---|---|
| 1 | H | CN | $C_6H_5$ | $C_6H_5$ |
| 2 | H | COOH | $C_6H_5$ | $C_6H_5$ |
| 3 | H | $CF_3$ | $C_6H_5$ | $C_6H_5$ |
| 4 | H | —$CON(CH_3)_2$ | $C_6H_5$ | $C_6H_5$ |
| 5 | H | CN | $C_6H_4$—F—p | —$C_6H_4$—F—p |
| 6 | Na | CN | $C_6H_5$ | $C_6H_5$ |

TABLE I-continued

| Example Number | W | X | Y | Z |
|---|---|---|---|---|
| 6A | H | $NO_2$ | $C_6H_5$ | $C_6H_5$ |

Examples 7 through 17 illustrate hydroxyalkyl derivatives of diphenylpyridazinones. These compounds are summarized in Table II. Those compounds shown in Table II that are not shown by specific preparatory example have been synthesized in accordance with one of the examples manifested below.

EXAMPLE 7

2-(2'-Hydroxyethyl)-4-cyano-5,6-di-(4-chlorophenyl)-3-(2H)-pyridazinone

If the necessary benzil starting material is not commercially available, it may be prepared from the desired benzoin which in turn can be synthesized from the corresponding aldehyde and potassium cyanide. The benzil is caused to react with the cyanoacetohydrazide in DMF to give the benzilmonoacetohydrazide. The latter compound is reacted with 8% sodium hydroxide to give the corresponding diphenylpyridazinone sodium salt. This salt can then be reacted with hydrochloric acid to give the corresponding —NH compound.

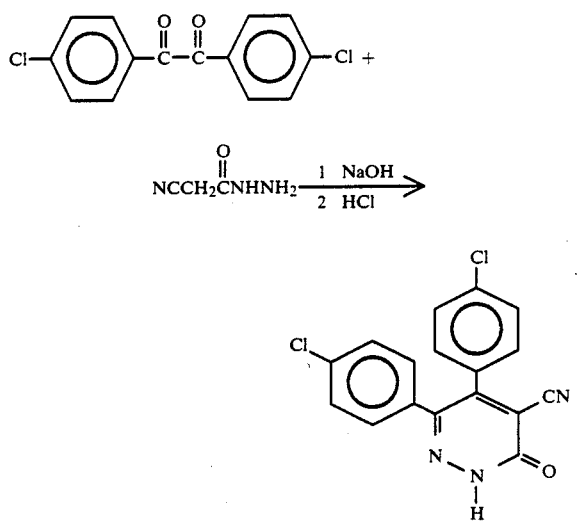

This starting material is then reacted with the requisite ester to form 2-(2'-hydroxyethyl)-4-cyano-5,6-di-(4-chlorophenyl)-3-(2H)-pyriazinone.

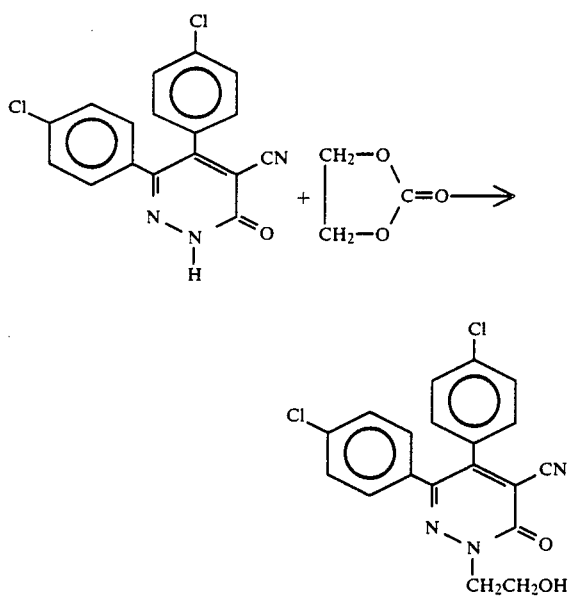

EXAMPLE 8

2-(2'-Hydroxyethyl)-4-cyano-5,6-diphenyl-3-(2H)-pyridazinone

Step 1

17.7 grams (0.065 mole) of the product of Example 1 was dissolved in 60 mls of dry dimethylformamide along with 0.25 grams of potassium hydroxide and 7.5 grams (0.085 mole) of ethylene carbonate. The mixture was heated to 100° C. and maintained for 2 hours until no carbon dioxide was liberated. The solution was then heated at 110° C. for 30 minutes. The solution was filtered and the dimethylformamide was distilled under reduced pressure with a mechanical pump. The solid was dried in a drying pistol using xylene as the solvent. The residual solid was recrystallized from ethyl alcohol to give 10.4 grams (50%) yield of a solid melting at 197°-198° C. Calculated for $C_{19}H_{15}N_3O_2$, C, 71.9; H, 4.8; N, 13.2. Found: C, 71.7; H, 4.71; N, 13.5. The infrared spectra showed the OH group at 2.9μ, the nitrile band at 4.5μ, and the carbonyl band at 6.0μ. The NMR confirmed that the product was the desired material.

Step 2

Benzilmonocyanoacetohydrazide

Benzil, 52.2 grams (0.12 mole), was dissolved in 150 mls of ethyl alcohol. This mixture was heated to reflux. 13.2 grams (0.13 mole) of cyanoacetohydrazide was added dropwise to this mixture. To this solution was added 4 mls of concentrated hydrochloric acid in 44 mls of water. After all the materials had been added, the solution was heated to reflux for 10 minutes. The solution was cooled and poured into ice and the solid filtered, washed with water to give 26 grams (74%) yield of a solid which melted at 203°-204° C. Calculated for $C_{17}H_{13}N_3O_2$, C, 70.1; H, 4.5; N, 14.4. Found: C, 70.1; H, 4.5; N, 13.8.

Step 3

Benzilmonocyanoacetohydrazide was converted to the sodium salt as shown by Example 6.

Step 4

(The hydroxy-ethyl derivative)

5.9 grams (0.02 mole) of the product of Step 3 (Example 6) was reacted with 2 grams (0.02 mole) of 2-chloro-ethanol in 20 mls of dry DMF. This solution was heated to 100° C. for 1.5 hours on a hot water bath. The solution was cooled and added slowly to 30 mls of distilled water. The precipitant solid was filtered, washed with water and air dried. There was isolated 4.5 grams (71%) yield of a crude product which when recrystallized from benzene gave 4 grams (63%) yield of a solid which melted at 198°-199° C.

The other method used to synthesize these compounds was to react the sodium salt of the desired pyridazinone with the appropriate chloro alcohol in dry dimethylformamide.

EXAMPLE 9

2-(3'-Hydroxypropyl)-4-cyano-5,6-diphenyl-3-(2H)-pyridazinone 5.0 grams (0.017 mole) of the product of Example 6 was reacted with 1.70 grams (0.017 m) of 3-chloropropanol in 60 mls of dry dimethylformamide and the solution was heated to 110° C. for 3 hours. The sodium chloride was filtered off and the solvent was distilled at reduced pressure. The residue was taken up in absolute ethyl alcohol to give 5.0 grams (68%) yield of a yellow solid which melted at 156°-157° C. The infrared spectrum showed the OH band at 3.0μ, the nitrile band at 4.5μ, and the carbonyl band at 6.1μ.

EXAMPLE 10

5,6-Diphenyl-4-cyano-2-hydroxymethyl-3-(2H)-pyridazinone 2.9 grams (0.0106 mole) of 5,6-diphenyl-4-cyano-3-(2H)-pyridazinone was reacted with 40 mls of 37% aqueous formaldehyde along with 25 mls of dimethylformamide. After the slight exothermic reaction subsided, the solution was heated on a steam bath until all the solid dissolved. On cooling, a solid precipitated out of the solution. The solid was filtered, washed with water and air dried. There was isolated 2 grams of a white solid which decomposed to the original starting material and formaldehyde at 195°-197° C. The 5,6-diphenyl-4-cyano-2-hydroxymethyl-3-(2H)-pyridazinone also reverted back to the original starting material when recrystallized from ethyl alcohol. The infrared spectrum of the recrystallized solid and the original starting material were superimposable.

TABLE II

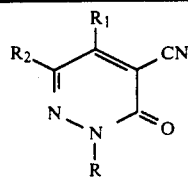

| Example Number | R | $R_1$ | $R_2$ | M.W. | M.P. C.° | Yield % | Formula | Calcd for | | Found | | Prep. |
|---|---|---|---|---|---|---|---|---|---|---|---|---|
| 8 | —CH₂CH₂OH | —C₆H₅ | —C₆H₅ | 317.31 | 197–198 | 60 | $C_{19}H_{15}N_3O_2$ | C, | 71.9 | C, | 71.7 | 8 |
| | | | | | | | | H, | 4.8 | H, | 4.71 | |
| | | | | | | | | N, | 13.2 | N, | 13.5 | |
| 10 | —CH₂OH | —C₆H₅ | —C₆H₅ | 302.27 | 195–197 | 63 | $C_{18}H_{13}N_3O_2$ | C, | 71.1 | C, | 71.7 | 10 |
| | | | | | | | | H, | 4.3 | H, | 4.7 | |
| | | | | | | | | N, | 13.90 | N, | 13.80 | |
| 11 | —(CH₂)₅OH | —C₆H₅ | —C₆H₅ | 359.41 | 148–149 | 53 | $C_{22}H_{21}N_2O_2$ | C, | 73.5 | C, | 72.6 | 9 |
| | | | | | | | | H, | 5.9 | H, | 5.7 | |
| | | | | | | | | N, | 11.7 | N, | 12.2 | |
| 12 | —CH₂CHCH₂OH<br>\|<br>OH | —C₆H₅ | —C₆H₅ | 347.34 | 160–161 | 34 | $C_{20}H_{17}N_3O_3$ | C, | 69.1 | C, | 68.4 | 9 |
| | | | | | | | | H, | 4.98 | H, | 4.93 | |
| | | | | | | | | N, | 12.01 | N, | 12.09 | |
| 13 | —CH₂CHCH₃<br>\|<br>OH | —C₆H₅ | —C₆H₅ | 331.34 | 161–162 | 53 | $C_{20}H_{17}N_3O_2$ | C, | 72.4 | C, | 71.5 | 9 |
| | | | | | | | | H, | 5.14 | H, | 5.19 | |
| | | | | | | | | N, | 12.4 | N, | 12.4 | |
| 9 | (—CH₂)₃OH | —C₆H₅ | —C₆H₅ | 331.34 | 156–157 | 68 | $C_{20}H_{17}N_3O_2$ | C, | 72.4 | C, | 71.8 | 9. |
| | | | | | | | | H, | 5.14 | H, | 5.3 | |
| | | | | | | | | N, | 12.4 | N, | 12.4 | |
| 14 | —CH₂CH₂—<br>—OCH₂CH₂OH | —C₆H₅ | —C₆H₅ | 361.36 | 108–110 | 43 | $C_{21}H_{19}N_3O_3$ | C, | 69.7 | C, | 69.5 | 9 |
| | | | | | | | | H, | 5.29 | H, | 5.3 | |
| | | | | | | | | N, | 11.62 | N, | 11.8 | |
| 15* | —CH₂CH₂OH | —C₆H₅ | —C₆H₅ | 335.32 | 246–247 | ≠ | $C_{19}H_{17}N_3O_3$ | C, | 68.1 | C, | ≠ | 9 |
| | | | | | | | | H, | 5.11 | H, | ≠ | |
| | | | | | | | | N, | 12.5 | N, | ≠ | |
| 7 | —CH₂CH₂OH | Cl—⌬— | Cl—⌬— | 356.22 | 122 | 62 | $C_{19}H_{13}Cl_2N_3O_2$ | C, | 59.1 | C, | 58.5 | 7 |
| | | | | | | | | H, | 7.4 | H, | 3.8 | |
| | | | | | | | | N, | 10.9 | N, | 10.2 | |
| 16 | —CH₂CH₂OH | Cl-⌬ (2-Cl) | Cl-⌬ (2-Cl) | 386.22 | 182–183 | 81 | $C_{19}H_{13}Cl_2N_3O_2$ | C, | 59.1 | C, | 59.2 | 7 |
| | | | | | | | | H, | 3.4 | H, | 3.6 | |
| | | | | | | | | N, | 10.9 | N, | 11.2 | |
| 17 | —CH₂CH₂OH | F—⌬— | F—⌬— | 353.29 | 212–215 | 5 | $C_{19}H_{13}F_2N_3O_2$ | C, | 64.5 | C, | 64.0 | 7 |
| | | | | | | | | H, | 3.70 | H, | 3.85 | |
| | | | | | | | | N, | 11.80 | N, | 11.62 | |

*Contains a CONH₂ group in place of the 5-cyano group.
≠Data not available
The compounds in this table were prepared in accordance to the synthesis procedure set forth in the examples represented by the numbers in this column.

Examples 18 through 29 illustrate various ester derivatives of diphenylpyridazinones. These compounds are summarized in Table III.

EXAMPLE 18

Acetate ester of 2-(2'-hydroxyethyl)-4-cyano-5,6-diphenyl-3-(2H)-pyridazinone

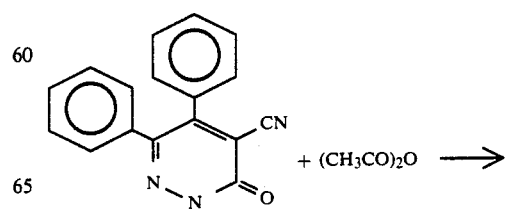

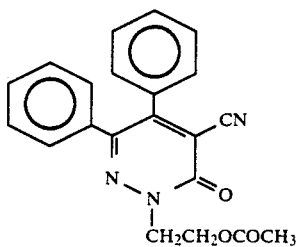

10 grams (0.031 mole) of 2-(2'-hydroxyethyl)-4-cyano-5,6-diphenyl-3-(2H)-pyridazinone was reacted with excess acetic anhydride. This mixture was heated to 100° C., at which temperature all the solid dissolved. The solution was heated an additional hour, cooled, poured into excess water and the precipitant solid was filtered, washed with water and finally petroleum ether. This material was recrystallized from ethyl alcohol to give 6.0 grams of a solid which melted at 120° C. The infrared spectrum showed the nitrile band at 4.5μ; 2 carbonyl groups, one at 5.7μ and the other at 6.0μ.

EXAMPLE 19

Benzoate of 2-(2'-hydroxyethyl)-4-cyano-5,6-diphenyl-3-(2H)-pyridazinone 2.0 grams of 2-(2'-hydroxyethyl)-4-cyano-5,6-diphenyl-3-(2H)-pyridazinone was dissolved in 4 mls of pyridine along with 2.0 grams of benzoyl chloride. The mixture was heated on a steam bath for 30 minutes. The solution was cooled, diluted with 50 mls of 5% sodium carbonate, and then the precipitant solid was filtered, washed with water and air dried. The solid was recrystallized from ethyl alcohol to give 1.6 grams (65%) yield of a solid which melted at 146°–147° C. The infrared spectrum showed two carbonyls, one at 5.7μ and the other at 6.0μ, along with the nitride band at 4.4μ.

TABLE III

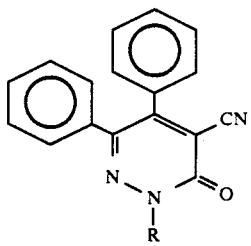

| Example Number | R | M.W. | M.P. C.° | Yield % | Formula | Calc. for | | Found | | Prep. |
|---|---|---|---|---|---|---|---|---|---|---|
| 18 | —CH$_2$CH$_2$OCOCH$_3$ | 359.35 | 129 | 54 | C$_{21}$H$_{17}$N$_3$O$_3$ | C, | 70.18 | C, | 70.5 | 18 |
|  |  |  |  |  |  | H, | 4.76 | H, | 4.76 |  |
|  |  |  |  |  |  | N, | 11.6 | N, | 11.7 |  |
| 20 | —CH$_2$CH$_2$OCOCH$_2$—CH$_3$ | 373.37 | 84–85 | 90 | C$_{22}$H$_{19}$N$_3$O$_3$ | C, | 70.7 | C, | 70.0 | 18 |
|  |  |  |  |  |  | H, | 5.12 | H, | 5.1 |  |
|  |  |  |  |  |  | N, | 11.4 | N, | 11.4 |  |
| 21 | —CH$_2$OCOCH$_3$ | 345.34 | 165–156 | 45 | C$_{20}$H$_{15}$N$_3$O$_3$ | C, | 69.6 | C, | 68.6 | 18 |
|  |  |  |  |  |  | H, | 4.4 | H, | 4.4 |  |
|  |  |  |  |  |  | N, | 12.2 | N, | 12.1 |  |
| 22 | —CH$_2$CH$_2$—O—COCH$_2$Cl | 393.80 | 104–105 | 44 | C$_{21}$H$_{16}$Cl$_1$N$_3$O$_3$ | C, | 64.0 | C, | 64.0 | 18 |
|  |  |  |  |  |  | H, | 4.09 | H, | 4.2 |  |
|  |  |  |  |  |  | N, | 10.7 | N, | 11.1 |  |
| 19 | —CH$_2$CH$_2$—OCOC$_6$H$_5$ | 421.41 | 146–147 | 65 | C$_{26}$H$_{19}$N$_3$O$_3$ | C, | 74.09 | C, | 74.4 | 19 |
|  |  |  |  |  |  | H, | 4.54 | H, | 4.75 |  |
|  |  |  |  |  |  | N, | 9.96 | N, | 10.2 |  |
| 23 | —CH$_2$CH$_2$OCO—(3,4-dichlorophenyl) | 490.52 | 147–148 | 33 | C$_{26}$H$_{17}$Cl$_2$N$_3$O$_3$ | C, | 63.6 | C, | 63.7 | 19 |
|  |  |  |  |  |  | H, | 3.49 | H, | 3.66 |  |
|  |  |  |  |  |  | N, | 8.56 | N, | 8.7 |  |
| 24 | —CH$_2$OCOC$_2$H$_5$ | 359.30 | 176–177 | 65 | C$_{21}$H$_{17}$H$_3$O$_3$ | C, | 70.2 | C, | 70.2 | 18 |
|  |  |  |  |  |  | H, | 4.76 | H, | 4.90 |  |
|  |  |  |  |  |  | N, | 11.6 | N, | 11.6 |  |
| 25 | —CH$_2$CH$_2$OCO—(4-methylphenyl) | 435.44 | 161–162 | 42 | C$_{27}$H$_{21}$N$_3$O$_2$ | C, | 74.4 | C, | 73.9 | 19 |
|  |  |  |  |  |  | H, | 4.86 | H, | 4.99 |  |
|  |  |  |  |  |  | N, | 9.64 | N, | 10.3 |  |
| 26 | —CH$_2$CH$_2$CH$_2$—OCOCHCl$_2$ | 428.25 | 148–150 | 65 | C$_{22}$H$_{17}$Cl$_2$N$_3$O$_3$ | C, | 58.89 | C, | 59.22 | 18 |
|  |  |  |  |  |  | H, | 3.53 | H, | 3.75 |  |
|  |  |  |  |  |  | N, | 9.80 | N, | 9.81 |  |
| 27 | —CH$_2$CH$_2$CH$_2$OCOCH$_3$ | 373.37 | 107–109 | 100 | C$_{22}$H$_{19}$N$_3$O$_3$ | C, | 70.8 | C, | 70.0 | 18 |
|  |  |  |  |  |  | H, | 5.12 | H, | 5.12 |  |
|  |  |  |  |  |  | N, | 11.4 | N, | 11.4 |  |

TABLE III-continued

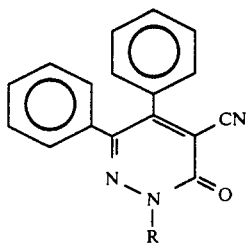

| Example Number | R | M.W. | M.P. C.° | Yield % | Formula | Calc. for | Found | Prep. |
|---|---|---|---|---|---|---|---|---|
| 28 | —CH₂CH₂CH₂—OCOCH₂CH₃ | 387.40 | 97–98 | 69 | C₂₃H₂₁N₃O₃ | C, 71.3<br>H, 5.6<br>N, 10.8 | C, 69.8<br>H, 5.75<br>N, 10.6 | 18 |
| 29* | —CH₂CH₂O—CO(CH₂)COOH | 456.32 | 157–158 | ≠ | C₂₃H₁₇Cl₂N₃O₅ | C, 56.8<br>H, 3.52<br>N, 8.64 | C, 56.7<br>H, 3.57<br>N, 8.5 | 18 |

≠ Data Not Available
*Contains the 4-chlorophenyl in place of the phenyl
The compounds in this table were prepared in accordance to the synthesis procedure set forth in the examples represented by the numbers in this column.

Examples 30 through 63 illustrate acetate ester derivatives of diphenylpyridazinones. These compounds are summarized in Table IV and portions of Table XXVIII.

EXAMPLE 30

Acetic acid, 5-cyano-1,6-dihydro-6-oxo-3,4-diphenylpyridazin-1-yl ethyl ester 10.4 grams (0.035 mole) of the product of Example 6 was reacted with 5.9 grams (0.035 mole) of ethyl bromoacetate in 100 mls of dimethylformamide. This solution was heated to 100° C. for 2 hours, cooled, and the sodium bromide filtered. The filtrate was poured into a mixture of ice and water and the precipitant solid was filtered, washed with water and air dried. This solid was recrystallized from ethyl alcohol to give 8.0 grams (63%) of a white solid that melted at 141°–142° C. The infrared spectrum showed the nitrile band at 4.5μ, two carbonyl bands, one at 5.7μ the other at 5.99μ.

EXAMPLE 31

Acetic acid, 5-cyano-1,6-dihydro-6-oxo-3,4-diphenylpyridazin-1-yl 22.0 grams (0.061 mole) of the product of Example 30 was reacted with 25.0 grams (0.18 mole) of potassium carbonate in 150 mls of a 50% aqueous ethyl alcohol. This mixture was heated to reflux for 3 hours. The solvent was distilled at reduced pressure and the residual solid was dissolved in water. The solution was poured into an excess of hydrochloric acid and ice. The precipitant solid was filtered, washed with water and air dried. The white solid was recrystallized from absolute ethyl alcohol to give 14.0 grams (70%) yield of a solid melting with decomposition at 240°–241° C. The infrared spectrum showed the nitrile band at 4.4μ, two carbonyl bands, one at 5.7μ, the other at 5.99μ.

EXAMPLE 32

1-Pyridazineacetylchloride, 5-cyano-1,6-dihydro-6-oxo-3,4-diphenyl 50 grams (0.150 mole) of the product of Example 31 were dissolved in 200 mls of THF. 22 grams (0.184 mole) of thionyl chloride were added dropwise to this solution. This solution was heated to reflux for 4 hours, cooled and the solvent distilled at reduced pressure. There was isolated a quantitative crude yield of the desired product.

EXAMPLE 33

Acetic acid, 5-cyano-1,6-dihydro-6-oxo-3,4-diphenylpyridazin-1-yl-3-methyl-3-butenyl ester

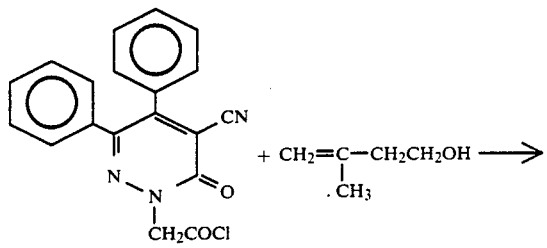

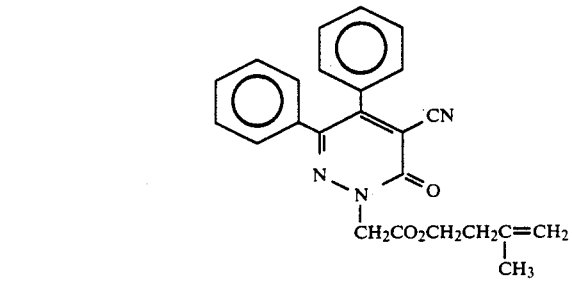

10 grams (0.0285 mole) of the product of Example 32 was reacted with excess 3-methyl-3-butenol and the reaction mixture heated to 100° C. for 3 hours. The excess alcohol was distilled at reduced pressure and the residual oil was taken up in absolute ethyl alcohol. The precipitant solid was filtered, washed with ethyl alcohol and air dried. There was isolated 8.0 grams (70%) of a brownish solid that melted at 102°–103° C. The infrared spectrum showed the nitrile band at 4.5μ, two carbonyl bands, one at 5.7μ, the other at 6.0μ.

EXAMPLE 34

Acetic acid, 5-cyano-1,6-dihydro-6-oxo-3,4-diphenylpyridazin-1-yl-1-octyl ester

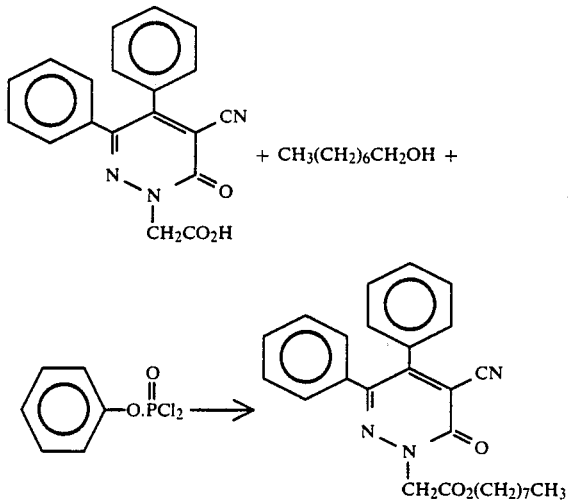

4.8 grams (0.014 mole) of the product of Example 31 was dissolved in 100 mls of acetonitrile and placed in a 250 ml flask equipped with stirrer, condenser, thermometer, and a pressure equalizing dropping funnel. To this solution was added 6.8 grams (0.086 mole) of pyridine and the mixture stirred at −5° C. When this temperature was reached, 9.1 grams (0.043 mole) of phenyl dichlorophosphate dissolved in 20 mls of acetonitrile was added dropwise. To this mixture was added, in one portion, 7.6 grams (0.058 mole) of 1 octanol. This mixture was stirred at room temperature overnight, poured into 300 mls of 1-normal hydrochloric acid and stirred for 30 minutes. The solution was extracted with ethyl acetate, washed with water, separated and dried over sodium sulfate. The solvent was distilled at reduced pressure and the residual oil purified by passing it through a dry column and diluting it with 90% chloroform and 10% ethyl acetate. There was isolated 1.2 grams of the desired product. An analytical sample was prepared by recrystallizing a small sample of this product from ethyl alcohol.

EXAMPLE 35

Acetic acid, 5-cyano-1,6-dihydro-6-oxo-3,4-diphenylpyridazin-1-yl-p-chlorophenyl ester*

*Hsing-Jang Liu et al, *Tetrahedron Letters*, No. 46, p 4461–4464 (1978)

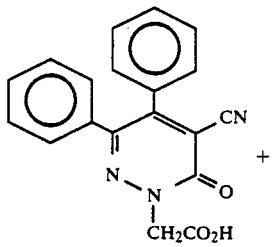

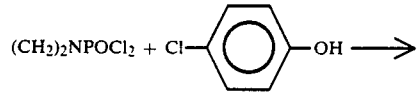

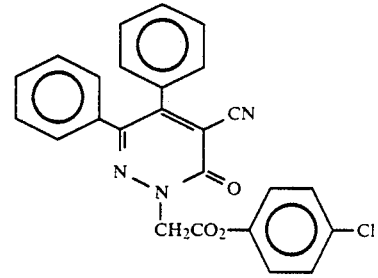

10 grams (0.03 mole) of the product of Example 31 was dissolved in 100 mls of tetrahydrofuran in a 500 ml 3-necked flask equipped with stirrer, dropping funnel and thermometer. To this mixture was added 7.3 grams (0.072 mole) of triethylamine in one portion. This mixture was stirred until a thick slurry resulted, at which time 9.2 grams (0.057 mole) of dimethylamido phosphoryl chloride dissolved in 50 mls of tetrahydrofuran was added dropwise. This mixture was stirred for 30 minutes at room temperature. 8.5 grams (0.066 mole) of p-chlorophenol in 50 mls of THF was then added and the solution stirred at room temperature for 18 hours. The solution was extracted with ethyl acetate, dried over sodium sulfate, filtered and the solvent diluted at reduced pressure. The resulting semi-solid was separated through a dry silica column and eluted with 80% chloroform and 20 ethyl acetate, to give 5.6 grams of a crude product. The solid was recrystallized from ethyl alcohol to give 3.0 grams of the desired product.

EXAMPLE 36

Preparation of 5-aminocarbonyl-1,6-dihydro-6-oxo-3,4-diphenyl-pyridazin-1-yl, ethyl ester

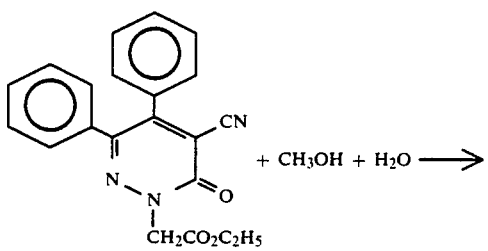

54.6 grams of the product of Example 30 was heated to reflux with aqueous methyl alcohol (40% water and 60% methyl alcohol). This solution was refluxed for 5 hours, cooled and the solvent distilled at reduced pressure. The residual solid was taken up in benzene, filtered, cooled, and the precipitant product was filtered, washed with petroleum ether and air dried. This solid was recrystallized form absolute ethyl alcohol to give 17.8 grams of a white solid that melted at 117°-119° C. The infrared spectrum showed the NH band at 3.1μ, and two carbonyl bands.

TABLE IV

[Structure: pyridazinone with $C_6H_5$ at 4-position, $H_5C_6$ at 5-position, CN at 3-position, =O at 2-position, N–N ring, N-substituent $CH_2COOR$]

| Example Number | R | M.W. | M.P. C.° | Yield % | Formula | Calc. for | | Found | | Prep. |
|---|---|---|---|---|---|---|---|---|---|---|
| 37 | —$CH_3$ | 345.34 | 174–175 | 50 | $C_{20}H_{15}N_3O_3$ | C, | 69.5 | C, | 68.4 | 33 |
| | | | | | | H, | 4.4 | H, | 4.5 | |
| | | | | | | N, | 12.1 | N, | 11.5 | |
| 30 | —$C_2H_5$ | 359.35 | 141–142 | 63 | $C_{21}H_{17}N_3O_3$ | C, | 70.2 | C, | 70.2 | 30 |
| | | | | | | H, | 4.77 | H, | 4.99 | |
| | | | | | | N, | 11.7 | N, | 12.01 | |
| 38 | i-$C_3H_7$ | 373.39 | 165–166 | 67 | $C_{22}H_{19}N_3O_3$ | C, | 70.8 | C, | 70.1 | 33 |
| | | | | | | H, | 5.1 | H, | 5.2 | |
| | | | | | | N, | 11.3 | N, | 10.8 | |
| 39 | n-$C_3H_7$ | 373.39 | 141–142 | 79 | $C_{22}H_{19}N_3O_3$ | C, | 70.8 | C, | 70.4 | 33 |
| | | | | | | H, | 5.1 | H, | 5.1 | |
| | | | | | | N, | 11.3 | N, | 10.8 | |
| 40 | —$CH_2CH_2$—$OCH_3$ | 389.39 | 152–153 | 68 | $C_{22}H_{19}N_3O_3$ | C, | 67.9 | C, | 67.6 | 33 |
| | | | | | | H, | 4.9 | H, | 4.9 | |
| | | | | | | N, | 10.8 | N, | 10.7 | |
| 41 | —$CH_2CH=CH_2$ | 371.36 | 125–126 | 50 | $C_{22}H_{17}N_3O_3$ | C, | 71.1 | C, | 71.0 | 33 |
| | | | | | | H, | 4.61 | H, | 4.7 | |
| | | | | | | N, | 11.3 | N, | 11.3 | |
| 42 | —$CH_2CH_2Cl$ | 393.98 | 144 | 63 | $C_{21}H_{16}Cl_1N_3O_2$ | C, | 64.0 | C, | 63.8 | 33 |
| | | | | | | H, | 4.09 | H, | 4.1 | |
| | | | | | | N, | 10.6 | N, | 10.6 | |
| 43 | —$CH_2C{\equiv}CH$ | 369.34 | 144–145 | 80 | $C_{22}H_{15}N_3O_3$ | C, | 71.4 | C, | 70.9 | 33 |
| | | | | | | H, | 4.09 | H, | 4.1 | |
| | | | | | | N, | 11.3 | N, | 11.2 | |
| 44 | n-$C_4H_9$ | 387.40 | 124–125 | 75 | $C_{23}H_{21}N_3O_3$ | C, | 71.3 | C, | 71.2 | 33 |
| | | | | | | H, | 5.46 | H, | 5.45 | |
| | | | | | | N, | 10.8 | N, | 10.8 | |
| 45 | —$CH_2CH$—$CH_3$ \| $CH_3$ | 387.40 | 140–141 | 52 | $C_{23}H_{21}N_3O_3$ | C, | 71.3 | C, | 70.4 | 33 |
| | | | | | | H, | 5.5 | H, | 5.4 | |
| | | | | | | N, | 10.9 | N, | 10.6 | |
| 46 | —$C(CH_3)_3$ .5$CH_3CH$ | 403.40 | 165–167 | 30 | $C_{23}H_{21}N_3O_3$ .5$CH_3OH$ | C, | 69.9 | C, | 69.9 | 33 |
| | | | | | | H, | 5.7 | H, | 5.52 | |
| | | | | | | N, | 10.4 | N, | 10.5 | |
| 47 | —$CHCH_2CH_3$ \| $CH_3$ | 387.40 | 136–137 | 27 | $C_{23}H_{21}N_3O_3$ | C, | 71.3 | C, | 70.9 | 33 |
| | | | | | | H, | 5.6 | H, | 5.5 | |
| | | | | | | N, | 10.8 | N, | 10.7 | |
| 48 | —$CH_2$—$C=CH_2$ \| $CH_3$ | 385.38 | 101–102 | 20 | $C_{23}H_{19}N_3O_3$ | C, | 71.6 | C, | 71.1 | 33 |
| | | | | | | H, | 4.96 | H, | 5.06 | |
| | | | | | | N | 10.9 | N, | 10.9 | |
| 49 | —$CH_2CH$—$CH_2CH_3$ \| $C_2H_5$ | 415.45 | 105–107 | 77 | $C_{25}H_{25}N_3O_3$ | C, | 72.3 | C, | 72.8 | 33 |
| | | | | | | H, | 6.06 | H, | 6.2 | |
| | | | | | | N, | 10.1 | N, | 10.2 | |
| 33 | —$CH_2CH_2$—$C=CH_2$ \| $CH_3$ | 399. | 102–103 | 37 | $C_{24}H_{21}N_3O_3$ | C, | 72.1 | C, | 71.5 | 33 |
| | | | | | | H, | 5.3 | H, | 5.38 | |
| | | | | | | N, | 10.5 | N, | 10.48 | |
| 50 | $CH_3$ \| —C—$C{\equiv}CH$ \| $CH_3$ | 406.39 | 168–170 | 33 | $C_{24}H_{19}N_3O_3$ .5$H_2O$ | C, | 70.9 | C, | 70.9 | 33 |
| | | | | | | H, | 4.61 | H, | 4.77 | |
| | | | | | | N, | 10.3 | N, | 10.5 | |
| 51 | —$CH_2CH_2$—$CHCH_3$ \| $OCH_3$ | 417.2 | oil | 58 | $C_{24}H_{23}N_3O_4$ | C, | 69.0 | C, | 68.9 | 33 |
| | | | | | | H, | 5.55 | H, | 5.63 | |
| | | | | | | N, | 10.0 | N, | 10.1 | |

TABLE IV-continued

Structure:

$H_5C_6$ and $C_6H_5$ substituents on pyridazinone ring with CN group and $CH_2COOR$ on N.

| Example Number | R | M.W. | M.P. C.° | Yield % | Formula | Calc. for | | Found | | Prep. |
|---|---|---|---|---|---|---|---|---|---|---|
| 52 | —CH$_2$CH$_2$O—CH$_2$OCH$_3$ | 433.44 | 65–67 | 37 | $C_{23}H_{21}N_3O_5$ | C, 66.5<br>H, 5.4<br>N, 9.7 | | C, 66.2<br>H, 5.1<br>N, 10.5 | | 33 |
| 53 | —CH$_2$C(CH$_3$)$_3$ | 401.42 | 174–175 | 38 | $C_{24}H_{23}N_3O_3$ | C, 71.8<br>H, 5.77<br>N, 10.46 | | C, 71.3<br>H, 5.75<br>N, 10.5 | | 33 |
| 54 | —n-C$_5$H$_{11}$ | 412.92 | 95–97 | 62 | $C_{24}H_{23}N_3O_4$·$C_2H_5OH$ | C, 71.2<br>H, 5.9<br>N, 10.2 | | C, 70.7<br>H, 5.8<br>N, 10.3 | | 33 |
| 55 | —CH$_2$CH(CH$_2$)$_3$CH$_3$<br>$\quad\quad$\|<br>$\quad\quad$C$_2$H$_5$ | 443.50 | 65–67 | 72 | $C_{27}H_{29}N_3O_3$ | C, 73.1<br>H, 6.59<br>N, 9.47 | | C, 73.4<br>H, 6.92<br>N, 9.6 | | 33 |
| 56 | (—CH$_2$)$_5$CH$_3$ | 415.45 | 76–78 | 55 | $C_{25}H_{25}N_3O_3$ | C, 72.2<br>H, 6.49<br>N, 10.1 | | C, 72.2<br>H, 6.3<br>N, 10.2 | | 33 |
| 57 | —CH$_2$CH$_2$—S—C$_2$H$_5$ | 419.5 | 85–86 | 50 | $C_{23}H_{21}N_3O_3S_1$ | C, 65.8<br>H, 5.05<br>N, 10.0 | | C, 65.6<br>H, 4.99<br>N, 9.96 | | 33 |
| 58 | —(CH$_2$)$_{11}$CH$_3$ | 499.60 | 70–71 | 11 | $C_{31}H_{37}N_3O_3$ | C, 74.5<br>H, 7.46<br>N, 8.46 | | C, 74.1<br>H, 7.48<br>N, 8.40 | | 33 |
| 59 | —CH—(CH—CH$_3$\|CH$_3$)$_2$ | 429.5 | 135–138 | ≠ | $C_{26}H_{27}N_3O_3$·¼H$_2$O | C, 70.5<br>H, 6.4<br>N, 9.5 | | C, 70.9<br>H, 6.1<br>N, 9.8 | | 33 |
| 204 | —(CH$_2$)$_4$Cl | 421.88 | 107–110 | 67 | $C_{23}H_{20}Cl_1N_3O_3$ | C, 65.5<br>H, 5.8<br>N, 10.0<br>Cl, 8.4 | | C, 65.7<br>H, 5.1<br>N, 10.2<br>Cl, 8.7 | | 33 |
| 205 | —(CH$_2$)$_3$Cl | 407.82 | 135–136 | 80 | $C_{22}H_{18}Cl_1N_3O_3$ | C, 64.68<br>H, 4.4<br>N, 10.2 | | C, 64.7<br>H, 4.6<br>N, 10.2 | | 33 |
| 206 | —(CH$_2$)$_6$Cl | 449.90 | 92 | 73 | $C_{25}H_{24}Cl_1N_3O_3$ | C, 66.7<br>H, 5.4<br>N, 9.3 | | C, 66.5<br>H, 5.5<br>N, 9.2 | | 33 |
| 207 | —CHCH$_2$Cl<br>$\quad$\|<br>$\quad$CH$_3$ | 407.82 | 129–130 | 63 | $C_{22}H_{18}Cl_1N_3O_3$ | C, 64.8<br>H, 4.4<br>N, 10.2 | | C, 64.8<br>H, 4.4<br>N, 10.5 | | 33 |
| 208 | —CH$_2$CH$_2$OCOCH=CH$_2$ | 429.31 | 128–131 | 49 | $C_{24}H_{19}N_3O_5$·½H$_2$O | C, 65.7<br>H, 4.19<br>N, 9.5 | | C, 65.4<br>H, 4.30<br>N, 9.1 | | 33 |
| 209 | —CH$_2$CH$_2$CN | 384.35 | 87–92 | 43 | $C_{22}H_{16}N_4O_3$ | C, 68.7<br>H, 4.1<br>N, 14.5 | | C, 68.3<br>H, 4.1<br>N, 14.3 | | 33 |
| 34 | —(CH$_2$)$_7$CH$_3$ | 443.54 | 85–87 | ≠ | $C_{27}H_{29}N_3O_3$ | C, 73.1<br>H, 6.6<br>N, 9.5 | | C, 73.5<br>H, 6.7<br>N, 9.6 | | 34 |
| 60 | —(CH$_2$)$_{15}$CH$_3$ | 555.71 | 91–93 | 25 | $C_{35}H_{45}N_3O_3$ | C, 75.6<br>H, 8.16<br>N, 7.55 | | C, 75.3<br>H, 8.47<br>N, 7.63 | | 33 |
| 35 | —C$_6$H$_4$-Cl (para) | 441.87 | 153–155 | 23 | $C_{25}H_{16}Cl_1N_3O_3$ | C, 67.9<br>H, 3.7<br>N, 9.5 | | C, 67.1<br>H, 3.6<br>N, 9.6 | | 35 |
| 61 | cyclopentyl (—CH with H$_2$C—CH$_2$ / H$_2$C—CH$_2$ ring) | 413.43 | 161–162 | 44 | $C_{25}H_{23}N_3O_3$ | C, 72.6<br>H, 5.60<br>N, 10.1 | | C, 72.3<br>H, 5.64<br>N, 10.1 | | 33 |

TABLE IV-continued

Structure (header):

$H_5C_6$ and $C_6H_5$ substituents on a pyridazinone ring with CN and =O groups; N-N with CH$_2$COOR substituent.

| Example Number | R | M.W. | M.P. °C. | Yield % | Formula | Calc. for | Found | Prep. |
|---|---|---|---|---|---|---|---|---|
| 62 | Entire Structure Below: (4-Cl-C$_6$H$_4$ and 4-Cl-C$_6$H$_4$ substituents; CH$_2$CO$_2$CH$_3$) | 414.23 | 148–151 | ≠ | C$_{20}$H$_{13}$Cl$_2$N$_3$O$_3$ | C, 57.98 H, 3.16 N, 10.14 | C, 57.97 H, 3.09 N, 10.17 | 33 |
| 36 | (diphenyl; CONH$_2$ instead of CN; CH$_2$CO$_2$CH$_3$) | 377.40 | 117–119 | ≠ | C$_{21}$H$_{19}$N$_3$O$_4$ | C, 66.8 H, 5.07 N, 11.13 | C, 66.1 H, 5.1 N, 11.2 | 36 |
| 63 | (4-F-C$_6$H$_4$ and 4-F-C$_6$H$_4$; CH$_2$COOCH$_3$) | 351.34 | 158–160 | ≠ | C$_{20}$H$_{13}$F$_2$N$_3$O$_3$ | C, 65.7 H, 3.31 N, 11.5 | C, ≠ H, ≠ N, ≠ | 33 |
| 32 | (diphenyl; CH$_2$COCl) | 349.77 | 138–141 | ≠ | C$_{19}$H$_{12}$Cl$_1$N$_3$O$_2$ | C, 65.29 H, 4.28 N, 10.29 | C, ≠ H, ≠ N, ≠ | 32 |

≠ = Data Not Available

The compounds in this table were prepared in accordance with the synthesis procedure set forth in the examples represented by the numbers in this column.

Examples 64 through 85 illustrate propionate ester derivatives of diphenylpyridazinones. These compounds are summarized in Table V and portions of Table XXVIII.

Propionic acid,
3-(5-cyano-1,6-dihydro-6-oxo-3,4-diphenylpyridazin-1-yl)

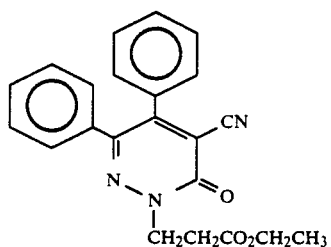

+ K₂CO₃ $\xrightarrow{\text{HCl}}$

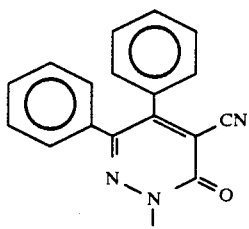

The synthesis of the product of Example 64 is performed in accordance with that procedure set forth in Example 31.

EXAMPLE 65

1-Pyridazinepropionylchloride, 5-cyano-1,6-dihydro-6-oxo-3,4-diphenyl

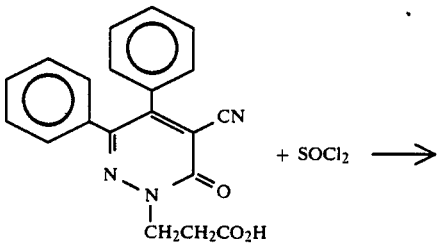

+ SOCl₂ ⟶

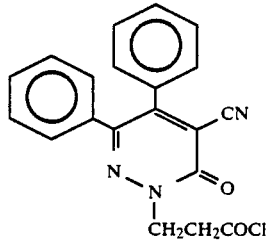

The synthesis of the product of Example 65 is performed in accordance with that procedure set forth in Example 32.

EXAMPLE 66

Propionic acid,
3-(5-cyano-1,6-dihydro-6-oxo-3,4-diphenylpyridazin-1-yl)-isobutyl ester 13.0 grams (0.0342 mole) of the product of Example 65 was reacted with 100 mls of isobutyl alcohol. This mixture was heated to reflux for 3 hours, cooled and the alcohol distilled at reduced pressure. The residual solid was recrystallized from absolute ethyl alcohol to give 8.9 grams (65%) yield of a solid that melted at 84°–86° C. The infrared spectrum showed the nitrile band at 4.5μ, two carbonyl bands, one at 5.8μ, the other at 6.0μ.

EXAMPLE 67

Propionic acid,
3-(5-cyano-1,6-dihydro-6-oxo-3,4-diphenylpyridazin-1-yl)ethyl ester

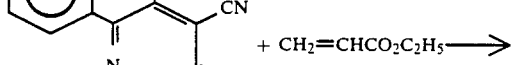

+ CH₂=CHCO₂C₂H₅ ⟶

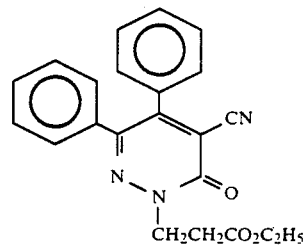

10 grams (0.0366 mole) of the product of Example 1 was reacted with 3.68 grams (0.036 mole) of ethyl acrylate in 60 mls of pyridine containing 5 mls of distilled water. This solution was heated to reflux for 3 hours, cooled, and the solvent distilled at reduced pressure. The residual solid was recrystallized from ethyl alcohol to give 10 grams (73%) yield of a solid melting at 131°–132° C. The infrared spectrum showed the nitrile band at 4.5μ, two carbonyl bands, one at 5.8μ, the other at 6.0μ.

EXAMPLE 68

Propionic acid,
3-(5-cyano-1,6-dihydro-6-oxo-3,4-di-(4-fluorophenyl)-pyridazin-1-yl)ethyl ester 4.98 grams (0.016 moles) of 5,6-di-(p-fluorophenyl)-4-cyano-3-(2H)-pyridazin-6-one was reacted with 1.6 grams (0.016 mole) of ethyl acrylate in 80 mls of pyridine containing 5 mls of distilled water. This solution was heated to reflux for 3 hours, cooled and the solvent distilled at reduced pressure. The residual oil was taken up in a mixture of ethyl alcohol and petroleum ether to give 2.2 grams (34%) yield of a solid melting at 103°–104° C. The infrared spectrum showed the nitrile band at 4.5μ, two carbonyl bands, one at 5.8μ, the other at 6.1μ.

EXAMPLE 69

Propionic acid,
3-(5-trifluoromethyl-1,6-dihydro-6-oxo-3,4-diphenyl-pyridazin-1-yl)ethyl ester 3.3 grams (0.01 mole) of the product of Example 3 was caused to react with 1.1 grams (0.01 mole) of ethyl acrylate in 30 mls of pyridine containing 1.5 mls of distilled water. This solution was heated to reflux for 8 hours, cooled and the solvent distilled at reduced pressure. The residual solid was taken up in ethyl acetate, washed with water and separated. The organic layer was dried over sodium sulfate, filtered and the solvent distilled at reduced pressure. The residual solid was recrystallized from 95% ethyl alcohol to give 0.7 gram of a solid melting at 81°–83° C. The infrared spectrum showed the nitrile band at 4.5μ, two carbonyl bands, one at 5.8μ, the other at 6.1μ.

EXAMPLE 70

Propionic acid, 3-(5-cyano-1,6-dihydro-6-oxo-3,4-diphenylpyridazin-1-yl)-2-octyl ester Following the procedure given in Tetrahedron Letters No. 46, pages 4461–4464 (1978), 5.0 grams (0.0144 mole) of the product of Example 64 was charged to a dry 200 ml 3-necked flask equipped with stirrer, condenser, drying tube and thermometer along with 100 mls of 1,2-dimethoxyethane. This solution was cooled to 5° C., and 6.8 grams (0.086 mole) of pyridine was added in small portions. This mixture was stirred for 5 minutes and 9.1 grams (0.043 mole) of phenyl dichlorophosphate was added dropwise over a 10-minute period. 7.6 grams (0.058 mole) of 2-octanol was added to this solution and the mixture stirred at room temperature for 64 hours. This solution was then poured into 300 mls of 1 normal hydrochloric acid. The organic layer was extracted with 50 mls of chloroform, washed with water, dried over sodium sulfate and the solvent distilled at reduced pressure. The residual oil was purified by passing the material through a silica column. There was isolated 1.7 grams of the desired product.

EXAMPLE 71

Propionic Acid, 3-(5-cyano-1,6-dihydro-6-oxo-3,4-diphenylpyridazin-1-yl-2-hydroxyethylester 10 grams (0.0368 mole) of the product of Example 1 was caused to react with 5 mls. of 2-hydroxymethyl acrylate in 80 mls. of pyridine containing 10 mls. of distilled water. This solution was heated to reflux for 5 hours, cooled and the solvent distilled at reduced pressure. The residual oil was taken up in ethyl alcohol and the solid that precipitated out was filtered, washed with pet ether, and air dried. There was isolated 13 grams (91%) yield of a solid which melted at 130°–131° C. The IR spectrum showed the OH group at 2.8μ, the c-c band at 3.4μ, the nitrile band at 4.5μ, and two carbonyl bands, one at 4.78μ, the other at 6.0μ.

EXAMPLE 72

The acetate of propionic acid, 3-(5-cyano-1,6-dihydro-6-oxo-3,4-diphenylpyridazin-1-yl)-hydroxy ethyl ester 10 grams (0.026 mole) of the product of Example 71 was reacted with 25 mls of acetic anhydride in 25 mls of pyridine and the mixture was heated to 70° C. for 1.5 hours. This solution was cooled, poured into excess water and stirred for 1 hour. The mixture was extracted with ethyl ether (1000 mls), washed with water and dried. The solvent was distilled at reduced pressure and the residual traces of solvent were removed with a mechanical pump. There was isolated 9.0 grams of a viscous amber oil.

EXAMPLE 73

Propionic acid, 3-(5-cyano-1,6-dihydro-6-oxo-3,4-diphenylpyridazin-1-yl)-2-chloroethyl ester 10 grams (0.062 mole) of the product of Example 71 was reacted with 8.1 grams (0.068 mole) of thionyl chloride in 50 mls of methylene chloride. The mixture was stirred at room temperature overnight. The solvent was then distilled at reduced pressure and the residual oil was placed in a mechanical vacuum to remove the last traces of solvent. There was isolated 5.3 grams of a red orange oil.

TABLE V

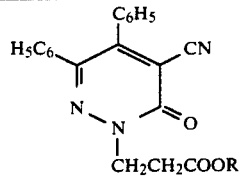

CH$_2$CH$_2$COOR

| Example Number | R | M.W. | M.P. °C. | Yield % | Formula | Calc. for | Found | Prep. |
|---|---|---|---|---|---|---|---|---|
| 74 | —CH$_3$ | 359.34 | 135–136 | 76 | C$_{21}$H$_{17}$N$_3$O$_3$ | C, 70.1<br>H, 4.76<br>N, 11.6 | C, 69.9<br>H, 4.73<br>N, 11.6 | 66 |
| 67 | —C$_2$H$_5$ | 373.3 | 131–132 | 75 | C$_{22}$H$_{19}$N$_3$O$_3$ | C, 70.7<br>H, 5.02<br>N, 11.2 | C, 69.8<br>H, 5.0<br>N, 11.1 | 67 |
| 75 | n-C$_3$H$_7$ | 387.42 | ≠ | 95 | C$_{23}$H$_{21}$N$_3$O$_3$ | C, 71.3<br>H, 5.46<br>N, 10.8 | C, 70.9<br>H, 5.4<br>N, 11.2 | 66 |
| 76 | i-C$_3$H$_7$ | 387.42 | ≠ | 86 | C$_{23}$H$_{21}$N$_3$O$_3$ | C, 71.3<br>H, 5.40<br>N, 10.8 | C, 71.4<br>H, 5.1<br>N, 10.8 | 66 |
| 77 | —CH$_2$CH=CH$_2$ | 385.3 | 93–94 | 11 | C$_{23}$H$_{19}$H$_3$O$_3$ | C, 71.6<br>H, 4.95<br>N, 10.8 | C, 71.6<br>H, 4.98<br>N, 10.8 | 67 |
| 78 | —CH$_2$CH$_2$OCH$_3$ | 403.4 | 80–81 | 68 | C$_{23}$H$_{21}$N$_3$O$_4$ | C, 68.4<br>H, 5.24<br>N, 10.4 | C, 68.0<br>H, 5.4<br>N, 10.3 | 67 |
| 73 | —CH$_2$CH$_2$Cl | 407.85 | oil | 51 | C$_{22}$H$_{18}$ClN$_3$O$_3$ | C, 64.8<br>H, 4.5 | C, 64.0<br>H, 4.4 | 73 |

TABLE V-continued

Structure:

$H_5C_6$ and $C_6H_5$ groups on pyridazinone ring with CN and =O substituents, N-N with CH₂CH₂COOR substituent.

| Example Number | R | M.W. | M.P. °C. | Yield % | Formula | Calc. for | Found | Prep. |
|---|---|---|---|---|---|---|---|---|
| 71 | —CH₂CH₂OH | 389.37 | 130-131 | 91 | $C_{22}H_{19}N_3O_4$ | N, 10.3<br>C, 67.7<br>H, 4.91 | N, 10.0<br>C, 67.5<br>H, 4.98 | 67 |
| 79 | —CH₂CH₂OC₂H₅ | 417.42 | oil | 84 | $C_{24}H_{23}N_3O_4$ | N, 10.7<br>C, 69.5<br>H, 5.5 | N, 10.7<br>C, 68.9<br>H, 5.5 | 67 |
| 72 | —CH₂CH₂OCOCH₃ | 419.43 | oil | 82 | $C_{22}H_{21}N_3O_5$ | N, 10.0<br>C, 65.9<br>H, 5.0 | N, 10.3<br>C, 66.4<br>H, 5.0 | 72 |
| 80 | n-C₄H₉ | 401.42 | 73-75 | 60 | $C_{24}H_{23}N_3O_3$ | N, 10.0<br>C, 71.8<br>H, 5.77<br>N, 10.4 | N, 9.6<br>C, 72.2<br>H, 5.78<br>N, 10.8 | 66 |
| 66 | —CH₂CH(CH₃)CH₃ | 401.42 | 84.86 | 66 | $C_{24}H_{23}N_3O_3$ | C, 71.8<br>H, 5.77<br>N, 10.4 | C, 71.4<br>H, 5.7<br>N, 10.6 | 66 |
| 81 | —C(CH₃)₃ | 401.42 | 122-123 | 26 | $C_{24}H_{23}N_3O_3$ | C, 71.8<br>H, 5.77<br>N, 10.4 | C, 72.0<br>H, 5.8<br>N, 10.4 | 67 |
| 82 | —CH₂CH₂OCH₂CH₂OC₂H₅·H₂O | 461.47 | 89-91 | 35 | $C_{26}H_{27}N_3O_5·H_2O$ | C, 65.1<br>H, 6.0<br>N, 8.75 | C, 65.2<br>H, 5.9<br>N, 8.75 | 67 |
| 70 | —CH(CH₃)—(CH₂)₅—CH₃ | 457.57 | oil | 62 | $C_{26}H_{31}N_3O_3$ | C, 73.5<br>H, 6.8<br>N, 9.2 | C, 72.8<br>H, 7.2<br>N, 8.6 | 70 |
| 83 | 4-methylphenyl | 435.48 | 155-116 | 12 | $C_{27}H_{21}N_3O_3$ | C, 74.47<br>H, 4.86<br>N, 9.6 | C, 74.5<br>H, 4.8<br>N, 9.8 | 67 |
| 84 | phenyl | 421.41 | 197-199 | 39 | $C_{26}H_{19}N_3O_3$ | C, 74.1<br>H, 4.54<br>N, 9.9 | C, 74.3<br>H, 4.64<br>N, 9.9 | 67 |
| 85 | —CH₂CH₂OC₆H₅ | 465.51 | 123-125 | 84 | $C_{28}H_{23}N_3O_4$ | C, 72.2<br>H, 4.98<br>N, 9.02 | C, 71.7<br>H, 4.9<br>N, 9.1 | 67 |

Entire Structure Below:

| 65 | Pyridazinone with CH₂CH₂COCl substituent on N | 363.8 | ≠ | ≠ | $C_{20}H_{14}ClN_3O_2$ | C, 66.03<br>H, 3.89<br>N, 11.55 | C, ≠<br>H, ≠<br>N, ≠ | 65 |
| 69 | Pyridazinone with CF₃ replacing CN, and CH₂CH₂COOC₂H₅ on N | 341.64 | 81-83 | ≠ | $C_{22}H_{19}F_3N_2O_3$ | C, 63.5<br>H, 4.6<br>N, 6.7 | C, 63.8<br>H, 5.0<br>N, 6.7 | 67 |

TABLE V-continued

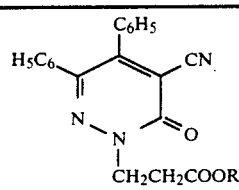

| Example Number | R | M.W. | M.P. °C. | Yield % | Formula | Calc. for | Found | Prep. |
|---|---|---|---|---|---|---|---|---|
| 68 | 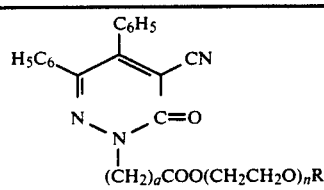 | 409.36 | 103–104 | 33 | $C_{22}H_{17}F_2N_3O_3$ | C, 68.3<br>H, 5.98<br>N, 13.8 | C, 68.1<br>H, 6.04<br>N, 13.8 | 67 |

≠ Data Not Available
The compounds in this table were prepared in accordance to the synthesis procedure of the examples represented by the numbers in this column

TABLE XXVIII

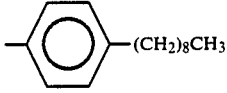

| Example Number | n | Yield % | M.P. °C. | R | a | M.W. | Formula | Calcd for | Found | Prep. No. |
|---|---|---|---|---|---|---|---|---|---|---|
| 191 | 1 | 70 | 133–135 | $C_2H_5$ | 1 | 403.40 | $C_{23}H_{21}N_3O_4$ | C, 68.4<br>H, 5.24<br>N, 10.7 | C, 68.2<br>H, 5.2<br>N, 10.7 | 33 |
| 192 | 1 | 52 | 142–144 | $C_6H_5$ | 1 | 451.44 | $C_{27}H_{21}N_3O_4$ | C, 71.8<br>H, 4.98<br>N, 9.3 | C, 71.8<br>H, 4.83<br>N, 9.23 | 33 |
| 193 | 1 | 30 | 67–71 | $C_4H_9$ | 1 | 431.25 | $C_{25}H_{25}N_3O_4$ | C, 69.6<br>H, 5.84<br>N, 9.72 | C, 69.3<br>H, 6.01<br>N, 9.82 | |
| 194 | 2 | 50 | 78 | $C_4H_9$ | 1 | 475.50 | $C_{27}H_{29}N_3O_5$ | C, 68.1<br>H, 6.17<br>N, 8.8 | C, 68.3<br>H, 6.14<br>N, 8.83 | 33 |
| 195 | 2 | 80 | oil | $-(CH_2)_5CH_3$ | 1 | 503.5 | $C_{29}H_{33}N_3O_5$ | — | — | 33 |
| 196 | 7–8 | 60 | oil | $CH_3$ | 1 | 661.00 | $C_{34}H_{43}N_3O_{10}$ | — | — | 33 |
| 197 | 11–12 | — | oil | $CH_3$ | 1 | 863.0 | $C_{42}H_{59}N_3O_{14}$ | — | — | 33 |
| 198 | 43 | — | solid | $CH_3$ | 1 | 2229.48 | $C_{106}H_{187}N_3O_{46}$ | — | — | 33 |
| 199 | 0 | — | 117–120 | * | 1 | 403.4 | $C_{23}H_{21}N_3O_4$ | C, 68.4<br>H, 5.24<br>N, 10.40 | C, 68.3<br>H, 5.2<br>N, 10.6 | 33 |
| 200 | 1–2 | — | oil | 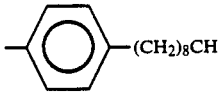 | 1 | 621.73 | $C_{38}H_{43}N_3O_5$ | — | — | 33 |
| 201 | 4 | — | oil | 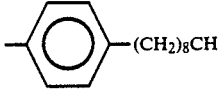 | 1 | 725.82 | $C_{42}H_{57}N_3O_7$ | | | 33 |
| 202 | 6 | — | oil | 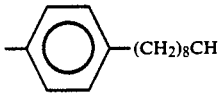 | 1 | 797.91 | $C_{46}H_{59}N_3O_9$ | — | — | 33 |
| 203 | 9 | — | oil | 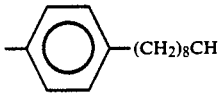 | 1 | 930.08 | $C_{52}H_{71}N_3O_{12}$ | | | 33 |

TABLE XXVIII-continued

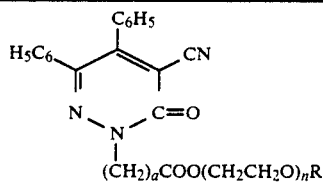

| Example Number | n | Yield % | M.P. °C. | R | a | M.W. | Formula | Calcd for | Found | Prep. No. |
|---|---|---|---|---|---|---|---|---|---|---|
| 210 | 1 | 30 | oil | $C_4H_9$ | 2 | 445.52 | $C_{26}H_{27}N_3O_4$ | | | 66 |
| 211 | 2 | 82 | oil | $C_4H_9$ | 2 | 489.53 | $C_{28}H_{31}N_3O_5$ | | | |
| 212 | 1 | 84 | 123–125 | $C_6H_5$ | 2 | 465.46 | $C_{28}H_{23}N_3O_4$ | C, 72.2  H, 4.98  N, 9.02 | C, 71.7  H, 4.90  N, 9.1 | 67 |

*Entire structure is:

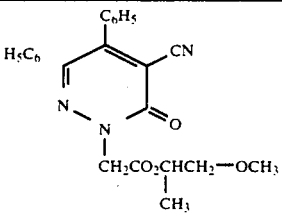

Examples 86 through 112 illustrate ester and acid derivatives of diphenylpyridazinones. These compounds are summarized in Table VI.

EXAMPLE 86

2-Methylpropionic acid, 3-(5-cyano-1,6-dihydro-6-oxo-3,4-diphenylpyridazin-1-yl) methyl ester 13.7 grams (0.05 mole) of the product of Example 1 was reacted with 5.6 grams (0.050 mole) of methyl methacrylate in 100 mls of tetrahydrofuran containing 0.25 grams of sodium hydride. This mixture was heated to reflux for 46 hours, cooled and the solvent distilled at reduced pressure. The residual oil was taken up in ethyl acetate, washed with a sodium chloride solution, separated and dried over sodium sulfate. The excess solvent was distilled at reduced pressure to give 16.7 grams (89.3%) of a crude product. This material was recrystallized from 95% ethyl alcohol to give 5.6 grams (30%) of a solid melting at 92°–94° C. The infrared spectrum showed the CN band at 4.5µ, and two carbonyl, one at 5.8µ, the other at 6.1µ.

EXAMPLE 87

Pentanoic acid, 2-(5-cyano-1,6-dihydro-6-oxo-3,4-diphenylpyridazin-1-yl) ethyl ester Example 87 is performed in accordance with that procedure set forth in Example 30.

EXAMPLE 88

1-Pyridazinecarboxylic acid, 5-cyano-1,6-dihydro-6-oxo-3,4-diphenyl methyl ester

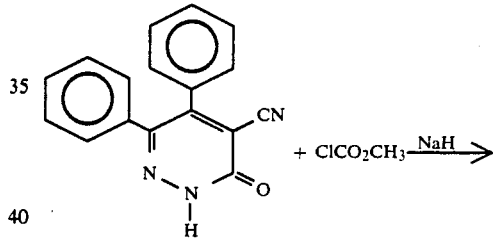

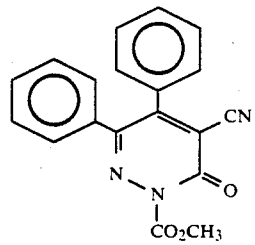

1.24 grams of 56% sodium hydride in xylene was charged to a 500 ml 3-necked flask fitted with a stirrer, thermometer, dropping funnel and a condenser with a sodium sulfate drying tube. To this flask was also added 150 mls of dry tetrahydrofuran and the mixture stirred at room temperature for one half hour. 7.0 grams (0.0256 mole) of the product of Example 1 in 50 mls of THF were added dropwise into this solution, and the mixture stirred for one hour at room temperature. 2.4 grams (0.0256 mole) methyl chloroformate was added in one portion to the solution and the mixture stirred at room temperature for 3 hours. The solvent was distilled at reduced pressure and the residual solid was taken up in ethyl acetate, washed with water, separated and the organic layer dried over $Na_2SO_4$. The solvent was distilled at reduced pressure and the crude product recrystallized from absolute ethyl alcohol to give 2.6 grams (30.6%) yield of the desired product.

EXAMPLE 89

2-Heptanoic Acid, 2-(5-cyano-1,6-dihydro-6-oxo-3,4-diphenylpyridazin-1-yl)

Example 89 is performed in accordance with that procedure set forth in Example 31.

EXAMPLE 91

2-(5-Cyano-1,6-dihydro-6-oxo-3,4-diphenylpyridazin-1-yl)-3-oximino butric acid

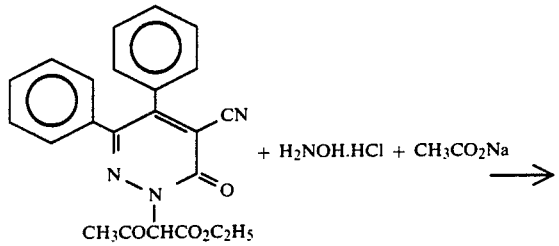

-continued

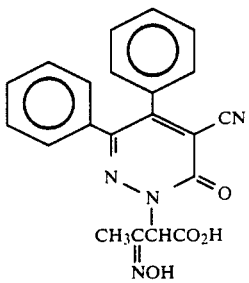

5.0 grams (0.012 mole) of the product of Example 90 was reacted with 7.5 grams (0.0877 mole) of anhydrous sodium acetate and 5.0 grams (0.071 mole) of hydroxylamine hydrochloride in 100 mls of aqueous ethyl alcohol. This mixture was heated on a hot water bath for one hour. The solvent was removed at reduced pressure by employing a rotovap and the residual liquid poured into excess hydrochloric acid and the precipitant yellow solid was filtered, washed with water and air dried. This solid was recrystallized from absolute ethyl alcohol to give 1.5 grams of a white solid melting at 162°–166° C. The infrared spectrum showed the nitrile band at 4.5μ, and two carbonyl bands, one at 5.7μ, the other at 6.0μ.

TABLE VI

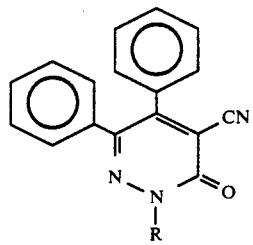

| Example Number | R | M.W. | Yield % | M.P. C°. | Formula | Calc. for | Found | Prep. |
|---|---|---|---|---|---|---|---|---|
| 86 | —CH$_2$CHCOOCH$_3$<br>$\|$<br>CH$_3$ | 382.42 | 30 | 92–94 | C$_{22}$H$_{20}$N$_3$O$_3$.5H$_2$O | C, 69.1<br>H, 5.3<br>N, 11.0 | C, 69.2<br>H, 5.3<br>N, 11.1 | 86 |
| 92 | —CH$_2$CHCOOC$_2$H$_5$<br>$\|$<br>CH$_3$ | 387.43 | 72 | 115–116 | C$_{23}$H$_{21}$N$_3$O$_3$ | C, 71.0<br>H, 5.46<br>N, 10.85 | C, 72.22<br>H, 5.34<br>N, 10.81 | 86 |
| 93 | —CH$_2$CHCOOCH$_2$CH=CH$_2$<br>$\|$<br>CH$_3$ | 399.45 | 10 | 83–85 | C$_{24}$H$_{21}$N$_3$O$_3$ | C, 72.2<br>H, 5.3<br>N, 10.5 | C, 71.6<br>H, 5.25<br>N, 10.40 | 86 |
| 94 | —(CH$_2$)$_3$COOCH$_3$ | 373.15 | 47 | 123–124 | C$_{22}$H$_{19}$N$_3$O$_3$ | C, 70.7<br>H, 5.13<br>N, 11.2 | C, 70.5<br>H, 5.14<br>N, 11.1 | 87 |
| 95 | —(CH$_2$)$_3$COOC$_2$H$_5$ | 387.39 | 62 | 114–115 | C$_{23}$H$_{21}$N$_3$O$_3$ | C, 71.3<br>H, 5.42<br>N, 10.8 | C, 70.0<br>H, 5.33<br>N, 10.6 | 87 |
| 96 | $\|$<br>CH$_3$—CHCOOC$_2$H$_5$ | 373.37 | 87 | 145–146 | C$_{22}$H$_{19}$N$_3$O$_3$ | C, 70.7<br>H, 5.12<br>N, 11.2 | C, 69.5<br>H, 5.1<br>N, 10.7 | 87 |
| 97 | $\|$<br>CH$_3$CHCOOCH$_2$CH—CH$_3$<br>CH$_3$ | 401.44 | 52 | 120–122 | C$_{24}$H$_{23}$N$_3$O$_3$ | C, 71.8<br>H, 5.8<br>N, 10.5 | C, 70.9<br>H, 5.8<br>N, 10.4 | 87 |
| 98 | $\|$<br>CH$_3$CHCOOC$_3$H$_7$ | 387.42 | 49 | 120–121 | C$_{23}$H$_{21}$N$_3$O$_3$ | C, 71.3<br>H, 5.5<br>N, 10.9 | C, 71.0<br>H, 5.5<br>N, 10.7 | 87 |

TABLE VI-continued

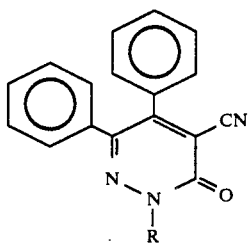

| Example Number | R | M.W. | Yield % | M.P. C° | Formula | Calc. for | Found | Prep. |
|---|---|---|---|---|---|---|---|---|
| 99 | CH$_3$CHCOO—C$_3$H$_7$(i) | 357.42 | 49 | 130–131 | C$_{23}$H$_{21}$N$_3$O$_3$ | C, 71.3<br>H, 5.5<br>N, 10.9 | C, 70.0<br>H, 5.5<br>N, 10.7 | 87 |
| 213 | CH$_3$CH—CHCOOC$_2$H$_5$<br>　　　　\|<br>　　　　CH$_3$ | 401.42 | 54 | 135–137 | C$_{24}$H$_{23}$N$_3$O$_3$ | C, 71.80<br>H, 5.77<br>N, 10.4 | C, 71.2<br>H, 5.8<br>N, 10.5 | 87 |
| 214 | CH$_3$CHCHCOOH<br>　　　\|<br>　　　CH$_3$ | 391.48 | 93 | 233 | C$_{22}$H$_{19}$N$_3$O$_3$.5H$_2$O | C, 69.2<br>H, 5.02<br>N, 11.0 | C, 69.2<br>H, 5.5<br>N, 10.6 | 89 |
| 100 | CH$_3$CH$_2$CHCOOC$_2$H$_5$ | 398.73 | 85 | 161–161 | C$_{23}$H$_{21}$N$_3$O$_3$ | C, 71.3<br>H, 5.46<br>N, 10.8 | C, 70.9<br>H, 5.35<br>N, 10.7 | 87 |
| 101 | C$_6$H$_5$CHCOOC$_2$H$_5$ | 435.44 | 34 | 166–167 | C$_{27}$H$_{21}$N$_3$O$_3$ | C, 74.4<br>H, 4.86<br>N, 9.64 | C, 74.1<br>H, 4.97<br>N, 9.6 | 87 |
| 87 | CH$_3$CH$_2$CH$_2$CHCOOC$_2$H$_5$ | 401.42 | 37 | 110–111 | C$_{24}$H$_{23}$N$_3$O$_3$ | C, 71.8<br>H, 5.77<br>N, 10.4 | C, 71.8<br>H, 5.95<br>N, 10.4 | 87 |
| 89 | CH$_3$(CH$_2$)$_4$CHCOOC$_2$H$_5$ | 414.92 | 37 | 175–181 | C$_{26}$H$_{27}$N$_3$O$_3$.¼H$_2$O | C, 69.4<br>H, 5.75<br>N, 10.1 | C, 67.6<br>H, 5.92<br>N, 10.1 | 89 |
| 102 | CH$_3$CCO$_2$C$_2$H$_5$<br>　\|<br>　CH$_3$ | 357.44 | ≠ | 150–151 | C$_{23}$H$_{21}$N$_3$O$_3$ | C, 71.3<br>H, 5.46<br>N, 10.85 | C, 70.5<br>H, 5.61<br>N, 10.71 | 87 |
| 90 | CH$_3$COCH—COC$_2$H$_5$ | 401.38 | 28 | 143 | C$_{23}$H$_{19}$N$_2$O$_4$ | C, 68.8<br>H, 4.77<br>N, 10.4 | C, 68.3<br>H, 4.75<br>N, 10.4 | 87 |
| 88 | —COOCH$_3$ | 331.3 | 31 | 165 dec. | C$_{19}$H$_{13}$N$_3$O$_3$ | C, 68.8<br>H, 3.95<br>N, 12.6 | C, 68.8<br>H, 4.0<br>N, 12.6 | 83 |
| 104 | —COOCH$_2$CH$_3$ | 345.36 | 56 | 195–196 | C$_{20}$H$_{15}$N$_3$O$_3$ | C, 69.5<br>H, 4.38<br>N, 12.2 | C, 69.5<br>H, 4.4<br>N, 12.2 | 88 |
| 105 | —COO(CH$_2$)$_2$—CH$_3$ | 395.17 | 52 | 133–135 | C$_{22}$H$_{19}$N$_3$O$_3$.¼C$_2$H$_5$OH | C, 69.1<br>H, 5.0<br>N, 11.0 | C, 65.7<br>H, 5.0<br>N, 11.0 | 88 |
| 215 | CH$_2$CH=CH—COOC$_2$H$_5$ | 385.38 | 20 | 225 | C$_{23}$H$_{19}$N$_3$O$_3$ | C, 71.6<br>H, 4.96<br>N, 12.3 | C, 71.48<br>H, 4.97<br>N, 10.00 | 87 |
| 216 | CH$_2$C(CH$_3$)$_2$—CO$_2$H | 373.41 | 30 | 220–222 | C$_{22}$H$_{19}$N$_3$O$_3$ | C, 70.8<br>H, 5.1<br>N, 11.3 | C, 70.4<br>H, 5.1<br>N, 11.3 | * |
| 217 | NCCHCH$_2$COOC$_2$H$_5$ | 398.42 | 28 | 239 | C$_{23}$H$_{18}$N$_4$O$_3$ | C, 69.3<br>H, 4.6<br>N, 14.1 | C, 69.5<br>H, 4.5<br>N, 4.6 | 67 |
| 218 | CH=CH—CO$_2$C$_2$H$_5$ | 371.39 | 20 | 175–176 | C$_{22}$H$_{17}$N$_3$O$_3$ | C, 71.1<br>H, 4.6<br>N, 11.7 | C, 70.7<br>H, 4.7<br>N, 11.0 | 67 |

TABLE VI-continued

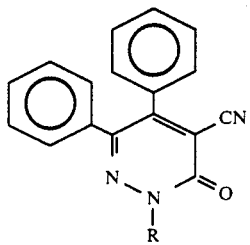

| Example Number | R | M.W. | Yield % | M.P. C°. | Formula | Calc. for | Found | Prep. |
|---|---|---|---|---|---|---|---|---|
| 32 | $\overset{\mid}{C}H_2\overset{\mid}{C}OCH$ | 331.28 | 81 | 235 | $C_{19}H_{13}N_3O_3$ | C, 68.8<br>H, 3.95<br>N, 12.6 | C, 68.7<br>H, 3.73<br>N, 12.6 | 32 |
| 65 | $\overset{\mid}{C}H_2CH_2COOH$ | 345.31 | 83 | 185–187 | $C_{20}H_{15}N_3O_3$ | C, 69.5<br>H, 4.37<br>N, 12.2 | C, 69.0<br>H, 4.37<br>N, 12.3 | 65 |
| 106 | —$CH_2CH_2CH_2$—COOH | 377.34 | 92 | 193 | $C_{21}H_{17}N_3O_3 \cdot H_2O$ | C, 67.0<br>H, 5.0<br>N, 11.1 | C, 67.7<br>H, 4.7<br>N, 11.2 | 89 |
| 107 | $CH_3-\overset{\mid}{C}H-COOH$ | 345.32 | 76 | 243 | $C_{20}H_{15}N_3O_3$ | C, 69.5<br>H, 4.4<br>N, 12.0 | C, 68.5<br>H, 4.31<br>N, 12.2 | 89 |
| 108 | $CH_3CH_2\overset{\mid}{C}H-COOH$ | 359.29 | 100 | 219 | $C_{24}H_{17}N_3O_3$ | C, 70.1<br>H, 4.79<br>N, 11.6 | C, 69.9<br>H, 5.81<br>N, 11.6 | 89 |
| 110 | $\overset{\mid}{C}HCOOH$<br>$\mid$<br>$CH_2CH_2CH_3$ | 391.37 | 54 | 150 dec. | $C_{22}H_{19}N_3O_3 \cdot H_2O$ | C, 67.6<br>H, 5.1<br>N, 10.6 | C, 67.5<br>H, 5.4<br>N, 10.7 | 89 |
| 91 | $CH_3\overset{\mid}{C}CHCOOH$<br>$\parallel$<br>$NCH$ | 388.34 | ≠ | 162– | $C_{21}H_{16}N_4O_4$ | C, 65.0<br>H, 4.15<br>N, 14.4 | C, 65.4<br>H, 3.9<br>N, 14.3 | 89 |
| 111 | $\overset{\mid}{C}H_2-\overset{\mid}{C}HCOOH$<br>$\mid$<br>$CH_3$ | 359.34 | 70 | 191–192 | $C_{21}H_{17}N_3O_3$ | C, 70.1<br>H, 4.76<br>N, 11.6 | C, 69.6<br>H, 4.77<br>N, 11.8 | 89 |
| 103 | Entire Structure Below:<br>p-Cl—H₅C₆ group with C₆H₅—p-Cl, CN, N—N, =O, (CH₂)₃COOC₂H₅ | 456.31 | ≠ | 115–117 | $C_{23}H_{19}Cl_2N_3O_3$ | C, 60.5<br>H, 4.2<br>N, 9.4 | C, 60.3<br>H, 4.2<br>N, 9.3 | 87 |
| 109 | C₆H₅, H₂C₆, CO₂H, N—N, =O, CH₂CO₂H | 350.33 | ≠ | 213–214 | $C_{19}H_{14}N_2O_5$ | C, 65.4<br>H, 4.02<br>N, 7.99 | C, ≠<br>H, ≠<br>N, ≠ | 89 |

TABLE VI-continued

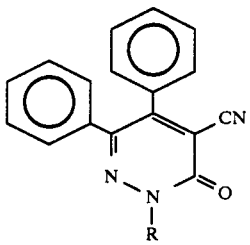

| Example Number | R | M.W. | Yield % | M.P. C°. | Formula | Calc. for | Found | Prep. |
|---|---|---|---|---|---|---|---|---|
| 112 | p-F—H$_5$C$_6$ , C$_6$H$_5$—p-F (structure with CH$_2$CH$_2$COOH) | 381.34 | 57 | 182–185 | C$_{20}$H$_{13}$F$_2$N$_3$O$_3$ | C, 62.4<br>H, 3.4<br>N, 11.0 | C, 62.5<br>H, 3.4<br>N, 11.3 | 64 |

≠ Data Not Available

The compounds in this table were prepared in accordance to the synthesis procedure set forth in the examples represented by the numbers in this column Examples 113 through 134 illustrate various salt derivatives of diphenylpyridazinones. These compounds are summarized in Table VII.

EXAMPLE 113

Potassium salt of 3-(5-cyano-1,6-dihydro-6-oxo-3,4-diphenylpyridazin-1-yl) propionic acid 5.0 grams (0.0144 mole) of the product of Example 64 was reacted with 2.1 grams (0.0152 mole) of potassium carbonate in 50 mls of distilled water. This solution was heated on a steam bath for 10 minutes, cooled and the solvent distilled at reduced pressure. There was isolated 6.2 grams (88%) yield of a yellow solid which melted at 220° C. with decomposition.

EXAMPLE 114

Cis-2,5-dimethylpyrrolidine salt of 5-cyano-1,6-dihydro-6-oxo-3,4-diphenylpyridazin-1-yl acetic acid

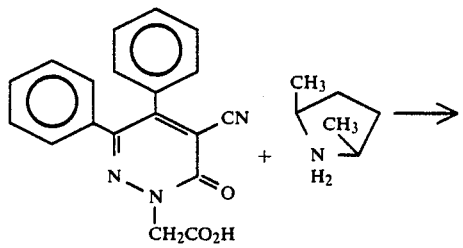

-continued

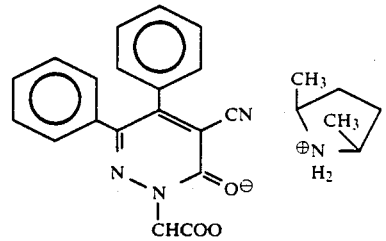

10 grams (0.030 mole) of the product of Example 31 was reacted with 3.0 grams (0.030 mole) of Cis-2,5-dimethylpyrrolidine in 10 mls of dry benzene. This solution was heated on a steam bath for one hour. The solvent was distilled at reduced pressure and the residual solid filtered, washed with petroleum ether and air dried. There was isolated a quantative yield of crude product.

TABLE VII

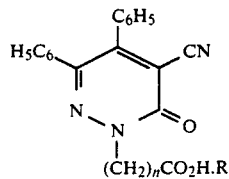

| Example Number | R | M.W. | n | Yield % | M.P. C°. | Formula | Calc. for | Found | Prep. |
|---|---|---|---|---|---|---|---|---|---|
| 114 Cis | CH₃ / CH₃ pyrrolidine NH | 430.00 | 1 | 83 | 169 dec. | C₂₅H₂₆N₄O₃ | C, 69.7<br>H, 6.1<br>N, 13.0 | C, 69.2<br>H, 6.2<br>N, 13.4 | 114 |
| 115 | HN—(CHCH₃—CH₃)₂ | 432.47 | 1 | 100 | 180 | C₂₅H₂₈N₄O₃ | C, 69.4<br>H, 6.52<br>N, 13.0 | C, 69.4<br>H, 6.7<br>N, 13.1 | 114 |
| 116 Cis | CH₃ / CH₃ pyrrolidine NH | 449.49 | 2 | 69 | 164–166 | C₂₆H₂₈N₄O₃ | C, 70.2<br>H, 6.75<br>N, 12.5 | C, 69.9<br>H, 6.35<br>N, 12.6 | 114 |
| 117 Cis | CH₃ / CH₃ pyrrolidine NH | 458.48 | 3 | 73 | 160 | C₂₀H₁₅N₃O₂ | C, 72.9<br>H, 4.59<br>N, 12.2 | C, 72.0<br>H, 4.58<br>N, 12.7 | 114 |
| 118 | morpholine (HN, O) | 432.40 | 2 | 70 | 144–145 | C₂₄H₃₄N₄O₄ | C, 66.6<br>H, 5.60<br>N, 12.9 | C, 65.9<br>H, 5.5<br>N, 12.7 | 114 |
| 119 | HN—piperazine—NCH₃ | 463.46 | 2 | 71 | 141–143 | C₂₅H₂₇N₅O₃·H₂O | C, 64.8<br>H, .30<br>N, 15.1 | C, 65.5<br>H, 6.05<br>N, 15.3 | 114 |
| 120 | HN(CH₂CH₂OH)₂ | 450.45 | 2 | 62 | 132–134 | C₂₄H₂₆N₄O₅ | C, 63.9<br>H, 5.81<br>N, 12.4 | C, 63.4<br>H, 5.86<br>N, 12.2 | 114 |
| 121 | 2,6-dimethylpiperidine (CH₃, HN, CH₃) | 444.18 | 1 | 76 | 175–176 | C₂₆H₂₈N₄O₃ | C, 70.0<br>H, 6.30<br>N, 12.7 | C, 69.7<br>H, 6.5<br>N, 12.2 | 114 |
| 122 | pyrrolidine (NH) | 402.40 | 1 | 80 | 179–180 | C₂₃H₂₂N₄O₃ | C, 68.5<br>H, 5.5<br>N, 12.8 | C, 68.3<br>H, 5.5<br>N, 12.1 | 114 |
| 123 | piperidine (HN) | 430.46 | 2 | 76 | 161–163 | C₂₅H₂₆N₄O₃ | C, 69.7<br>H, 6.08<br>N, 13.0 | C, 68.1<br>H, 6.1<br>N, 13.0 | 114 |
| 124 | HN(CH₂CH₂OH)₂ | 436.42 | 1 | 49 | 157–158 | C₂₃H₂₄N₄O₅ | C, 63.5<br>H, 5.5<br>N, 12.8 | C, 62.8<br>H, 5.6<br>N, 12.1 | 114 |

TABLE VII-continued

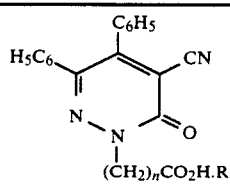

| Example Number | R | M.W. | n | Yield % | M.P. C° | Formula | Calc. for | Found | Prep. |
|---|---|---|---|---|---|---|---|---|---|
| 125 | HN⟨cyclohexyl⟩ | 416.43 | 1 | 80 | 179–180 | $C_{24}H_{24}N_4O_3$ | C, 69.0<br>H, 5.75<br>N, 13.5 | C, 68.9<br>H, 5.88<br>N, 13.4 | 114 |
| 219 | $NH_2(CH_2)_3CH_3$ | 413.43 | 1 | 50 | 197 | $C_{23}H_{24}N_4O_3\cdot\frac{1}{2}H_2O$ | C, 66.8<br>H, 5.98<br>N, 13.8 | C, 66.7<br>H, 6.10<br>N, 13.60 | 114 |
| 220 | $(CH_3)_2NCH_2CH_2OH\cdot\frac{1}{2}H_2O$ | 429.31 | 1 | 49 | 128–131 | $C_{23}H_{24}N_4O_4\cdot\frac{1}{2}H_2O$ | C, 64.4<br>H, 5.8<br>N, 13.0 | C, 64.4<br>H, 5.8<br>N, 13.2 | 114 |
| 126 | HN⟩NCH$_2$CH$_2$OH | 461.46 | 1 | 52 | 156 | $C_{25}H_{27}N_5O_4$ | C, 65.0<br>H, 5.85<br>N, 15.3 | C, 64.5<br>H, 6.03<br>N, 15.2 | 114 |
| 127 | HN⟨cycloheptyl⟩ | 430.45 | 1 | 86 | 175–176 | $C_{26}H_{26}N_4O_3$ | C, 70.0<br>H, 6.05<br>N, 13.0 | C, 69.6<br>H, 6.2<br>N, 13.0 | 114 |
| 128 | O⟩NCH$_2$CH$_2$OH | 462.46 | 1 | 76 | 155–156 | $C_{25}H_{26}N_4O_5$ | C, 65.0<br>H, 5.6<br>N, 12.1 | C, 64.5<br>H, 5.75<br>N, 12.1 | 114 |
| 129 | 2,6-dimethylpiperidinyl (HN, CH$_3$, CH$_3$) | 472.54 | 3 | 57 | 178– | $C_{28}H_{24}N_4O_3$ | C, 71.1<br>H, 6.83<br>N, 11.6 | C, 70.6<br>H, 6.04<br>N, 11.6 | 114 |
| 130 | $HN(C_2H_5)_2$ | 404.68 | 1 | 100 | 185 | $C_{23}H_{24}N_4O_3$ | C, 68.3<br>H, 5.98<br>N, 13.8 | C, 68.1<br>H, 6.04<br>N, 13.8 | 114 |
| 131 | NH—CH$_3$C(Cl)=CH$_2$<br>HC(CH$_2$)$_2$ | 469.91 | 1 | 100 | 143– | $C_{25}H_{25}Cl_1N_4O_3$ | C, 64.5<br>H, 5.42<br>N, 12.0 | C, 63.9<br>H, 5.46<br>N, 11.96 | 114 |
| 132 | Na | 354.32 | 1 | ≠ | ≠ | $C_{19}H_{13}N_3O_3Na$ | C, 64.41<br>H, 3.7<br>N, 11.86 | ≠ | 113 |
| 133 | Na | 368.35 | 2 | ≠ | ≠ | $C_{20}H_{15}N_3O_3Na$ | C, 65.21<br>H, 4.1<br>N, 11.41 | ≠ | 113 |
| 134 | $NH_4$ | 349.37 | 1 | ≠ | ≠ | $C_{19}H_{17}N_4O_3$ | C, 65.32<br>H, 4.9<br>N, 16.04 | ≠ | 113 |
| 113 | K | 369.31 | 2 | 100 | 221 dec | $C_{20}H_{15}N_3O_3K$ | C, 65.04<br>H, 3.82<br>N, 11.7 | ≠ | 113 |

≠ Data Not Available
The compounds in this table were prepared in accordance to the synthesis procedure of the examples represented by the numbers in this column.

Examples 135 through 147 illustrate amide derivatives of diphenylpyridazinones. These compounds are summarized in Table VIII.

EXAMPLE 135

N-methyl-3,4-diphenyl-5-cyano-6-oxo-1,6-dihydropyridazin-1-yl-acetamide

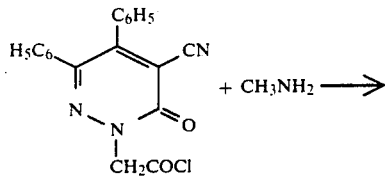 + CH₃NH₂ ⟶

Excess methyl amine was bubbled into 100 mls of dry benzene. 7.0 grams (0.002 mole) of the product of Example 32 in 50 mls of benzene was added dropwise into this solution. The solution was then heated to reflux for 2 hours, cooled and the solid filtered. The filtrate was distilled at reduced pressure and the residual solid was recrystallized from ethyl alcohol to give 3.4 grams (50% yield) of a material melting at 292°–294° C.

EXAMPLE 136

2-(3,4-diphenyl-5-cyano-6-oxo-1,6-dihydropyridazine-1-yl)propionic acid chloride Example 136 is performed in accordance with that procedure set forth in Example 32.

EXAMPLE 137

2-(N,N-dimethylcarbamyl)-4-cyano-5,6-diphenyl-3-(2H)-pyridazinone

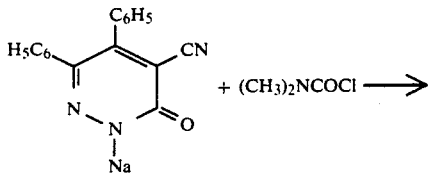 + (CH₃)₂NCOCl ⟶

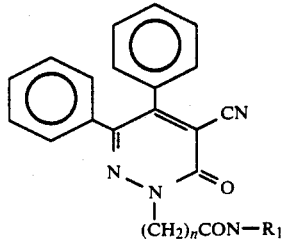

5.0 grams (0.016 mole) of the sodium salt of 4-cyano-5,6-diphenyl-3-(2H)-pyridazinone was reacted with 1.83 grams (0.017 mole) of dimethylcarbamyl chloride in 50 mls of dimethylformamide. This solution was heated 110° C. for 3 hours, cooled, and poured into excess water. The precipitant solid was filtered, washed with water and air dried. This solid was taken up in chloroform, dried over sodium sulfate and the solvent distilled at reduced pressure. The residual solid was recrystallized from ethyl alcohol to give 3.0 grams of a solid which melted at 231° C. The infrared spectrum showed the methyl group at 3.5μ, the nitrile band at 4.5μ, and two carbonyl bands at 5.8 and 6.0μ.

EXAMPLE 138

3,4-Diphenyl-5-cyano-6-oxo-1,6-dihydropyridazin-1-yl acetic acid hydrazide 15.0 grams (0.0417 mole) of the product of Example 30 was reacted with 5.0 grams of 90% hydrazine hydrate in 100 mls of ethyl alcohol. This solution was heated to reflux for 5 hours and cooled. The precipitant solid was filtered, washed with pet ether and air dried. This solid was recrystallized from benzene to give 10.0 grams (69.4%) yield of a solid melting at 191°–192° C.

TABLE VII

| Example Number | n | R | R₁ | M.W. | Yield % | M.P. C | Formula | Calc For | | Found | | Prep++ |
|---|---|---|---|---|---|---|---|---|---|---|---|---|
| 139 | 2 | —CH₃ | —CH₃ | 372.24 | 75 | 166 | C₂₂H₂₀N₄O₂ | C, | 70.0 | C, | 70.1 | 135 |
| | | | | | | | | H, | 5.4 | H, | 5.37 | |
| | | | | | | | | N, | 15.0 | N, | 14.7 | |
| 140 | 1 | —H | —H | 330.33 | 50 | 225–226 | C₁₉H₁₄N₄O₂ | C, | 69.1 | C, | 69.0 | 135 |

TABLE VII-continued

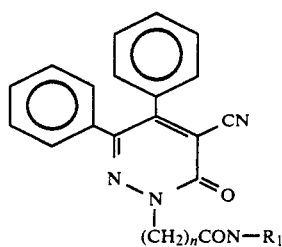

$(CH_2)_n CON-R_1$

| Example Number | n | R | $R_1$ | M.W. | Yield % | M.P. C | Formula | Calc For | | Found | | Prep++ |
|---|---|---|---|---|---|---|---|---|---|---|---|---|
| | | | | | | | | H, | 4.3 | H, | 4.4 | |
| | | | | | | | | N, | 16.9 | N, | 17.2 | |
| 141 | 1 | —H | —$C_3H_7$—i' | 372.41 | 60 | 185–186 | $C_{22}H_{20}N_4O_2$ | C, | 70.0 | C, | 69.6 | 135 |
| | | | | | | | | H, | 5.4 | H, | 5.5 | |
| | | | | | | | | N, | 15.1 | N, | 14.8 | |
| 135 | 1 | —H | —$CH_3$ | 344.36 | 49 | 293–294 | $C_{20}H_{16}N_4O_2$ | C, | 69.7 | C, | 70.0 | 135 |
| | | | | | | | | H, | 4.68 | H, | 4.6 | |
| | | | | | | | | N, | 16.3 | N, | 16.7 | |
| 142 | 1 | —$CH_3$ | —$CH_3$ | 358.36 | 70 | 257–258 | $C_{21}H_{18}N_4O_2$·$C_2H_5OH$ | C, | 68.3 | C, | 68.7 | 135 |
| | | | | | | | | H, | 5.9 | H, | 6.1 | |
| | | | | | | | | N, | 13.8 | N, | 14.3 | |
| 143 | 2 | —H | —$CH_3$ | 358.38 | 100 | 185–187 | $C_{21}H_{18}N_4O_2$ | C, | 70.3 | C, | 69.0 | 135 |
| | | | | | | | | H, | 5.06 | H, | 4.99 | |
| | | | | | | | | N, | 15.6 | N, | 15.2 | |
| 144 | 2 | —H | —H | 344.32 | 40 | 185–186 | $C_{20}H_{16}N_4O_2$ | C, | 69.7 | C, | 69.5 | 135 |
| | | | | | | | | H, | 4.68 | H, | 4.62 | |
| | | | | | | | | N, | 16.2 | N, | 16.0 | |
| 145 | 1 | —H | —$CH_2CH_2CH_3$ | 374.35 | ≠ | ≠ | $C_{21}H_{18}N_4O_3$ | C, | 67.37 | | ≠ | 135 |
| | | | | | | | | H, | 4.54 | | ≠ | |
| | | | | | | | | N, | 14.95 | | ≠ | |
| 146 | 1 | —$CH_2CH_2CH$ —$CH_2CH_2CH$ | | 415.41 | ≠ | ≠ | $C_{23}H_{22}N_4O_4$ | C, | 66.0 | | ≠ | 135 |
| | | | | | | | | H, | 5.3 | | ≠ | |
| | | | | | | | | N, | 13.35 | | ≠ | |

Entire Structure Below:

| 147 | * | $C_6H_5$, $H_5C_6$, CH, N-N, CH$_3$CHCONHCH$_3$ | 358.38 | 62 | ≠ | $C_{21}H_{18}N_4O_2$ | C, 70.4 C, 71.4 | 135 |
|---|---|---|---|---|---|---|---|---|
| | | | | | | | H, 5.1 H, 5.5 | |
| | | | | | | | N, 15.6 N, 14.3 | |
| 137 | * | $C_6H_5$, $H_5C_6$, CH, N-N, CON(CH$_3$)$_2$ | 344.31 | 52 | 231 | $C_{20}H_{16}N_4O_2$ | C, 69.7 C, 69.2 | 137 |
| | | | | | | | H, 4.65 H, 4.7 | |
| | | | | | | | N, 16.2 N, 15.9 | |
| 138 | * | $C_6H_5$, $H_5C_6$, CN, N-N, CH$_2$CONHNH$_2$ | 345.36 | 70 | 194–197 | $C_{19}H_{15}N_5O_2$ | C, 66.08 C, 66.0 | 138 |
| | | | | | | | H, 4.31 H, 4.24 | |
| | | | | | | | N, 20.27 N, 20.16 | |
| 136 | * | $C_6H_5$, $H_5C_6$, CN, N-N, H$_3$CCHCOCl | 363.8 | ≠ | ≠ | $C_{20}H_{14}N_3O_2Cl$ | C, 66.04 C, ≠ | 136 |
| | | | | | | | H, 3.88 H, ≠ | |
| | | | | | | | N, 11.55 N, ≠ | |
| 221 | 2 | H | CH$_2$OCH$_2$ | 430.41 | 40 | 107–110 | $C_{25}H_{26}N_4O_3$ | C, 69.7 C, 70.0 | 135 |

TABLE VII-continued

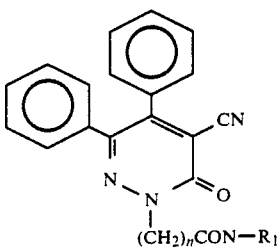

| Example Number | n | R | R₁ | M.W. | Yield % | M.P. C | Formula | Calc For | Found | Prep++ |
|---|---|---|---|---|---|---|---|---|---|---|
| 222 | 1 | H | CHCH₃ \| CH —(CH₂)₃CH₃ | 386.40 | 30 | 178 | $C_{23}H_{22}N_4O_2$ | H, 6.08  N, 13.0  C, 71.5  H, 5.73  N, 14.4 | H, 6.2  N, 13.6  C, 71.3  H, 5.8  N, 14.4 | 135 |

*Not Applicable
= Data Not Available
++ The compounds in this table were prepared in accordance to the synthesis procedure of the examples represented by the numbers in this column.

Examples 148 through 157 illustrate carbamate derivatives of diphenylpyridazinones. These compounds are summarized in Table IX.

EXAMPLE 148

N-phenylcarbamate of the 2-hydroxy ethylester of 5-cyano-1,6-dihydro-6-oxo-3,4-diphenylpyridazin-1-yl propionic acid

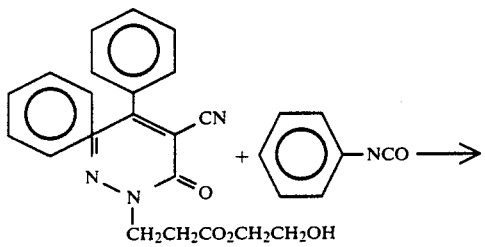

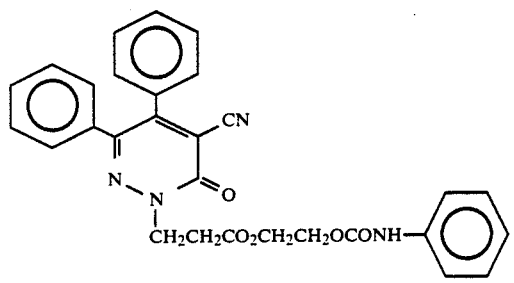

6.6 grams (0.016 mole) of the product of Example 71 was reacted with 2.02 grams (0.016 mole) of phenyl isocyanate in 60 mls of dry toluene. This solution was heated on a steam bath for 1 hour. The precipitant was filtered, washed with petroleum ether and air dried. There was isolated 8.6 grams (100%) yield of a yellow solid that melted at 154°-155° C. The infrared spectrum showed the NH band at 3.1, the nitrile band at 4.5μ, and two carbonyl bands, one at 5.8μ, the other at 6.1μ.

EXAMPLE 149

N-phenylcarbamate of 2-(2'-hydroxyethyl)-4-cyano-5,6-diphenyl-3-(2H)-pyridazinone 6.0 grams (0.02 mole) of 2-(2'-hydroxyethyl)-5,6-diphenyl-4-cyano-3-(2H)-pyridazinone was reacted with 2.3 grams (0.02 mole) of 2-chloroethylisocyanate in 30 mls of tetrahydrofuran. The solution was heated to reflux for 3 hours, cooled and the solvent distilled at reduced pressure. The crude solid was recrystallized from acetonitrile to give 3 grams (36%) yield of a solid which melted at 228°-229° C. The infrared spectrum showed the NH band at 3.0μ and two carbonyl bands, one at 5.8μ and the other at 5.9μ.

TABLE IX

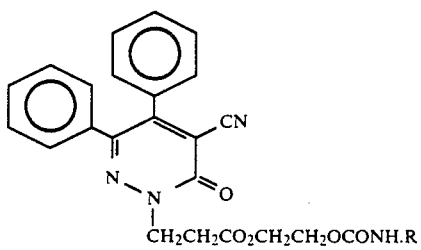

| Example Number | R | M.W. | Yield % | M.P. C° | Formula | Calc. for | | Found | | Prep.++ |
|---|---|---|---|---|---|---|---|---|---|---|
| 148 | -phenyl | 508.49 | 100 | 154–155 | $C_{29}H_{24}N_4O_5$ | C, 68.4<br>H, 4.75<br>N, 11.0 | | C, 68.4<br>H, 4.8<br>N, 11.1 | | 148 |
| 150 | —CH₃ | 446.46 | 76 | oil | $C_{24}H_{22}N_4O_5$ | C, 64.6<br>H, 5.0<br>N, 12.6 | | C, 65.0<br>H, 5.3<br>N, 12.4 | | 148 |
| 151 | 4-F-phenyl | 526.45 | 82 | 140 | $C_{29}H_{23}FN_4O_5$ | C, 66.2<br>H, 4.4<br>N, 10.7 | | C, 66.6<br>H, 4.7<br>N, 10.7 | | 148 |
| 152 | 4-Cl-phenyl | 542.93 | 90 | 131–132 | $C_{29}H_{23}Cl_1N_4O_5$ | C, 64.1<br>H, 4.26<br>N, 10.39 | | C, 64.1<br>H, 4.3<br>N, 10.4 | | 148 |
| 153 | —CH₂CH₂Cl | 494.58 | 48 | oil | $C_{25}H_{23}Cl_1N_4O_5$ | C, 60.6<br>H, 4.68<br>N, 11.3 | | C, 60.3<br>H, 4.8<br>N, 11.5 | | 148 |
| 154 | 4-C₆H₅-phenyl | 520.53 | 67 | 138 | $C_{31}H_{28}N_4O_4$ | C, 69.3<br>H, 5.26<br>N, 10.4 | | C, 69.0<br>H, 5.2<br>N, 10.3 | | 148 |
| 155 | 3-CH₃-phenyl | 522.54 | 73 | 141 | $C_{30}H_{26}N_4O_5$ | C, 68.9<br>H, 5.01<br>N, 10.75 | | C, 68.9<br>H, 5.02<br>N, 10.72 | | 148 |
| 156 | 3-CF₃-phenyl | 576.48 | 32 | 115–117 | $C_{30}H_{23}F_3N_4O_5$ | C, 62.5<br>H, 4.02<br>N, 9.7 | | C, 62.5<br>H, 4.14<br>N, 9.4 | | 148 |

In the compounds shown below, "R" is attached directly to the 2-nitrogen of the 4-cyano-5,6-diphenyl-3-pyridazinone structure.

| | | | | | | | | | | |
|---|---|---|---|---|---|---|---|---|---|---|
| 149 | —CH₂CH₂O—<br>—CONH—C₆H₅ | 436.42 | 36 | 228–229 | $C_{26}H_{20}N_4O_3$ | C, 71.5<br>H, 4.61<br>N, 12.8 | | C, 71.1<br>H, 4.69<br>N, 12.9 | | 149 |
| 157 | —CH₂CH₂O—<br>—CONHCH₂CH₂Cl | 422.87 | ≠ | 127–128 | $C_{22}H_{19}Cl_1N_4O_3$ | C, ≠<br>H, ≠<br>N, ≠ | | C, ≠<br>H, ≠<br>N, ≠ | | 149 |

≠ Data Not Available
++ The compounds in this table were prepared in accordance to the synthesis procedure of the examples represented by the numbers in this column.

Examples 158 through 173 illustrate selected cyclic amino, dithiocarbamate, ether, mercapto, nitrate and sulfonyl derivatives of diphenylpyridazinones. These compounds are summarized in Table X.

EXAMPLE 158

2-(2'-Ethoxyethyl)-4-cyano-5,6-diphenyl-3-(2H)-pyridazinone

Example 158 is performed in accordance with that procedure set forth in Example 9. The appropriate chlorester was used in Example 158 rather than the chloroalcohols used in Example 9.

EXAMPLE 159

2-(2'-Cyanoethyl)-4-cyano-5,6-diphenyl-3-(2H)-pyridazinone 4.0 grams (0.0146 mole) of 4-cyano-5,6-diphenyl-3-(2H)-pyridazinone was dissolved in 40 mls of pyridine along with 10 mls of distilled water. 2 mls of acrylonitrile was added into this solution and the mixture heated to reflux for 2 hours. The solution was cooled and the solvent distilled at reduced pressure. The residual solid was recrystallized from ethyl alcohol to give 2 grams (42%) yield of a white solid which melted at 160°–161° C. The infrared spectrum showed the C-C band at 3.3$\mu$, the nitrile group at 4.5$\mu$, and the carboxy groups for an amide at 6.0$\mu$.

EXAMPLE 160

2-(Cyanomethyl)-4-cyano-5,6-diphenyl-3-(2H)-pyridazinone 15 grams (0.0508 mole) of the sodium salt from Example 8 was reacted with 3.83 grams (0.0508 mole) chloroacetonitrile in 60 mls of dimethylformamide. This solution was heated to 110° C. for 4 hours, cooled and the solvent distilled at reduced pressure. The residual solid was recrystallized from ethyl alcohol to give 5.8 grams (54%) yield of a solid melting a 197° C. The infrared spectrum showed the nitrile band at 4.4$\mu$, the carbonyl band at 5.96$\mu$.

EXAMPLE 161

2-(2-Diethylaminoethyl)-4-cyano-5,6-diphenyl-3-(2H)-pyridazinone 2 grams (0.0067 mole) of the sodium salt from Example 8 was reacted with 1.0 grams (0.0073 mole) of diethylaminoethyl chloride in 10 mls of dimethylformamide. The mixture was heated in a hot water bath at 95.97° C. for 20 minutes. The reaction mixture was then poured into 100 mls of water and the solution extracted with ethyl ether, filtered and dried over sodium sulfate. The dry reagent was removed by filtration and the solvent distilled at reduced pressure. There was isolated 1.6 grams (63.4%) yield of a solid. This solid was washed with cold hydrochloric acid, dried and recrystallized from absolute ethyl alcohol.

EXAMPLE 162

2-Cis-2,5-dimethylpyrrolidin-1-ylmethyl-4-cyano-5,6-diphenyl-3-(2H)-pyridazinone

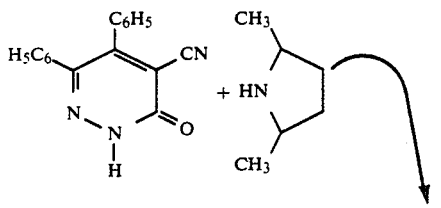

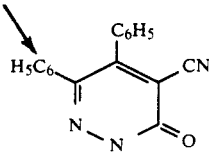

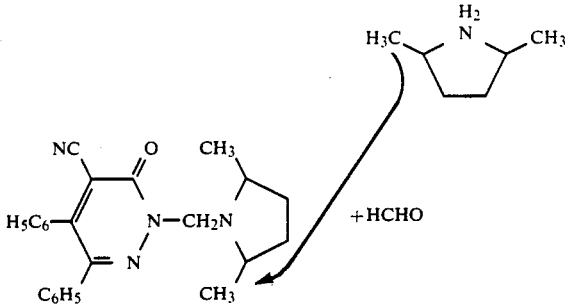

+HCHO

The salt (I) was prepared from the reaction of 2.13 grams (0.021 mole) of Cis-2,5-dimethylpyrrolidine 99% Cis isomer and 5.9 grams of the product of Example 1 in 100 mls of aqueous ethyl alcohol. Into this solution was added 4.0 grams of 40% aqueous formaldehyde. This mixture was heated on a steam bath for 20 minutes. The excess solvent was distilled at reduced pressure and the residual yellow solid was recrystallized from absolute ethyl alcohol to give 4.0 grams (57.8%) of a solid that melted at 156° C.

EXAMPLE 163

2-(2'-Ethylsulfonylethyl)-4-cyano-5,6-diphenyl-3-(2H)-pyridazinone 8.0 grams (0.0175 mole) of the product of Example 1 was reacted with 2.1 grams of ethyl-vinyl sulfone in 60 mls of pyridine. This solution was heated on a steam bath for 2 hours, cooled and the solvent distilled at reduced pressure. The residual oil was taken up in ethyl alcohol. 5.0 grams (72% yield) of a solid precipitated and was filtered, washed with petroleum ether and air dried. The infrared spectrum showed the nitrile band at 4.5$\mu$, the carbonyl band at 6.0$\mu$, the SO$_2$ band at 8.7$\mu$.

EXAMPLE 164

2-(2'-Nitrobutyl)-4-cyano-5,6-diphenyl-3-(2H)-pyridazinone 4.0 grams (0.014 mole) of the product of Example 1 was reacted with 2.37 grams (0.014 mole) of 2-nitrobutyl acetate in 100 mls of dry pyridine. This solution was heated to reflux for 1 hour, cooled and the solvent distilled at reduced pressure. The residual solid was recrystallized from methyl alcohol to give 2.0 grams (37% yield) of a white-yellow solid melting at 154°–155° C. The infrared spectrum showed the C-C band at 3.5$\mu$, the nitrile band at 4.5$\mu$, and the amide carbonyl band at 6.0$\mu$.

EXAMPLE 165

2-(N,N-dimethyldithiocarbamylethyl)-4-cyano-5,6-diphenylpyridazinone

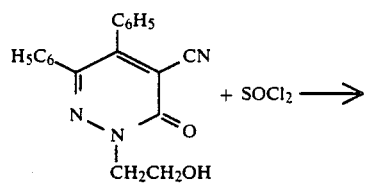

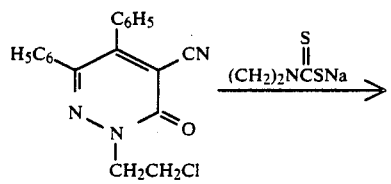

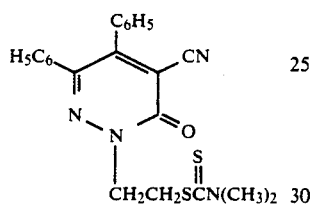

15.0 grams (0.0472 mole) of the product of Example 8 was reacted with 6.2 grams (0.052 mole) of thionyl chloride in 80 mls of DMF. This mixture was heated to 110° C. for 3 hours, cooled and the solvent distilled at reduced pressure. The residual oil was taken up in ethyl acetate, filtered and the filtrate dried over Na₂SO₄. The drying reagent was removed by filtration and the solvent distilled at reduced pressure. The residual oil was taken up in 100 mls of THF. Then 6.78 grams (0.0473 mole) of the sodium salt of N,N-dimethyldithiocarbamic acid was added and the mixture heated to reflux for 3 hours. The solution was cooled and the sodium salt filtered. The filtrate was distilled at reduced pressure and the residual solid recrystallized from absolute ethyl alcohol to give 11.94 grams, a 60% yield, of a solid melting at 155° C.

EXAMPLE 166

Malonic acid, 5-cyano-1,6-dihydro-6-oxo-3,4-diphenylpyridazin-1-yl diethyl ester 59.0 g (0.20 moles) of the product of Example 6 in 170 ml of DMF was charged to a 500 ml, 3-neck flask fitted with a mechanical stirrer, a thermometer, and a condenser with a CaSO₄ filled drying tube.

39.0 g (0.20 moles) of diethylchloromalonate was added to the above. The entire mixture was stirred at 100°-105° C. for 5.5 hours. Then the NaCl precipitate was suction filtered and the filtrate was concentrated in vacuo by using a rotovap and steam bath.

The resulting viscous, red oil was dissolved in 600 ml of ethyl acetate and washed with saturated NaCl solution. This was dried through Na₂SO₄ and the solvent removed in vacuo to give 69.5 g of a viscous, amber oil. When titurated with absolute ethanol, this oil became a solid. This solid was then recrystallized from absolute ethanol to yield 36.2 grams of Malonic acid, 5-cyano-1,6-dihydro-6-oxo-3,4-diphenylpyridazin-1-yl diethyl ester.

EXAMPLE 230

2-(5-Cyano-3,4-diphenyl-6-oxo-1,6-dihydropyridazin-1-yl) ethyl sulfonic acid hydrate

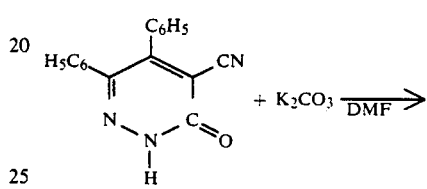

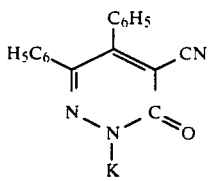

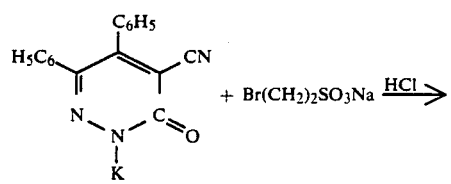

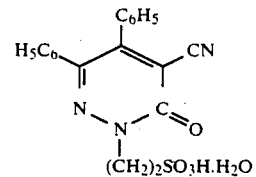

7.5 grams (0.027 mole) of the product of Example 1 was caused to react with 3.79 grams of K₂CO₃ in the least amount of water along with 200 mls of DMF. To this mixture was added 5 drops of 18 crown-6-ether. Into this solution was added 5.79 grams (0.027 mole) of 2-bromoethane sulfonic acid sodium salt and the mixture heated to 110° C. for 3 hours. The solution was filtered and the filtrate was distilled at reduced pressure. The residual solid was dissolved in excess water and poured into conc. hydrochloric acid. The solid that precipitated was filtered and washed with water and then air dried. The recovered solid was recrystallized from acetonitrile to give 2.7 grams of a yellow solid which melted at 138°-140° C.

TABLE X

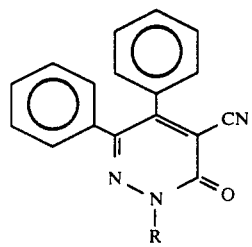

| Example Number | R | M.W. | Yield % | M.P. C.° | Formula | Calc for | Found | Prep.++ |
|---|---|---|---|---|---|---|---|---|
| 166 | \|<br>CH—(COOC$_2$H$_5$)$_2$ | 431.45 | 42 | 131–133 | C$_{24}$H$_{21}$N$_3$O$_5$ | C, 66.80<br>H, 4.90<br>N, 9.70 | C, 66.50<br>H, 5.10<br>N, 9.70 | 166 |
| 167 | —CH$_2$SCH$_3$ | 333.39 | ≠ | ≠ | C$_{19}$H$_{15}$N$_3$O$_1$S$_1$ | C, 68.44<br>H, 9.59<br>N, 12.59 | ≠<br>≠<br>≠ | 158 |
| 168 | —CH$_2$CH$_2$OCH=CH$_2$ | 343.35 | ≠ | 165–166 | C$_{21}$H$_{17}$N$_3$O$_2$ | C, 73.45<br>H, 4.99<br>N, 12.2 | ≠<br>≠<br>≠ | 158 |
| 169 | CH$_2$OCH$_2$C≡CH | 341.37 | 48 | 123–125 | C$_{21}$H$_{15}$N$_3$O$_2$ | C, 73.8<br>H, 4.4<br>N, 12.3 | C, 73.8<br>H, 4.5<br>N, 12.9 | 158 |
| 158 | —CH$_2$CH$_2$—OCH$_2$CH$_3$ | 345.36 | 61 | 116–117 | C$_{12}$H$_{19}$N$_3$O$_2$ | C, 73.0<br>H, 5.5<br>N, 12.2 | C, 73.1<br>H, 5.7<br>N, 12.0 | 158 |
| 160 | —CH$_2$CN | 212.28 | 54 | 198 | C$_{19}$H$_{12}$N$_4$O$_1$ | C, 73.0<br>H, 3.97<br>N, 17.9 | C, 72.7<br>H, 4.1<br>N, 17.9 | 160 |
| 159 | —CH$_2$CH$_2$CN | 326.32 | 42 | 160–161 | C$_{20}$H$_{14}$N$_4$O$_1$ | C, 73.6<br>H, 4.3<br>N, 17.2 | C, 73.2<br>H, 4.22<br>N, 17.0 | 159 |
| 170 | —CH=CHCN | 324.33 | 48 | 219 | C$_{20}$H$_{12}$N$_4$O$_1$ | C, 74.1<br>H, 3.73<br>N, 17.3 | C, 74.7<br>H, 4.0<br>N, 17.9 | 159 |
| 161 | —CH$_2$CH$_2$N—(C$_2$H$_5$)$_2$ | 372.47 | 63.4 | 100–101 | C$_{23}$H$_{24}$N$_4$O$_1$ | C, 74.17<br>H, 6.50<br>N, 15.04 | C, 74.19<br>H, 6.34<br>N, 15.03 | 161 |
| 171 | —CH$_2$CH$_2$N⟨piperidine⟩ | 384.43 | 64 | 168–169 | C$_{24}$H$_{24}$N$_4$O$_1$ | C, 74.97<br>H, 6.25<br>N, 14.57 | C, 75.12<br>H, 6.23<br>N, 14.61 | 161 |
| 172 | —CH$_2$N⟨piperidine⟩ | 370.40 | 76 | 156–157 | C$_{23}$H$_{22}$N$_4$O$_1$ | C, 74.5<br>H, 5.98<br>N, 15.11 | C, 74.7<br>H, 6.1<br>N, 15.11 | 162 |
| 173 | —CH$_2$N⟨pyrrolidine⟩ | 356.38 | 60 | 143–144 | C$_{22}$H$_{20}$N$_4$O$_1$ | C, 74.13<br>H, 5.65<br>N, 15.7 | C, 74.1<br>H, 5.56<br>N, 15.7 | 162 |
| 162 | —CH$_2$N⟨2,5-dimethylpyrrolidine⟩ | 384.43 | 57.8 | 156 | C$_{24}$H$_{22}$N$_4$O | C, 74.90<br>H, 6.29<br>N, 14.6 | C, 74.5<br>H, 6.4<br>N, 14.7 | 162 |
| 164 | —CH$_2$CH$_2$SC$_2$H$_5$<br>\|<br>O$_2$ | 374.40 | 37 | 154–155 | C$_{21}$H$_{19}$SN$_3$O$_3$ | C, 67.30<br>H, 4.84<br>N, 14.95 | C, 67.40<br>H, 4.84<br>N, 15.02 | 164 |
| 163 | —CH$_2$CHCH$_2$CH$_3$<br>\|<br>NO$_2$ | 393.46 | 72 | oil | C$_{21}$H$_{18}$N$_4$O$_3$ | C, 64.10<br>H, 4.86<br>N, 10.70 | C, 63.90<br>H, 4.80<br>N, 10.80 | 163 |

TABLE X-continued

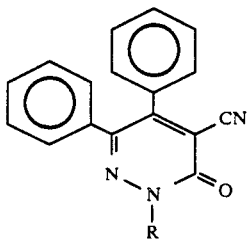

| Example Number | R | M.W. | Yield % | M.P. C.° | Formula | Calc for | Found | Prep.++ |
|---|---|---|---|---|---|---|---|---|
| 165 | —CH₂CH₂SC(=S)N(CH₃)₂ | 420.41 | 67 | ≠ | C₂₂H₂₀N₄O₁S₂ | C, 62.85<br>H, 4.76<br>N, 13.33 | C, ≠<br>H, ≠<br>N, ≠ | 165 |
| 230 | CH₂CH₂SO₃H.H₂O | 399 | ≠ | 138–140 | C₁₉H₁₅N₃O₄S | C, 57.1<br>H, 4.3<br>N, 10.5 | C, 56.6<br>H, 4.4<br>N, 10.7 | 230 |

≠ Data Not Available
**The compounds in this table were prepared in accordance to the synthesis procedure of the examples represented by the numbers in this column.

Example 174 through 190 illustrate amino acid derivatives of diphenylpyridazinones. These compounds are summarized in Table XI.

EXAMPLE 174

N-[3-(3,4-diphenyl-5-cyano-6-oxo-1,6-dihydro-pyridazin-1-yl)-1-oxo-propyl]-glycine methyl ester

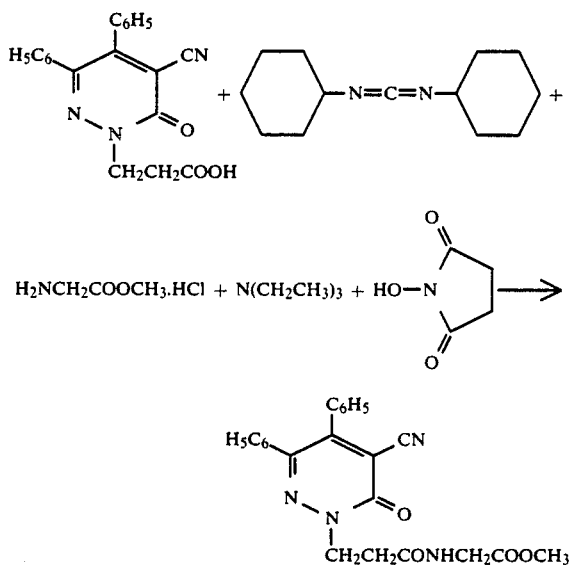

13.8 grams (0.04 mole) of the product of Example 64 reacted with 5.06 grams (0.043 mole) of N-hydroxysuccinimide and 8.25 grams (0.04 mole) of N,N-dicyclohexyl carbodiimide in 100 mls of THF at 5° C. for 1 hour. 5.52 grams (0.044 mole) of glycine methylester hydrochloride was added to the suspension followed by the addition of 4.45 grams (0.044 mole) of triethylamine in 6.1 mls of DMF. This suspension was stirred for 20 hours at room temperature. The precipitate (dicyclohexylurea-triethylammonium chloride) was filtered and the solvent was distilled at reduced pressure. The residual solid was taken up in ethyl acetate. The ethyl acetate solution was washed first with 0.5 molar hydrochloric acid followed with 0.5 molar sodium bicarbonate and finally with brine. The solution was dried over MgSO₄, filtered and the solvent distilled at reduced pressure. The crude product was recrystallized from a mixture of ethylacetate and petroleum ether to give 11 grams (66% yield) of the desired product that melted with decomposition at 114°–115° C.

EXAMPLE 175

N-[3-(3,4-diphenyl-5-cyano-6-oxo-1,6-dihydropyridazin-1-yl)-1-oxopropyl]glycine 5.2 grams (0.0124 mole) of the product typified in Example 174 was dissolved in a mixture of 25% aqueous acetone at 0° C. 12.5 mls of 1 molar sodium hydroxide (0.5 grams, 0.0125 mole) was added to this solution and the mixture stirred for 2 hours at 0° C. The acetone water solvent was distilled at reduced pressure and the residual mixture extracted with chloroform. The organic layer was then separated and extracted with 1M sodium bicarbonate (20 mls). The aqueous fractions were combined and made acid to Congo Red (1 molar HCl). The solid that separated out was extracted with 200 mls of chloroform, and then with 3 further aliquots (100 mls). The combined chloroform product was dried over MgSO₄, filtered and the solvent distilled at reduced pressure. This left a colorless syrup which solidified upon being triturated with isopropyl alcohol. 4.7 grams of this solid was recrystallized from isopropyl alcohol to give 4.0 grams (80% yield) of a solid that melted at 113°–115° C.

EXAMPLE 176

3-(2-(5-cyano-1,6-dihydro-6-oxo-3,4-diphenylpyridazin-1-yl)-ethylamino)-3-oxopropanoic acid, ethylester A solution of 4-cyano-5,6-diphenyl-3-(2H)-pyridazinone (50 g, 0.183 mole), N-(2-bromoethyl)-phthalimide (48.8 g, 0.192 mole), and anhydrous sodium carbonate (24.2 g, 0.228 mole), in dimethylformamide (300 mls) was heated 80°–85° C. in silicone oil and stirred for 48 hours. The slightly cooled reaction mixture was poured into ice water with vigorous shaking, and the suspension that formed set aside in the refrigerator for 1 hour. The precipitate was filtered, washed with water, air dried, and maintained in vacuo over drierite overnight.

Crystallization of the light brown amorphous solid (89 g) from 95% ethanolacetonitrile yielded 81 grams (99%) of the crystalline phthaloylamino derivative. The sample was twice further recrystallized from 95% ethanol-acetonitrile and dried in vacuo at 56° C. It had a melting point of 177°-178° C.

This phthaloylamino derivative (33.45 g, 75 mmole) was dissolved in 500 ml of boiling methanol. The slightly cooled solution was treated with 10.3 ml of 85% hydrazine hydrate and heated under a steam bath reflux for 2 hours. The reaction mixture was cooled to room temperature, and evaporated in vacuo. The orange semi-solid residue was digested with 250 ml of 50% aqueous acetic acid.

A suspension was formed and filtered and the white precipitate of phthalyhydrazide washed with 50 ml of warm 50% aqueous acetic acid and 50 ml warm water. The combined filtrate and washings were brought to pH 9 with 4M sodium hydroxide solution with cooling and extracted 3 times with 200 ml of chloroform aliquot. The chloroform extract was washed twice with 50 ml of brine aliquot, dried and evaporated in vacuo. The brown semi-solid residue (51 g) was dried with drierite in vacuo overnight, taken up in acetic acid, and treated with hydrogen bromide in 20 ml of 30% acetic acid with stirring. Ether was added, with vigorous stirring, depositing a brown powder. Stirring was maintained for 1 hour at room temperature. Then the supernate was decanted and the precipitate washed with 50 ml of ether. The crude product was reprecipitated from a methanol-ether solution, filtered, washed with ether, and dried with drierite in vacuo to yield 24.5 grams (82% yield) of the hydrobromide as a tan powder. The analytical sample was recrystallized from 95% ethanol (80% recovery).

3.4 grams (0.02 mole) of potassium monoethyl malonate was partitioned between 1M brine in 22 ml of hydrochloric acid and 20 ml of chloroform. The organic phase was separated and the aqueous phase extracted twice with 20 ml of chloroform aliquot. The chloroform extract was washed with brine, dried and evaporated in vacuo to a clear viscous oil. A solution of the oil, and 2.3 g (0.02 mole) of N-hydroxysuccinimide in 40 ml of tetrahydrofuran was cooled in ice and treated with a solution of 4.1 g (0.02 mole) of N,N'-dicyclohexylcarbodiimide in 10 ml tetrahydrofuran. The reaction mixture was stirred for 2 hours, maintaining the ice bath, and treated with a solution of 2-(2-aminoethyl)-4-cyano-5,6-diphenyl-(2H)-pyridazin-3-one in dimethylformamide, prepared as follows: the hydrobromide (7.94 g, 20 mmole) was partitioned between 1M sodium hydroxide (22 ml) and chloroform (50 ml). The organic phase was separated and the aqueous phase extracted twice with chloroform aliquot. The chloroform extract was washed with brine, dried and evaporated to an orange semi-solid residue which was taken up in dimethylformamide.

The reaction mixture was stirred overnight at room temperature. Approximately 4.5 g of dicyclohexylurea was filtered, and the filtrate evaporated in vacuo to a viscous oil which was taken up in 100 ml of ethyl acetate containing 3 drops of 50% aqueous acetic acid. The solution was set aside for 1 hour at toom temperature, filtered, and washed 3 times each with 0.5M HCl, 5% NaHCO$_3$, and brine, dried, and evaporated in vacuo to a viscous oil which was crystallized by dissolution in ethyl acetate, dilution with ether and the careful addition of hexane to yield 5.2 g (60%) of the pyridazinone derivative. The analytical sample, mp 128°-130° C., recrystallized from ethyl acetate-ether, gave infrared and integrated PMR spectra consistent with the proposed structure.

EXAMPLE 177

N-N[3-(5-Cyano-1,6-dihydro-6-oxo-3,4-diphenyl-pyridazin-1-yl)-1-oxopropyl]-glycyl glycine A solution of 1.95 ml of isobutyl chloroformate in 2 ml of acetone was added during 5 minutes to a stirred and cooled (−10° C. to −15° C., dry-ice/acetone) solution of 5.2 g of the product of Example 64 and 23 ml triethylamine in 50 ml of acetone. The reaction mixture was stirred for 5 minutes at −10° to −15° C., and then a solution of 3.96 grams (0.03 mole) glycylglycine (3.96 g, 30 mmole) in 30 ml of 1M aqueous sodium hydroxide was added during 15 minutes. The mixture was maintained at 0° to −5° C. during the addition and for 15 minutes thereafter. The cooling bath was removed, and the reaction mixture allowed to attain room temperature, and stirred for 3 hours. The acetone was evaporated in vacuo and the residual aqueous solution diluted with 1 vol. of 0.5M aqueous sodium bicarbonate, cooled and made acid to Congo Red by the gradual addition of 1M hydrochloric acid. The oil which separated was extracted 3 times with 100 ml of chloroform aliquot, and the extract washed 3 times with brine (20 ml aliquot), dried and evaporated in vacuo to a viscous yellow oil which solidified upon storage, in the cold, overnight. The crude product was crystallized from 30% aqueous ethanol to yield 4.5 grams (67%) of the glycine derivative (mp 108°-110° C.).

EXAMPLE 178

1-Oxo,2-[3-(5-cyano-1,6-dihydro-6-oxo-3,4-diphenyl)-3-(4-hydroxyphenyl)]propylaminopropanamide A solution of 3.03 grams diphenylphosphoryl azide in 5 ml dimethylformamide was added gradually with stirring, to a precooled (0° to −5° C.) solution of 3.45 g of the product of Example 64 and 1.98 g tyrosine amide in 25 ml dimethylformamide. Then the temperature of the reaction mixture was maintained at 0° to −5° C. during the gradual addition of a solution of 1.54 ml triethylamine in 5 ml dimethylformamide. The mixture was allowed to attain room temperature and was set aside overnight with stirring. The mixture was then poured over crushed ice with stirring, and the precipitated material filtered, washed with water, and air dried. A solution of the crude material in 100 ml ethyl acetate was washed 3 times with 20 ml of 0.5M hydrochloric acid aliquot and 3 times with 20 ml of water, dried over magnesium sulphate, and evaporated in vacuo to a foam which solidified upon trituration with ether to a light yellow powder. This yielded a 100% yield of 5.4 g, slightly contaminated by the product of Example 64. Enrichment was achieved by reprecipitation from ethyl acetate-petrol or from tetrahydrofuran-ether. Preferably, dry-column chromatography afforded a 75% yield of the pure compound with mp of 137°-140° C.

EXAMPLE 179

Ethyl-N-[N-(1-oxo-3-(5-cyano-1,6-dihydro-6-oxo-3,4-diphenylpyridazin-1-yl)propyl]-leucinylglycinate A suspension of 1 g of t-butoxycarbonylleucinylglycine ethyl ester in 10 ml ether was cooled to −5° C. and treated, with stirring, with 2 ml of 30% HBr-acetic acid, causing solution. The cooling bath was removed at 10 minutes; and 20 minutes later, the reaction mixture was evaporated in vacuo to an oil which was washed twice with ether by decantation, taken up in 5 ml DMF, and brought to an apparent pH 8 by dropwise addition of 0.5 ml triethylamine.

A solution of pivaloyl chloride in 1 ml of 3M acetonitrile was added in dropwise manner with stirring to a precooled (0° to −5° C., ice-salt bath) solution of 1.04 grams of the product of Example 64 and 0.46 ml of triethylamine in 10 ml of acetonitrile. The reaction mixture was maintained at 0° to −5° C. for 30 minutes, the cooling bath then removed, and stirring continued when the solution (prepared above) of ethyl leucinylglycinate was added and stirred overnight at room temperature.

The bulk of the solvent was evaporated in vacuo and the residual DMF solution poured into 25 ml of cold 0.1M hydrochloric acid. The precipitate gum was extracted 3 times with 20 ml of ethyl acetate aliquot. The ethyl acetate was washed 3 times with 0.5M hydrochloric acid, 5% aqueous sodium bicarbonate and 10 ml distilled water (aliquot). It was then dried over magnesium sulphate and evaporated in vacuo to 1.5 grams of a foam which solidified upon trituration with petroleum ether. The crude material was deposited as a gel from ethyl acetate-ether-hexane which was digested with ether, filtered, ether washed, air dried and dried in vacuo, to yield 950 mg (60% yield) of the pure compound, a white powder. Elemental analysis was consistent with formulation as the hemihydrate.

TABLE XI

[Structure: diphenyl compound with CN, C=O, N-N-CH₂CH₂R substituents]

| Example Number | R | R₁ | M.W. | Yield % | M.P. °C | Formula | Calc. For | Found | Prep.* |
|---|---|---|---|---|---|---|---|---|---|
| 174 | —CONHCH—COOCH₃<br>　　　\|<br>　　　R₁ | H | 416.4 | 66 | 113–115,<br>>115d | $C_{23}H_{20}N_4O_4$ | C, 66.35<br>H, 4.85<br>N, 13.45 | C, 66.6<br>H, 5.0<br>N, 13.6 | 174 |
| 175 | —CONHCHR₁COOH.CH₃CHOHCH₃ | H | 462.5 | 80 | 113–115 | $C_{22}H_{18}N_4O_4 \cdot C_3H_8O$ | C, 64.7<br>H, 5.7<br>N, 12.1 | C, 64.7<br>H, 5.8<br>N, 12.1 | 175 |
| 176 | —NHCOCH—COOC₂H₅<br>　　　\|<br>　　　R₁ | H | 430.5 | 60 | 128–130 | $C_{24}H_{22}N_4O_4$ | C, 67.0<br>H, 5.15<br>N, 13.0 | C, 66.7<br>H, 5.4<br>N, 13.1 | 176 |
| 177 | —CONHCH—CONHCH₂COOH<br>　　　\|<br>　　　R₁ | H | 459.5 | 67 | 108–110 | $C_{24}H_{21}N_5O_5$ | C, 62.7<br>H, 4.6<br>N, 15.2 | C, 62.4<br>H, 4.6<br>N, 15.0 | 177 |
| 180 | —CONHCH—CON—CHCOOH<br>　　　\|　　　　　\|<br>　　　R₁　　(pyrrolidine ring) | H | 499.5 | 50 | 153–155 | $C_{27}H_{25}N_5O_5$ | C, 64.9<br>H, 5.05<br>N, 14.0 | C, 64.6<br>H, 5.0<br>N, 14.05 | 177 |
| 181 | —CONHCH(R₁)<br>　　　\|<br>　　　CH₂OH | —COOCH₃ | 446.5 | 67 | 119–121 | $C_{24}H_{22}N_4O_5$ | C, 64.55<br>H, 4.95<br>N, 12.55 | C, 64.3<br>H, 5.1<br>N, 12.5 | 174 |
| 182 | —CONHCHR₁<br>　　　\|<br>　　　CH₂CH(CH₃)₂ | —COOH · [2,6-dimethylpiperidine] · ½H₂O | 589.7 | 61 | 135–138 | $C_{26}H_{27}N_4O_4 \cdot C_7H_{14}N \cdot \tfrac{1}{2}H_2O$ | C, 68.2<br>H, 7.3<br>N, 12.1 | C, 68.1<br>H, 7.6<br>N, 12.0 | 175 |
| 183 | —CONHCHR₁<br>　　　\|<br>　　　(CH₂)₂CONH₂ | —COOH·½H₂O | 483.5 | 66 | 183–185 | $C_{25}H_{24}N_5O_5 \cdot \tfrac{1}{2}H_2O$ | C, 62.1<br>H, 5.2<br>N, 14.5 | C, 61.9<br>H, 5.2<br>N, 14.5 | 177 |

TABLE XI-continued

[Structure: diphenyl compound with CN, N=N, and CH₂CH₂R groups]

| Example Number | R | R₁ | M.W. | Yield % | M.P. °C. | Formula | Calc. For | Found | Prep.* |
|---|---|---|---|---|---|---|---|---|---|
| 179 | —CONHCHR₁<br>CH₂CH(CH₃)₂ | —CONHCH₂COOC₂H₅·½H₂O | 552.6 | 60 | 91–95 | C₃₀H₃₃N₅O₅·½H₂O | C, 65.2<br>H, 6.2<br>N, 12.65 | C, 65.1<br>H, 6.15<br>N, 12.75 | 179 |
| 184 | —CONHCHR₁<br>CH—C₂H₅<br>CH₃ | —COOH·[cyclohexyl-NH]·½H₂O | 648.9 | 58 | 185–190 | C₂₆H₂₆N₄O₄·C₁₂H₂₃N·½H₂O | C, 70.35<br>H, 7.8<br>N, 10.8 | C, 70.6<br>H, 8.2<br>N, 10.8 | 177 |
| 185 | —CONHCHR₁<br>CH₂C₆H₅ | —COOC₂H₅ | 520.6 | 70 | 65–70 | C₃₁H₂₈N₄O₄ | C, 71.5<br>H, 5.4<br>N, 10.75 | C, 71.5<br>H, 5.7<br>N, 10.5 | 174 |
| 178 | —CONHCHR₁<br>CH₂C₆H₄—(p)-OH | —CONH₂·H₂O | 543.6 | 82 | 139–140 | C₂₉H₂₅N₅O₄·H₂O | C, 66.25<br>H, 5.2<br>N, 13.3 | C, 66.15<br>H, 4.95<br>N, 12.75 | 178 |
| 186 | —CONHCHR₁<br>COOC₂H₅ | —COOC₂H₅ | 502.5 | 82 | 106–108 | C₂₇H₂₆N₄O₆ | C, 64.5<br>H, 5.3<br>N, 11.15 | C, 64.2<br>H, 5.2<br>N, 11.1 | 174 |
| 187 | —CONHCHR₁<br>(CH₂)₄NHCOOCH₂C₆H₅ | —COOH·[cyclohexyl-NH]·H₂O | 807.3 | 39 | 133–137 | C₃₄H₃₃N₅O₆·C₁₂H₂₃N·H₂O | C, 68.45<br>H, 7.25<br>N, 10.4 | C, 68.75<br>H, 7.3<br>N, 10.1 | 175 |
| 188 | —CON[R₁—C—COOH·cyclohexyl-NH·H₂O]<br>(ring) | —H | 641.8 | 44 | 135–138 | C₃₇H₄₅N₅O₄·H₂O | C, 69.25<br>H, 7.4<br>N, 10.9 | C, 69.45<br>H, 7.55<br>N, 10.5 | 177 |
| 189 | —CONCH—COOCH₃<br>R₁ CH₃ | —H | 430.5 | 70 | 112–114 | C₂₄H₂₂N₄O₄ | C, 66.95<br>H, 5.15<br>N, 13.0 | C, 66.8<br>H, 5.2<br>N, 13.1 | 174 |

TABLE XI-continued
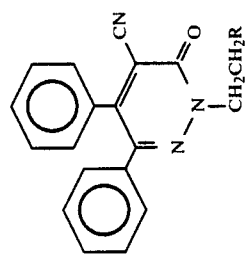
| Example Number | R | $R_1$ | M.W. | Yield % | M.P. °C. | Formula | Calc. For | Found | Prep.* |
|---|---|---|---|---|---|---|---|---|---|
| 190 | CONHCHCH$_2$—COOH.½H$_2$O<br>\|<br>$R_1$ | —H | 425.4 | 47 | 108–111 | $C_{23}H_{20}N_4O_4 \cdot \frac{1}{2}H_2O$ | C, 64.9<br>H, 5.0<br>N, 13.15 | C, 64.9<br>H, 4.9<br>N, 13.4 | 177 |
*The compounds in this table were prepared in accordance to the synthesis procedure of the examples represented by the numbers in this column.

Examples 223-239 illustrate various hydrazine derivatives of diphenylpyridazinones. These compounds were prepared in 48% to 100% yields from the reaction of the appropriate hydrazide and the desired phenyl isothiocyanate or alkyl isocyanate in 95% ethanol. The compounds are summarized in Table XXIX.

EXAMPLE 223

Acetic Acid hydrazide of 2-(N-(4-fluorophenylthiocarbamyl)-5-cyano-1,6-dihydro-6-oxo-3,4-diphenylpyridazin-1-yl

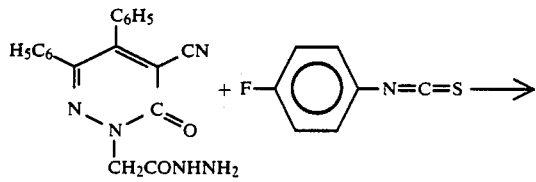

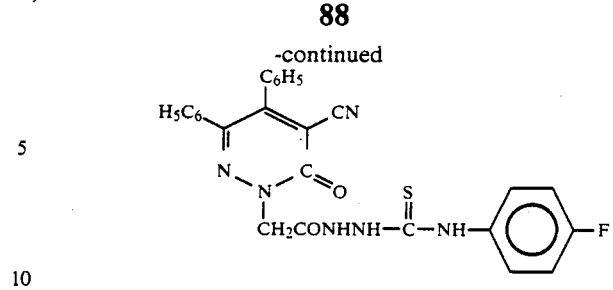

2.0 grams (0.006 mole) of laboratory prepared Acetic Acid hydrazide of 5-cyano-1,6-dihydro-6-oxo-3,4-diphenylpyridazin-1-yl was dissolved in approximately 16 mL of 95% ethanol.

To this solution was added 1.0 gram (0.0066 mole) of 4-fluorophenyl isothiocyanate and approximately 5 drops of triethylamine. This mixture was stirred at 50° C.

During a 15 min period, the clear, red solution became bright yellow, forming a thick slurry.

This slurry was chilled in a wet ice bath and suction filtered. The filter cake was washed with cold Abs. ethanol and pet. ether and then air dried to give 2.5 grams of the title compound which melted at 212° C.

TABLE XXIX

| Example Number | X | n | Yield % | M.P. °C. | R | M.W. | Formula | Calcd for | Found | Prep. No. |
|---|---|---|---|---|---|---|---|---|---|---|
| 223 | O | 1 | 83.3 | 212-213 | -C(S)-NH-C6H4-F (4-F) | 498.54 | $C_{26}H_{19}F_1N_6O_2S_1$ | C, 62.6 H, 3.8 N, 16.9 | C, 62.1 H, 3.9 N, 17.2 | 223 |
| 224 | O | 1 | 73 | 215 | -C(S)-NH-C6H5 | 480.55 | $C_{26}H_{20}N_6O_2S_1$ | C, 64.9 H, 4.20 N, 17.49 | C, 64.7 H, 4.1 N, 17.8 | 223 |
| 225 | O | 1 | 70 | 213 | -C(S)-NH-C6H4-CF3 | 548.54 | $C_{27}H_{19}F_3N_6O_2S_1$ | C, 59.1 H, 3.5 N, 15.3 | C, 59.0 H, 3.2 N, 15.6 | 223 |
| 226 | O | 1 | 90 | 220 | -C(S)-NH-C6H4-F | 498.54 | $C_{26}H_{19}F_1N_6O_2S_1$ | C, 62.6 H, 3.8 N, 16.9 | C, 62.4 H, 3.7 N, 17.1 | 223 |
| 227 | O | 1 | 84 | 247 | -C(O)-NH-CH3 | 402.4 | $C_{21}H_{18}N_6O_3$ | C, 62.7 H, 4.5 N, 20.9 | C, 62.4 H, 4.4 N, 21.1 | 223 |
| 228 | O | 2 | 82 | 172-174 | H | 359.3 | $C_{20}H_{17}N_5O_2$ | C, 66.84 H, 4.76 N, 19.4 | C, 66.8 H, 4.8 N, 19.5 | 223 |

TABLE XXIX-continued

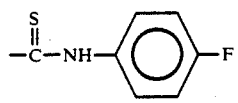

| Example Number | X | n | Yield % | M.P. °C. | R | M.W. | Formula | Calcd for | Found | Prep. No. |
|---|---|---|---|---|---|---|---|---|---|---|
| 229 | O | 2 | 100 | 187 | -C(=S)-NH-C6H4-F | 512.48 | $C_{27}H_{21}F_1N_6O_2S_1$ | C, 63.2<br>H, 4.13<br>N, 16.30 | C, 63.2<br>H, 4.32<br>N, 16.15 | 223 |

Preemergent and Postemergent Herbicide Tests

To illustrate the preemergence and postemergence herbicidal efficacy of the diphenylpyridazinone compounds of the present invention, test formulations of representative compounds are prepared by mixing 20 ml of an acetone solution containing 0.0416 g of the test compound with 20 ml of water containing 0.02 ml of Ortho X-77 surfactant. The resultant formulations contain 1040 ppm of test compound, 50 percent, by volume, of acetone and 0.05 percent, by volume, of surfactant. Appropriate lower concentrations are obtained by diluting this formulation with surfactant-acetone solution so that the concentration of adjuvants is maintained at the original levels.

Seeds of three broadleaf, three grassy weed species and three crop species are planted in the soil contained in 10×8×3 inch fiber pans filled with 2.0 inches of pasteurized soil (Kingsville sandy loam). The broadleaf species are pigweed (*Amaranthus retroflexus* L.), velvet leaf (*Abutilon theophrasti* Medic.) and mustard (*Brassica kaber* (DC.) Wheeler); the grasses are red millet (*Panicum milliaceum* L.), green foxtail (*Setaria viridis* (L.) Beauv.) and barnyard grass (*Echinochloa crus-galli* (L.) Beauv.), and the crops are cotton (*Gossypium hirsutum* L. 'Stoneville' 213), soybean (*Glycine max* (L.) Merr. 'Lancer') and corn (*Zea mays* (L.) 'Pioneer' 3518 F14). The pans are then sprayed so that the soil surface is uniformly covered with dilutions of the stock formulation providing dosage rates of the test compounds corresponding to 8, 4, 2, 1, 0.5, 0.25, 0.12, 0.06, etc., kg/hectare. Two weeks after treatment, percent control (plant kill) at each dosage rate is estimated.

The postemergent herbicide tests are carried out in the same manner described above, except that the herbicide formulations are applied to the foliage of the seedling plants.

In Tables XII (preemergent) and XIII (postemergent) below, the results obtained according to the foregoing test procedures with respect to the application or dosage rate of the active compounds according to the present invention and the percent weed control (effectiveness) exerted by the test compounds are summarized. Also, shown is percent control (tolerance) on crops.

TABLE XII

| Compound Example No. | DOSE KG/HA | PIG-WEED | VEL. LEAF | MUS-TARD | RED MIL. | FOX-TAIL | B.Y. GRSS | COT-TON | SOY-BEAN | CORN |
|---|---|---|---|---|---|---|---|---|---|---|
| | | | | | % Control Preemergence[1] | | | | | |
| 1 | 8.00 | 60 | 20 | 60 | 10 | 0 | 20 | 20 | 0 | 0 |
| | 4.00 | 65 | 25 | 55 | 10 | 10 | 15 | 45 | 10 | 0 |
| | 2.00 | 30 | 10 | 40 | 10 | 0 | 10 | 45 | 10 | 0 |
| | 1.00 | 40 | 10 | 20 | 0 | 10 | 0 | 95 | 10 | 0 |
| | 0.50 | 70 | 10 | 30 | 10 | 10 | 0 | 40 | 0 | 0 |
| | 0.25 | 40 | 0 | 30 | 10 | 0 | 0 | 0 | 0 | 0 |
| 9 | 2.00 | 90 | 30 | 90 | 0 | 30 | 50 | 0 | 50 | 30 |
| | 1.00 | 60 | 0 | 40 | 0 | 20 | 10 | 0 | 10 | 0 |
| | 0.50 | 40 | 0 | 50 | 0 | 10 | 0 | 0 | 0 | 0 |
| 11 | 4.00 | 30 | 0 | 10 | 10 | 10 | 30 | 0 | 0 | 0 |
| | 2.00 | 10 | 0 | 10 | 0 | 0 | 20 | 0 | 0 | 0 |
| 20 | 4.00 | 50 | 40 | 60 | 70 | 70 | 70 | 0 | 30 | 0 |
| | 2.00 | 30 | 15 | 45 | 40 | 40 | 40 | 10 | 15 | 15 |
| | 0.50 | 10 | 0 | 10 | 30 | 10 | 20 | 0 | 10 | 20 |
| 22 | 4.00 | 60 | 50 | 40 | 70 | 70 | 70 | 0 | 0 | 10 |
| | 2.00 | 60 | 30 | 20 | 40 | 40 | 50 | 0 | 0 | 10 |
| 30 | 8.00 | 100 | 100 | 100 | 100 | 100 | 100 | 100 | 95 | 95 |
| | 4.00 | 97 | 87 | 95 | 100 | 97 | 100 | 70 | 87 | 82 |
| | 2.00 | 95 | 75 | 95 | 95 | 95 | 95 | 70 | 90 | 60 |
| | 1.00 | 90 | 65 | 90 | 85 | 85 | 80 | 50 | 60 | 40 |
| | 0.50 | 85 | 30 | 90 | 70 | 85 | 80 | 10 | 40 | 20 |
| | 0.25 | 70 | 20 | 75 | 50 | 70 | 65 | 20 | 20 | 30 |
| | 0.12 | 45 | 10 | 75 | 25 | 65 | 30 | 5 | 0 | 20 |
| 38 | 2.00 | 90 | 90 | 90 | 90 | 90 | 90 | 0 | 60 | 40 |
| | 1.00 | 90 | 55 | 90 | 85 | 90 | 85 | 40 | 40 | 40 |
| | 0.50 | 90 | 20 | 90 | 70 | 80 | 90 | 0 | 10 | 30 |
| | 0.25 | 70 | 55 | 75 | 60 | 65 | 60 | 55 | 40 | 35 |
| 51 | 8.00 | 90 | 80 | 90 | 95 | 90 | 95 | 30 | 50 | 40 |
| | 4.00 | 90 | 80 | 90 | 100 | 95 | 100 | 20 | 90 | 90 |
| | 2.00 | 90 | 70 | 90 | 95 | 90 | 100 | 20 | 90 | 30 |

TABLE XII-continued

% Control Preemergence[1]

| Compound Example No. | DOSE KG/HA | PIG-WEED | VEL. LEAF | MUS-TARD | RED MIL. | FOX-TAIL | B.Y. GRSS | COT-TON | SOY-BEAN | CORN |
|---|---|---|---|---|---|---|---|---|---|---|
|  | 1.00 | 87 | 45 | 85 | 65 | 80 | 60 | 10 | 30 | 10 |
|  | 0.50 | 80 | 20 | 60 | 90 | 70 | 90 | 10 | 10 | 0 |
|  | 0.25 | 72 | 10 | 60 | 35 | 30 | 45 | 0 | 0 | 0 |
|  | 0.12 | 50 | 0 | 20 | 30 | 10 | 10 | 0 | 0 | 0 |
| 64 | 16.00 | 100 | 95 | 100 | 100 | 100 | 100 | 95 | 95 | 95 |
|  | 8.00 | 100 | 90 | 100 | 100 | 100 | 100 | 80 | 95 | 95 |
|  | 4.00 | 100 | 87 | 95 | 95 | 97 | 97 | 70 | 90 | 90 |
|  | 2.00 | 100 | 70 | 95 | 90 | 90 | 95 | 30 | 85 | 75 |
|  | 1.00 | 95 | 40 | 92 | 80 | 80 | 90 | 20 | 70 | 60 |
|  | 0.50 | 95 | 40 | 90 | 60 | 65 | 65 | 10 | 50 | 40 |
|  | 0.25 | 95 | 25 | 70 | 30 | 40 | 35 | 15 | 30 | 20 |
|  | 0.12 | 85 | 20 | 65 | 20 | 25 | 15 | 15 | 5 | 15 |
|  | 0.06 | 70 | 20 | 70 | 20 | 0 | 10 | 10 | 10 | 10 |
| 79 | 8.00 | 100 | 70 | 90 | 100 | 100 | 100 | 40 | 90 | 90 |
|  | 4.00 | 97 | 35 | 90 | 95 | 92 | 95 | 5 | 75 | 60 |
|  | 2.00 | 80 | 35 | 85 | 85 | 85 | 95 | 0 | 40 | 65 |
|  | 1.00 | 85 | 30 | 70 | 50 | 60 | 70 | 20 | 30 | 20 |
|  | 0.50 | 60 | 10 | 70 | 30 | 60 | 70 | 10 | 0 | 0 |
|  | 0.25 | 70 | 15 | 40 | 40 | 25 | 40 | 5 | 15 | 20 |
|  | 0.12 | 50 | 10 | 50 | 60 | 40 | 70 | 10 | 20 | 10 |
|  | 0.06 | 40 | 0 | 50 | 0 | 0 | 10 | 0 | 0 | 0 |
|  | 0.03 | 20 | 0 | 50 | 0 | 0 | 20 | 0 | 0 | 0 |
| 100 | 8.00 | 75 | 35 | 50 | 80 | 95 | 80 | 10 | 40 | 20 |
|  | 4.00 | 60 | 40 | 50 | 75 | 90 | 70 | 15 | 45 | 10 |
|  | 2.00 | 65 | 20 | 40 | 70 | 85 | 60 | 10 | 30 | 10 |
|  | 1.00 | 60 | 10 | 30 | 55 | 80 | 65 | 10 | 20 | 0 |
|  | 0.50 | 50 | 10 | 20 | 40 | 60 | 40 | 10 | 0 | 0 |
|  | 0.25 | 10 | 0 | 0 | 10 | 60 | 0 | 0 | 0 | 0 |
|  | 0.12 | 0 | 0 | 0 | 10 | 60 | 0 | 10 | 0 | 0 |
| 107 | 8.00 | 90 | 90 | 95 | 90 | 100 | 95 | 50 | 90 | 60 |
|  | 4.00 | 90 | 80 | 90 | 80 | 100 | 95 | 40 | 80 | 40 |
|  | 2.00 | 92 | 50 | 92 | 70 | 85 | 90 | 35 | 60 | 25 |
|  | 1.00 | 85 | 40 | 75 | 60 | 75 | 50 | 25 | 35 | 15 |
|  | 0.50 | 65 | 35 | 55 | 25 | 55 | 35 | 10 | 10 | 10 |
|  | 0.25 | 60 | 25 | 25 | 15 | 30 | 25 | 0 | 10 | 10 |
|  | 0.12 | 20 | 10 | 0 | 10 | 70 | 0 | 0 | 10 | 0 |
| 122 | 4.00 | 100 | 80 | 90 | 95 | 95 | 90 | 70 | 80 | 50 |
|  | 2.00 | 92 | 60 | 92 | 97 | 95 | 85 | 55 | 70 | 55 |
|  | 1.00 | 90 | 20 | 92 | 95 | 92 | 80 | 25 | 70 | 40 |
|  | 0.50 | 70 | 10 | 80 | 30 | 30 | 20 | 20 | 60 | 30 |
|  | 0.25 | 90 | 0 | 92 | 60 | 60 | 30 | 10 | 20 | 30 |
| 130 | 8.00 | 100 | 90 | 100 | 100 | 100 | 100 | 95 | 95 | 100 |
|  | 4.00 | 100 | 80 | 100 | 100 | 100 | 100 | 80 | 95 | 100 |
|  | 2.00 | 100 | 80 | 100 | 100 | 100 | 100 | 50 | 90 | 95 |
|  | 1.00 | 95 | 30 | 95 | 95 | 95 | 92 | 45 | 70 | 50 |
|  | 0.50 | 100 | 40 | 95 | 100 | 100 | 90 | 40 | 70 | 70 |
|  | 0.25 | 90 | 10 | 90 | 75 | 85 | 55 | 25 | 35 | 30 |
|  | 0.12 | 75 | 0 | 80 | 10 | 40 | 5 | 0 | 10 | 20 |
|  | 0.06 | 90 | 0 | 90 | 0 | 0 | 0 | 0 | 10 | 0 |
|  | 0.03 | 80 | 10 | 40 | 0 | 0 | 0 | 0 | 0 | 0 |
| 143 | 2.00 | 80 | 0 | 90 | 20 | 40 | 70 | 20 | 50 | 50 |
|  | 1.00 | 50 | 0 | 70 | 10 | 30 | 20 | 0 | 10 | 10 |
|  | 0.50 | 20 | 0 | 50 | 0 | 10 | 0 | 0 | 0 | 0 |
| 155 | 2.00 | 60 | 0 | 90 | 20 | 50 | 80 | 0 | 50 | 10 |
|  | 1.00 | 75 | 10 | 60 | 60 | 50 | 70 | 0 | 30 | 10 |
|  | 0.50 | 20 | 0 | 80 | 10 | 40 | 30 | 0 | 0 | 0 |
| 160 | 4.00 | 70 | 70 | 90 | 60 | 70 | 80 | 0 | 40 | 20 |
|  | 2.00 | 55 | 20 | 75 | 40 | 40 | 70 | 10 | 10 | 20 |
|  | 0.50 | 30 | 0 | 10 | 20 | 0 | 10 | 10 | 10 | 10 |
| 175 | 8.00 | 100 | 70 | 100 | 95 | 95 | 100 | 70 | 90 | 80 |
|  | 4.00 | 100 | 40 | 100 | 70 | 60 | 80 | 80 | 70 | 60 |
|  | 2.00 | 100 | 20 | 90 | 70 | 40 | 50 | 20 | 40 | 10 |
|  | 1.00 | 100 | 10 | 60 | 20 | 0 | 10 | 30 | 20 | 10 |
|  | 0.50 | 100 | 0 | 40 | 20 | 10 | 0 | 20 | 10 | 10 |
|  | 0.25 | 70 | 0 | 30 | 0 | 0 | 0 | 0 | 0 | 10 |
|  | 0.12 | 70 | 0 | 30 | 0 | 0 | 0 | 0 | 0 | 0 |

[1]Mean of all replications at indicated dose.

TABLE XIII

% Control Postemergence[1]

| Compound Example No. | DOSE KG/HA | PIG-WEED | VEL. LEAF | MUS-TARD | RED MIL. | FOX-TAIL | B.Y. GRSS | COT-TON | SOY-BEAN | CORN |
|---|---|---|---|---|---|---|---|---|---|---|
| 9 | 2.00 | 0 | 10 | 40 | 20 | 20 | 40 | 10 | 40 | 30 |
|  | 1.00 | 0 | 0 | 40 | 20 | 20 | 30 | 0 | 50 | 10 |
|  | 0.50 | 20 | 0 | 30 | 0 | 20 | 30 | 0 | 30 | 0 |
| 11 | 4.00 | 30 | 0 | 50 | 40 | 50 | 60 | 20 | 60 | 20 |

TABLE XIII-continued

| Compound Example No. | DOSE KG/HA | PIG-WEED | VEL. LEAF | MUS-TARD | RED MIL. | FOX-TAIL | B.Y. GRSS | COT-TON | SOY-BEAN | CORN |
|---|---|---|---|---|---|---|---|---|---|---|
| | 2.00 | 20 | 0 | 40 | 10 | 30 | 20 | 0 | 50 | 0 |
| 20 | 4.00 | 30 | 30 | 40 | 40 | 50 | 30 | 20 | 40 | 40 |
| | 2.00 | 25 | 15 | 30 | 25 | 30 | 25 | 10 | 45 | 25 |
| | 1.00 | 10 | 20 | 10 | 20 | 20 | 20 | 10 | 40 | 30 |
| | 0.50 | 0 | 20 | 0 | 20 | 20 | 10 | 10 | 40 | 10 |
| 22 | 4.00 | 20 | 30 | 30 | 50 | 50 | 50 | 10 | 30 | 20 |
| | 2.00 | 10 | 10 | 10 | 0 | 20 | 0 | 10 | 50 | 10 |
| 51 | 8.00 | 40 | 50 | 50 | 30 | 40 | 40 | 30 | 40 | 60 |
| | 4.00 | 30 | 60 | 50 | 40 | 50 | 40 | 30 | 50 | 40 |
| | 2.00 | 20 | 40 | 50 | 30 | 40 | 40 | 30 | 50 | 40 |
| | 1.00 | 10 | 40 | 50 | 20 | 30 | 10 | 30 | 50 | 20 |
| | 0.50 | 20 | 10 | 40 | 10 | 30 | 10 | 20 | 40 | 20 |
| | 0.25 | 10 | 10 | 50 | 10 | 30 | 10 | 20 | 40 | 10 |
| 64 | 32.00 | 95 | 60 | 80 | 70 | 80 | 75 | 50 | 70 | 70 |
| | 8.00 | 55 | 45 | 75 | 50 | 70 | 55 | 55 | 60 | 65 |
| | 4.00 | 70 | 50 | 50 | 70 | 70 | 70 | 40 | 50 | 80 |
| | 2.00 | 35 | 35 | 60 | 45 | 50 | 60 | 35 | 50 | 60 |
| | 1.00 | 35 | 25 | 50 | 50 | 45 | 60 | 15 | 50 | 70 |
| | 0.50 | 30 | 20 | 55 | 45 | 45 | 45 | 15 | 50 | 60 |
| 79 | 8.00 | 70 | 70 | 80 | 70 | 70 | 80 | 30 | 80 | 90 |
| | 4.00 | 30 | 45 | 55 | 55 | 60 | 60 | 20 | 55 | 70 |
| | 2.00 | 25 | 40 | 50 | 50 | 50 | 55 | 20 | 55 | 70 |
| | 1.00 | 30 | 45 | 50 | 50 | 55 | 55 | 25 | 55 | 70 |
| | 0.50 | 40 | 40 | 50 | 50 | 50 | 60 | 20 | 60 | 70 |
| | 0.25 | 50 | 10 | 50 | 50 | 40 | 60 | 30 | 40 | 60 |
| | 0.12 | 20 | 20 | 50 | 40 | 40 | 40 | 30 | 40 | 40 |
| | 0.06 | 40 | 10 | 50 | 10 | 40 | 10 | 20 | 40 | 0 |
| | 0.03 | 30 | 10 | 50 | 10 | 20 | 10 | 20 | 40 | 10 |
| 107 | 2.00 | 30 | 30 | 40 | 50 | 50 | 50 | 10 | 50 | 10 |
| | 1.00 | 10 | 20 | 40 | 60 | 50 | 50 | 10 | 50 | 10 |
| | 0.50 | 0 | 30 | 40 | 50 | 40 | 40 | 10 | 50 | 0 |
| 122 | 4.00 | 70 | 50 | 60 | 70 | 70 | 60 | 40 | 60 | 70 |
| | 2.00 | 45 | 25 | 60 | 50 | 60 | 25 | 25 | 55 | 65 |
| | 1.00 | 30 | 20 | 60 | 40 | 50 | 10 | 20 | 60 | 40 |
| | 0.50 | 20 | 10 | 60 | 40 | 40 | 0 | 10 | 60 | 20 |
| 130 | 8.00 | 50 | 50 | 60 | 50 | 70 | 60 | 50 | 50 | 40 |
| | 4.00 | 50 | 50 | 70 | 60 | 60 | 40 | 70 | 40 | 60 |
| | 2.00 | 30 | 20 | 50 | 50 | 50 | 40 | 60 | 40 | 20 |
| | 1.00 | 30 | 20 | 50 | 40 | 50 | 20 | 30 | 30 | 10 |
| | 0.50 | 10 | 10 | 50 | 30 | 40 | 10 | 30 | 40 | 10 |
| | 0.25 | 10 | 0 | 50 | 30 | 40 | 10 | 20 | 30 | 10 |
| | 0.12 | 10 | 20 | 50 | 0 | 20 | 0 | 20 | 20 | 10 |
| 143 | 2.00 | 20 | 40 | 60 | 50 | 40 | 50 | 20 | 50 | 60 |
| | 1.00 | 10 | 20 | 50 | 40 | 40 | 30 | 10 | 50 | 20 |
| | 0.50 | 10 | 20 | 50 | 20 | 30 | 20 | 0 | 50 | 30 |
| 155 | 2.00 | 50 | 30 | 60 | 60 | 60 | 40 | 10 | 60 | 70 |
| | 1.00 | 50 | 15 | 30 | 50 | 30 | 40 | 15 | 40 | 35 |
| | 0.50 | 45 | 20 | 35 | 40 | 30 | 25 | 10 | 45 | 25 |
| | 0.25 | 40 | 10 | 10 | 0 | 0 | 10 | 0 | 30 | 0 |
| 160 | 4.00 | 50 | 40 | 60 | 30 | 20 | 10 | 10 | 40 | 20 |
| | 2.00 | 30 | 25 | 55 | 15 | 10 | 0 | 10 | 40 | 10 |
| | 1.00 | 20 | 10 | 50 | 20 | 10 | 0 | 10 | 40 | 0 |
| | 0.50 | 20 | 10 | 50 | 30 | 0 | 0 | 20 | 30 | 0 |
| 175 | 8.00 | 60 | 30 | 60 | 60 | 70 | 70 | 10 | 50 | 70 |
| | 4.00 | 50 | 40 | 50 | 10 | 20 | 30 | 20 | 20 | 0 |
| | 2.00 | 20 | 10 | 50 | 10 | 10 | 20 | 0 | 20 | 0 |
| | 1.00 | 10 | 0 | 50 | 10 | 20 | 20 | 0 | 20 | 10 |
| | 0.50 | 0 | 0 | 50 | 0 | 10 | 0 | 10 | 10 | 0 |
| | 0.25 | 0 | 0 | 40 | 0 | 0 | 0 | 0 | 0 | 0 |

[1]Mean of all replications at indicated dose.

Plant Growth Regulant Activity

The compounds of the invention were also evaluated relative to plant growth regulant activity against three plant species in a petri dish test. The test is divided into a primary test where 500 μg and 100 μg chemical per petri dish (100×25 mm, disposable) are tested simultaneously and a secondary test where 50 μg to 0.1 μg chemical per petri dish are tested simultaneously. Compounds which pass the primary test are further evaluated in the secondary test. A special petri dish test may also be run to evaluate particular test compounds, in which case the primary tests and secondary tests are conducted simultaneously.

According to the test procedure, three plant species are planted in a petri dish which has been treated with the test substance. The three species are as follows: (1) a mixture of approximately 50 percent light-sensitive and 50 percent light-insensitive lettuce (*Lactuca sativa* L. 'Grand Rapids'); (2) soft red winter wheat [*Triticum aestivum* L. (Aestivicum Group) 'Abe']; and (3) pasture-type perennial ryegrass (*Lolium perenne* L. 'Linn'). Wheat and perennial ryegrass seeds are surface-sterilized with 1 percent sodium hypochlorite for 10 minutes and 5 minutes, respectively.

Each test compound is formulated in acetone and aliquots of the test formulation are placed on three layers of sterilized filter papers (Whatman No. 1, 8.26 cm diameter) in each petri dish. As soon as the acetone evaporates, 7 ml of deionized water are added into each petri dish with an appropriate automatic dispenser. Then, 5 to 8 wheat seeds, 10 to 15 perennial ryegrass seeds and 10 to 15 lettuce seeds are placed on the filter paper of each petri dish. Dishes are then covered and seeds are germinated for 3 days at 20° C. at a relative humidity of 65% in the dark. The dishes are then removed from the dark growth chamber and maintained in lighted environmental growth chambers for 4 days.

At the end of the seventh day of planting, growth and developmental responses/characteristics are evaluated.

The results are summarized in Table XIV.

TABLE XIV

| Compound Example No. | Rates (ug/dish) | Test Species[1] | | | | | |
|---|---|---|---|---|---|---|---|
| | | Lettuce | | Wheat | | Perennial Ryegrass | |
| | | Root | Stem | Root | Leaf | Root | Leaf |
| 14 | 500.00 | −3 | −3 | −3 | −3 | −3 | −3 |
| | 100.00 | 0 | −2 | −3 | −3 | −3 | −1 |
| | 50.00 | 0 | 0 | −3 | −1 | −3 | 0 |
| | 10.00 | 0 | 0 | 0 | 0 | 0 | 0 |
| | 1.00 | 0 | 0 | 0 | 0 | 0 | 0 |
| 22 | 500.00 | −2 | −3 | −3 | −3 | −3 | −3 |
| | 100.00 | 0 | −2 | −3 | −3 | −3 | −1 |
| | 50.00 | 0 | 0 | −3 | −2 | −3 | 0 |
| | 10.00 | 0 | 0 | 0 | 0 | 0 | 0 |
| | 1.00 | 0 | 0 | 0 | 0 | 0 | 0 |
| 30 | 500.00 | −3 | −3 | −3 | −3 | −3 | −3 |
| | 100.00 | −3 | −3 | −3 | −3 | −3 | −3 |
| | 50.00 | −3 | −3 | −3 | −3 | −3 | −3 |
| | 10.00 | −1 | −3 | −3 | −3 | −3 | −3 |
| | 1.00 | 0 | −3 | −3 | −2 | −3 | −2 |
| | 0.50 | 0 | −1 | −3 | −2 | −3 | −2 |
| | 0.10 | 0 | 0 | −1 | 0 | −2 | −2 |
| 67 | 100.00 | −3 | −3 | −3 | −3 | −3 | −3 |
| | 50.00 | −3 | −3 | −3 | −3 | −3 | −3 |
| | 10.00 | −2 | −3 | −3 | −3 | −3 | −3 |
| | 5.00 | 0 | −3 | −3 | −3 | −3 | −3 |
| | 1.00 | 0 | −2 | −3 | −2 | −2 | −2 |
| | 0.50 | 0 | −2 | −1 | −1 | −1 | −1 |
| | 0.10 | 0 | 0 | 0 | 0 | 0 | 0 |
| 73 | 500.00 | −3 | −3 | −3 | −3 | −3 | −3 |
| | 100.00 | −3 | −3 | −3 | −3 | −3 | −3 |
| | 50.00 | −3 | −3 | −3 | −3 | −3 | −3 |
| | 10.00 | −2 | −3 | −3 | −3 | −3 | −3 |
| | 1.00 | 0 | −2 | −2 | 0 | −2 | −2 |
| 92 | 500.00 | −3 | −3 | −3 | −3 | −3 | −3 |
| | 100.00 | −1 | −3 | −3 | −3 | −3 | −3 |
| | 50.00 | 0 | −3 | −3 | −3 | −3 | −3 |
| | 10.00 | 0 | −3 | −3 | −3 | −3 | −2 |
| | 1.00 | 0 | −2 | 0 | −1 | −1 | −1 |
| 108 | 500.00 | 0 | −3 | −3 | −3 | −3 | −3 |
| | 100.00 | −2 | −3 | −3 | −3 | −3 | −3 |
| | 50.00 | +3 | −3 | −3 | −3 | −1 | −2 |
| | 10.00 | +1 | −1 | 0 | 0 | 0 | 0 |
| | 1.00 | 0 | 0 | 0 | 0 | 0 | 0 |
| 114 | 500.00 | −3 | −3 | −3 | −3 | −3 | −3 |
| | 100.00 | −3 | −3 | −3 | −3 | −3 | −3 |
| | 50.00 | −3 | −3 | −3 | −3 | −3 | −3 |
| | 10.00 | 0 | −2 | −3 | −2 | −3 | −2 |
| | 1.00 | 0 | 0 | 0 | 0 | 0 | 0 |
| 122 | 500.00 | −3 | −3 | −3 | −3 | −3 | −3 |
| | 100.00 | −3 | −3 | −3 | −3 | −3 | −3 |
| | 50.00 | −3 | −3 | −3 | −3 | −3 | −3 |
| | 10.00 | −1 | −2 | −3 | −2 | −3 | −2 |
| | 1.00 | 0 | 0 | 0 | 0 | 0 | 0 |
| 137 | 500.00 | −1 | −3 | −3 | −3 | −3 | −3 |
| | 100.00 | −1 | −3 | −3 | −3 | −3 | −2 |
| | 50.00 | 0 | 0 | −3 | −2 | −3 | 0 |
| | 10.00 | 0 | 0 | −3 | −1 | −2 | 0 |
| | 1.00 | 0 | 0 | 0 | 0 | 0 | 0 |
| 142 | 500.00 | −3 | −3 | −3 | −3 | −3 | −3 |
| | 100.00 | −3 | −3 | −3 | −3 | −3 | −3 |
| | 50.00 | −3 | −3 | −3 | −3 | −3 | −1 |
| 157 | 10.00 | 0 | −1 | −3 | −1 | −1 | 0 |
| | 1.00 | 0 | 0 | 0 | 0 | 0 | 0 |
| | 500.00 | 0 | 0 | −3 | −3 | −3 | −1 |
| | 100.00 | 0 | 0 | −3 | −2 | −3 | 0 |
| | 50.00 | 0 | 0 | −3 | −2 | −3 | 0 |
| | 10.00 | 0 | 0 | −1 | 0 | −1 | 0 |
| | 1.00 | 0 | 0 | 0 | 0 | 0 | 0 |
| 161 | 500.00 | −2 | −3 | −3 | −3 | −3 | −2 |
| | 100.00 | 0 | −1 | −3 | −2 | −3 | −1 |
| | 50.00 | 0 | 0 | −3 | −2 | −1 | 0 |
| | 10.00 | 0 | 0 | 0 | 0 | 0 | 0 |
| | 1.00 | 0 | 0 | 0 | 0 | 0 | 0 |
| 177 | 500.00 | −3 | −3 | −3 | −2 | −3 | −3 |
| | 100.00 | 0 | −1 | −3 | −3 | −3 | −2 |
| | 50.00 | −3 | 0 | −3 | −3 | −3 | −2 |
| | 10.00 | 0 | 0 | −2 | −2 | 0 | −1 |
| | 1.00 | 0 | 0 | 0 | 0 | 0 | 0 |
| 191 | 500.00 | −3 | −3 | −3 | −3 | −3 | −3 |
| | 100.00 | −3 | −3 | −3 | −3 | −3 | −3 |
| | 50.00 | −3 | −3 | −3 | −3 | −3 | −3 |
| | 10.00 | −3 | −3 | −3 | −3 | −3 | −3 |
| | 1.00 | 0 | −2 | −3 | −2 | −3 | −3 |
| 193 | 500.00 | −3 | −3 | −3 | −3 | −3 | −3 |
| | 100.00 | −3 | −3 | −3 | −3 | −3 | −3 |
| | 50.00 | −3 | −3 | −3 | −3 | −3 | −3 |
| | 10.00 | −1 | −2 | −2 | 0 | −3 | −3 |
| | 1.00 | 0 | 0 | 0 | 0 | −2 | −2 |
| 197 | 500.00 | −3 | −3 | −3 | −3 | −3 | −3 |
| | 100.00 | −3 | −3 | −3 | −3 | −3 | −3 |
| | 50.00 | −1 | −2 | −3 | −2 | −3 | −2 |
| | 10.00 | −1 | −2 | −2 | 0 | −1 | 0 |
| | 1.00 | 0 | 0 | 0 | 0 | 0 | 0 |
| 201 | 500.00 | −3 | −3 | −3 | −3 | −3 | −3 |
| | 100.00 | −1 | −2 | −3 | −2 | −3 | −3 |
| | 50.00 | 0 | −2 | −3 | −2 | −2 | −2 |
| | 10.00 | 0 | 0 | 0 | 0 | 0 | 0 |
| 202 | 500.00 | −3 | −3 | −3 | −3 | −3 | −3 |
| | 100.00 | −3 | −3 | −3 | −3 | −3 | −3 |
| | 50.00 | −3 | −3 | −3 | −3 | −3 | −3 |
| | 10.00 | 0 | −1 | −2 | 0 | −2 | −1 |
| | 1.00 | 0 | 0 | 0 | 0 | 0 | 0 |
| 206 | 500.00 | −3 | −3 | −3 | −3 | −3 | −3 |
| | 100.00 | −2 | −3 | −3 | −3 | −3 | −3 |
| | 50.00 | −1 | −3 | −3 | −2 | −3 | −3 |
| | 10.00 | −1 | −3 | −3 | −3 | −2 | −1 |
| | 1.00 | 0 | 0 | 0 | 0 | 0 | 0 |
| 208 | 500.00 | −3 | −3 | −3 | −3 | −3 | −3 |
| | 100.00 | −3 | −3 | −3 | −3 | −3 | −3 |
| | 50.00 | −3 | −2 | −3 | −3 | −3 | −3 |
| | 10.00 | −2 | −3 | −3 | −3 | −2 | −1 |
| | 1.00 | 0 | 0 | 0 | 0 | 0 | 0 |
| 209 | 500.00 | −3 | −3 | −3 | −3 | −3 | −3 |
| | 100.00 | −3 | −3 | −3 | −3 | −3 | −3 |
| | 50.00 | −3 | −3 | −3 | −3 | −3 | −3 |
| | 10.00 | −3 | −2 | −3 | −3 | −3 | −2 |
| | 1.00 | 0 | 0 | −1 | 0 | 0 | 0 |
| 214 | 500.00 | −3 | −3 | −3 | −3 | −3 | −3 |
| | 100.00 | −3 | −3 | −3 | −3 | −3 | −3 |
| | 50.00 | −3 | −3 | −3 | −3 | −3 | −3 |
| | 10.00 | −2 | −2 | −2 | −2 | −2 | −2 |
| | 1.00 | 0 | 0 | 0 | 0 | 0 | 0 |
| 217 | 500.00 | −2 | −1 | −3 | −3 | −3 | −3 |
| | 100.00 | −1 | −1 | −3 | −3 | −3 | −2 |
| | 50.00 | 0 | −1 | −3 | −3 | −3 | −2 |
| | 10.00 | +1 | 0 | −2 | 0 | 0 | 0 |
| 218 | 500.00 | −2 | −2 | −3 | −3 | −3 | −3 |
| | 100.00 | 0 | −2 | −3 | −3 | −3 | −3 |
| | 50.00 | 0 | −2 | −3 | 0 | −3 | −2 |
| | 10.00 | 0 | 0 | −2 | 0 | 0 | 0 |
| | 1.00 | 0 | 0 | 0 | 0 | 0 | 0 |
| 220 | 500.00 | −3 | −3 | −3 | −3 | −3 | −3 |
| | 100.00 | −3 | −3 | −3 | −3 | −3 | −3 |
| | 50.00 | −3 | −3 | −3 | −3 | −3 | −3 |
| | 10.00 | 0 | −1 | −3 | −2 | −3 | −3 |
| | 1.00 | 0 | 0 | 0 | 0 | 0 | 0 |
| 221 | 500.00 | −2 | −3 | −3 | −3 | −3 | −3 |
| | 100.00 | 0 | −2 | −3 | −3 | −3 | −1 |

TABLE XIV-continued

| Compound Example No. | Rates (ug/dish) | Test Species[1] | | | | | |
|---|---|---|---|---|---|---|---|
| | | Lettuce | | Wheat | | Perennial Ryegrass | |
| | | Root | Stem | Root | Leaf | Root | Leaf |
| | 50.00 | 0 | −2 | −3 | −3 | −3 | −3 |
| | 10.00 | 0 | 0 | 0 | 0 | 0 | 0 |
| 223 | 500.00 | −3 | −2 | −3 | −3 | −3 | −1 |
| | 100.00 | −2 | −2 | −3 | −3 | −3 | −1 |
| | 50.00 | −1 | −1 | −3 | −2 | −2 | 0 |
| | 10.00 | 0 | −1 | −1 | 0 | 0 | 0 |
| | 1.00 | 0 | −1 | −1 | 0 | 0 | 0 |
| 227 | 500.00 | −3 | −3 | −3 | −3 | −3 | −3 |
| | 100.00 | −3 | −1 | −3 | −3 | −3 | −3 |
| | 50.00 | −1 | 0 | −3 | −3 | −1 | −1 |
| | 10.00 | 0 | 0 | −1 | 0 | 0 | 0 |

[1]Stem, root or leaf length measured 7 days after treatment.
[2]Ratings:
−1 or +1 = less than 30% inhibition (−) or stimulation (+) of growth compared to control.
−2 or +2 = 30% to 70% inhibition or stimulation.
−3 or +3 = greater than 70% inhibition or stimulation.

To illustrate the efficacy and broad spectrum of the plant growth regulant effects demonstrated by the compounds of the present invention, tests on specific plants to achieve specific plant growth regulant effects were conducted. The procedures and results of the various tests are described below.

Height Growth Regulation of Cotton Plants

Various compounds of the present invention were evaluated for the purpose of producing a shorter, more compact cotton plant by chemical treatment. The advantages to attaining plants of this stature are: ease of mechanical harvesting; increased pesticide, light and air penetration onto a more open canopy; decreased lodging; increased tolerance to high levels of nitrogen fertilization due to decreased rank growth.

Four 'Delta Pine 61' cotton plants per 5"×5" fiber pot were grown in standard pasteurized greenhouse soil under greenhouse conditions. Plants were thinned to 2 per pot approximately 2 weeks after planting and fertilized every 2 weeks thereafter.

Test solutions were either applied into the soil as a drench or sprayed onto the plant foliage one month after planting. At this time, cotton plants were in the 1–2 true leaf stage. Treatment volume was 5 mls which is equivalent to a 500 gal/A field rate when based on pot area. In the case of foliar spray treatments, which were applied with a cone-type nozzle at 12 psi, treatment volume was sufficient to wet all foliage without runoff. During the foliar spray treatments, a plexiglass shield covered the soil. Foliar treated plants were bottom watered subsequent to treatment to prevent chemical runoff.

Test solutions were prepared by dissolving 24 mg of chemical or acid equivalent, in the case of salt formulations, in 17.5 mls of acetone and diluting to 50 mls with water. Five mls (480 ppm) of this solution per pot was calculated to be equivalent to a 2 kg/ha rate when based on pot area. Appropriate dilutions were made with a 35% acetone solution to attain 1, ½, ¼ and ⅛ kg/ha rates. One half ml of 0.5% Triton X-155 (Triton X-155 and Triton X-114, as appearing herein, are alkylaryl polyether alcohol surfactants obtainable from Rohm & Haas Company) was added to each 5 mls of test solution. Control plants were either foliar sprayed or soil drenched with 35% acetone and 0.05% Triton X-155. All treatments were replicated twice.

Plant height was evaluated by measuring the distance from the soil surface to the plant apex at 0 and 3 weeks after treatment for foliar sprayed cotton, and at 0 and 5 weeks after treatment for soil treated cotton.

The compounds tested, application rates and results are summarized in Tables XV–XVII below. The data in these tables are expressed as the percent increase in height of treated plants as compared to control plants.

TABLE XV

The Effect of a Soil Drench of Diphenylpyridazinones on Cotton Height Growth[1] Five Weeks After Treatment

| Compound Example No. | 64 | 120 | 133 |
|---|---|---|---|
| Rates kg/ha | | | |
| 2 | 45.7 | 75.0 | 33.8 |
| 1 | 45.6 | 57.5 | 66.3 |
| Control | 100.0 | 100.0 | 100.0 |

[1]Expressed in terms of percent height of control.

TABLE XVI

The Effect of a Soil Drench of Diphenylpyridazinones on Cotton Height Growth[1] Five Weeks After Treatment

| Compound Example No. | 31 | 124 | 132 |
|---|---|---|---|
| Rates kg/ha | | | |
| 2 | 50.6 | 59.8 | 57.5 |
| 1 | 46.2 | 33.3 | 64.4 |
| ½ | 47.1 | 44.8 | 56.3 |
| Control | 100.0 | 100.0 | 100.0 |

[1]Expressed in terms of percent height of control.

TABLE XVII

The Effect of a Foliar Spray of Diphenylpyridazinones on Cotton Height Growth[1] Three Weeks After Treatment

| Compound Example No. | 30 | 124 |
|---|---|---|
| Rates kg/ha | | |
| ½ | NT[2] | 17.8 |
| ¼ | 16.8 | 23.6 |
| ⅛ | 29.9 | 55.7 |
| 1/16 | 35.5 | NT |
| Control | 100.0 | 100.0 |

[1]Expressed in terms of percent height of control.
[2]NT = Not Tested

Cotton Regrowth Control

Selected compounds of the present invention were tested for chemically controlling vegetative growth of cotton subsequent to a defoliation treatment. Regrowth is undesirable because it decreases mechanical harvesting efficiency, lowers fiber quality by adding a green stain to cotton fibers and/or providing moisture which can cause fiber deterioration during the preginning stage.

Mature cotton plants (2 per 5"×7" fiber pot) were sprayed with a 2 lb a.i./A rate of Mobay DEF 6 EC (S,S,S-Tributyl phosphorotrithioate defoliant, Emulsifiable containing 6 pounds active ingredient per gallon) using a carbon dioxide back pack sprayer at 20 psi and a 2E nozzle attachment. Test solutions were prepared by dissolving an appropriate amount of weighed chemical in 6.25 mls of acetone and diluting to 25 mls with water. One ml of 0.5% Triton X-155 was added to each 25 mls of test solution. Test rates were based on a field plant area basis (1 plant per sq. ft.) such that 2 kg/ha was calculated to be equivalent to 37 mg per 2 plants. Test solutions were applied into the soil as a drench just prior to defoliation. Control plants were soil drenched with 25 mls of a 25% acetone solution containing 0.02% Triton X-155. All treatments were replicated twice. Eight weeks after treatment regrowth was excised from all plants and weighed.

The following table illustrates the results obtained.

TABLE XVIII

Effect of a soil drench treatment of diphenylpyridazinones on regrowth of defoliated cotton eight weeks after treatment.

| Compound Example No. Rate (kg/ha) | Regrowth Fresh Weight[1] (% of control) |
|---|---|
| 30 | |
| 2 | 0.9 |
| 1 | 61.3 |
| ¼ | 44.1 |
| 1/16 | 75.3 |
| 31 | |
| 2 | 2.9 |
| 1 | 24.9 |
| ½ | 7.8 |
| ¼ | 42.2 |
| Control | 100.0 |

[1]Data are an average of 2 plants/pot, in 2 replications.

Selected compounds of the present invention were tested according to the procedure described above except: compound of Example 132 was formulated by dissolving the required amount of compound in 10.5 mls of acetone and diluting to 30 mls with water to attain the appropriate test rates. The compound of Example 64 was formulated as a 10% flowable (w/w) and diluted to 30 mls with a 1% base formulation minus active ingredient to attain the appropriate test rates. Regrowth was evaluated by the method described previously one month after treatment.

The following table illustrates the results obtained:

TABLE XIX

Effects of a soil drench treatment of diphenylpyridazinones on regrowth of defoliated cotton four weeks after treatment.

| Compound Example No. Rate (kg/ha) | Regrowth Fresh Weight[1] (% of control) |
|---|---|
| 64 | |
| 4 | 28.6 |
| 132 | |
| 4 | 0.0 |
| Control | 100.0 |

Compounds of the present invention were further tested by the procedure described above except that test solutions were applied as a foliar spray treatment with an air brush at 12 psi 12 days after defoliation. At this time mature cotton leaves had abscissed and new leaves (regrowth) were beginning to emerge. The compound of Example 31 was formulated as a 2 EC and diluted with water to attain appropriate rates. An appropriate amount of the compound of Example No. 124 was weighed and diluted to 9 mls with water and 1 ml of 10% Triton X-114 was added. Treatment volume was 10 mls which is equivalent to a 57 gal/A rate. Regrowth was evaluated by the method previously described one month after treatment.

The following table illustrates the results obtained:

TABLE XX

The effect of a foliar spray treatment of diphenylpyridazinones on regrowth of defoliated cotton one month after treatment.

| Compound Example No. Rate (kg/ha) | Regrowth Fresh Weight[1] (% of control) |
|---|---|
| 30 | |
| 4.0 | 30.0 |
| 2.0 | 73.1 |
| 1.0 | 75.6 |
| 0.5 | 61.9 |
| 124 | |
| 4.0 | 34.0 |
| 2.0 | 106.8 |
| 1.0 | 110.1 |
| 0.5 | 83.6 |
| Control | 100.0 |

Growth Regulation of Ornamental Plants

The compounds of the present invention were evaluated for producing ornamental plants which are more aesthetically satisfying to consumers.

Commercially grown chrysanthemums (5 plants per 6-inch diameter pot) were purchased and subsequently grown in a growth room under artificial light. Terminal buds were removed by pinching and the plants sprayed with test solutions when new lateral shoots had grown to approximately 2 inches long. Test solutions were prepared by dissolving 18 mg of chemical in 50 mls of acetone and diluting to 100 mls with water. Ten mls (180 ppm) of this solution per pot was calculated to be equivalent to 1 kg/ha when based on pot area. Appropriate dilutions were made with a 50% acetone solution to attain 0.5 and 0.25 kg/ha rates. One half ml of 0.5% Triton X-155 was added to each 10 mls of test solution. A-Rest, a commercial standard by Eli Lily was prepared by diluting 6.8 mls of the product to 10 mls with a 50% acetone to attain a 1 kg/ha rate. Appropriate dilutions were made with a 50% acetone solution to attain 0.5 and 0.25 kg/ha rates. Test solutions were sprayed onto plants with a cone-type nozzle air gun at 15–20 psi. All treatments were replicated twice. Control plants were sprayed with 10 mls of 50% acetone. Plant height was evaluated 8 weeks after treatment by measuring the distance between the soil level and the top of the plants.

Morphological changes of treated plants were observed as early as 2 to 3 weeks after chemical treatment. A reduction in plant height and enhancement of green leaf color in treated plants as compared to control plants was observed. The compounds of the invention tested, application rates and the results are summarized in Table XXI below.

TABLE XXI

The Effect of a Foliar Spray Treatment on Chrysanthemum Height Growth Eight Weeks After Treatment

| Compound Example No. Rate (kg/ha) | Average Height (% of control) |
|---|---|
| 30 | |
| 1.0 | 75 |
| 0.5 | 81 |
| 0.25 | 80 |
| 31 | |
| 1.0 | 85 |
| 0.5 | 96 |
| 0.25 | 100 |
| 68 | |
| 1.0 | 63 |

TABLE XXI-continued

The Effect of a Foliar Spray Treatment on
Chrysanthemum Height Growth Eight Weeks After Treatment

| Compound Example No. Rate (kg/ha) | Average Height (% of control) |
|---|---|
| 0.5 | 73 |
| 0.25 | 79 |
| A-REST* | |
| 1.0 | 75 |
| 0.5 | 80 |
| 0.25 | 83 |
| Control | 100 |

*trademark

Control of Algal Population Growth

The invention compounds were evaluated for ability to reduce algal population in recreational and other waters.

*Chlamydomonas reinhardi* [wt. (+)] were grown in synchromonous culture using a basal salt medium supplemented with acetate at pH 7.2. Cells grown to approximately $2 \times 10^6$ per ml were diluted to $2.5 \times 10^5$ cells per ml with algal growth media. Ten mls of algal culture was dispensed into 25 ml Erlenmeyer flasks. Test solutions were prepared by solubilizing a weighed amount of test compound in 10 mls of dimethylsulfoxide (DMSO) to yield a $10^{-2}$M concentration. Appropriate dilutions were made with DMSO to attain decreasing chemical concentrations. A 0.1 ml aliquot of test solution was added to each flask. Control flasks received 0.1 ml of DMSO. Flasks were plugged with cotton and all procedures were performed under sterile conditions. All treatments were replicated twice. Algal cultures were allowed to incubate in the presence of the chemical for 2.5 days in a water bath-shaker at 25° C. under a 12 hr. light/12 hr. dark cycle. At the end of the incubation period, the algal growth was terminated by adding 0.5 mls of 50% w/v gluteraldehyde to each test flask. The number of algal cells per ml of culture in treated vs. control flasks was determined by replicate counting with a hemacytometer.

The following table illustrates the results obtained:

TABLE XXII

| Compound Example No. Rate × $10^{-6}$ M | % Inhibition |
|---|---|
| 31 | |
| 60.0 | 100.0 |
| 30.0 | 97.5 |
| 15.0 | 73.3 |
| 7.5 | 51.0 |
| 3.8 | 5.3 |
| 0.0 | 0.0 |
| 30 | |
| 8.0 | 100.0 |
| 4.0 | 94.1 |
| 2.0 | 49.7 |
| 1.0 | 7.7 |
| 0.0 | 0.0 |

Soybean Growth Regulator and Yield Enhancement

The diphenylpyridazinones of the present invention have been found to be effective in regulating the growth of leguminous plants, especially soybean. Among the growth regulatory effects which can be observed are: height reduction, inhibition of terminal and axillary bud growth, reduced leaf size, curled leaves and dark green-colored leaves.

Soybean plants, especially indeterminate types of soybeans, produce unnecessary vegetative growth during the reproductive growth stage of development. The unnecessary vegetative growth includes terminal bud growth and branching during the reproductive growth stages. This growth does not contribute to the yield, but reduces the yield of soybean. By inhibiting such unnecessary vegetative growth, more photosynthates and nutrients can be translocated to yield components such as the pod, thus improving the "harvest index" of the soybean. Such growth inhibition can also improve water economy of soybean plants and prevent senescence during reproductive stages, leading to a yield increase.

'Beeson' soybean was grown in greenhouse and sprayed with various formulations of selected compounds of the present invention at the V2 stage, Fehr et al., "Stages of Soybean Development," *Special Report 80*, Cooperative Extension Service, Iowa State Univ., Ames, Iowa (1979), of soybean development. Three to four weeks later, increases in height and other morphologial changes were recorded. Percent height inhibition was calculated by the formula:

$$\% \text{ height inhibition} = \frac{\Delta HC - \Delta HT}{\Delta HC} \times 100$$

where $\Delta$ HC is an increase in average height of untreated control plants and $\Delta$ HT is an increase in average height of treated soybean plants. The results of this test are summarized in Table XXIII to follow.

In another experiment, greenhouse grown Beeson soybean plants at V3 stage of development were sprayed with various formulations of compounds of the invention to evaluate changes in the harvest index.

Harvest index was calculated by the formula:

$$\text{Harvest index} = \frac{\text{Total pod dry weight per treatment}}{\text{Total aerial dry weight per treatment}}$$

The results of this experiment are set out in Table XXIV below.

TABLE XXIII

Inhibition of height growth of Beeson soybean by selected diphenylpyridazinone formulations.

| Compounds Example No. | Formulation | Rate (kg/ha) | Treatment Period (Weeks) | Height Inhibition (% Control) |
|---|---|---|---|---|
| 30 | 35% acetone solution | 1/32 | 3 | 75 |
|  | emulsifiable concentrate | 1/32 | 3 | 87 |
|  | flowable | 1/32 | 3 | 24 |
| 31 | 35% acetone solution | ⅛ | 3 | 79 |
|  | flowable | ⅛ | 3 | 40 |

TABLE XXIII-continued

Inhibition of height growth of Beeson soybean by selected diphenylpyridazinone formulations.

| Compounds Example No. | Formulation | Rate (kg/ha) | Treatment Period (Weeks) | Height Inhibition (% Control) |
|---|---|---|---|---|
| 124 | diethanolamine salt solution | ¼ | 4 | 80 |
| 132 | Sodium salt solution | ¼ | 4 | 37 |
|  | Duomeen salt solution | ¼ | 4 | 36 |
| 64 | 35% acetone solution | ¼ | 3 | 74 |
|  | flowable | ¼ | 3 | 21 |
| 120 | diethanolamine salt solution | ¼ | 3 | 77 |
| 133 | Sodium salt solution | ¼ | 3 | 55 |
| 113 | Potassium salt solution | ¼ | 3 | 51 |
| Control | Duomeen salt solution | ¼ | 3 | 58 |

TABLE XXIV

Effect of compound formulations on harvest index of Beeson soybean

| Compound Example No. | Formulation | Rate (lb/A) | harvest index |
|---|---|---|---|
| Control |  | 0.00 | 0.51 |
| 31 | 50% acetone solution | 0.10 | 0.53 |
| 121 | dimethylpiperidine salt solution | 0.05 | 0.55 |
| 124 | diethanolamine salt solution | 0.10 | 0.60 |

Soybean plants were sprayed at the V3 stage.

Harvest index = $\frac{\text{Pod dry weight}}{\text{Aerial dry weight}}$

Rates based on 4 plants/square foot

Field experiments were conducted to demonstrate yield increases by selected diphenylpyridzainones of the present invention. The selected compounds were applied during the late reproductive stages of the soybean plant. An indeterminate cultivar, Williams soybean (group III), was sprayed with selected compounds at various rates during the R5 (beginning seed stage) and the R6 (full seed stage) reproductive stages of the soybean plant. Results of the experiments are shown in the following table:

TABLE XXX

Effect of Selected Diphenylpyridazinones on Soybean Yield Expressed as % of the Control

| Compound Example No. | Stages of Development | Rates (lb./A) | | | | | |
|---|---|---|---|---|---|---|---|
|  |  | 0.02 | 0.03 | 0.067 | 0.1 | 0.2 | 0.3 |
| 31 | R5 | 115 |  | 107 |  | 112 |  |
|  | R6 | 90 |  | 100 |  | 108 |  |
| 30 | R5 |  | 98 |  | 103 |  | 104 |
|  | R6 |  | 92 |  | 109 |  | 110 |
| 64 | R6 |  | 114 |  | 108 |  | 127 |

Tobacco Sucker Control

Current cultural practices of tobacco production involves topping of flowers or flower buds during the harvest season. Removal of flowers increases yield of tobacco, improves quality of cured leaves and prevents lodging of tobacco plants. Such topping, however, breaks apical dominance of the plants. The immediate plant response to this procedure is the growth of axillary buds, called "suckers," which have been suppressed by the shoot apex. These suckers can be removed by hand after they grow out 2-4 inches or their growth can be suppressed by chemical inhibitors. Due to high labor costs, use of chemical sucker control agents has become the procedure of choice in most parts of tobacco growing areas in this country.

Diphenylpyridazinones of the present invention have demonstrated high sucker control activity in greenhouse tests. The compounds of Example Nos. 30, 31, 124, 64, 120, 113 and 67 were selected, on the basis of the results of the primary plant growth regulant screen, to treat greenhouse-grown burley or flue-cured tobacco plants.

The final formulation of each compound contained 0.05 to 0.2% Triton X-114 or 0.025% Triton X-155. Commercial varieties of burley or flue-cured tobacco were grown in a greenhouse at a final size of ¼ to ½ of the field-grown plants. Five to 20 ml of test formulations were sprayed on the center of each topped plant or drenched into soil of each pot containing a topped plant at button, early flower or late flower stage. Control of the top 5 suckers were evaluated 21 to 42 days after treatment and % control was calculated by the formula:

$$\% \text{ control} = \frac{TNS - TR + |TNS - TR|}{2\ TNS} \times 100$$

where TNS is the fresh weight of suckers of the topped check and TR is the fresh weight of suckers of the treated plants. The top 5 suckers have the greatest potential to regrow after topping of flower bud or flowers.

The activity of the particular diphenylpyridazinone depended on types of formulation, application volume, method of application, developmental stages of the tobacco plant when a treatment was made, kinds and concentration of additives in the final formulation, treatment period and type of tobacco. The results for the selected compounds and the test parameters are summarized in Tables XXV and XXVI that follow.

TABLE XXV

Sucker control activity of selected diphenylpyridazinones and their formulations in flue-cured tobacco.

| Compound Example No. | Formulation | A.I. Dosage mg/plant[6] | Method of application[7] | Developmental stage at treatment[8] | Treatment Period (days) | Control of Top 5 suckers (%) |
|---|---|---|---|---|---|---|
| 30 | 50% acetone | 5.2 | FS | button-early | 21 | 0 |
| 30 | 50% acetone | 20.8 | FS | button-early | 35 | 0 |
| 30 | EC[1] | 10.4 | FS | full | 35 | 53 |
| 30 | EC | 20.8 | FS | button | 35 | 100 |
| 30 | EC | 41.6 | FS | early | 35 | 100 |

TABLE XXV-continued

Sucker control activity of selected diphenylpyridazinones and their formulations in flue-cured tobacco.

| Compound Example No. | Formulation | A.I. Dosage mg/plant[6] | Method of application[7] | Developmental stage at treatment[8] | Treatment Period (days) | Control of Top 5 suckers (%) |
|---|---|---|---|---|---|---|
| 30 | 50% acetone | 20.8 | SD | button-early | 21 | 93 |
| 31 | 50% acetone | 20.8 | FS | button-early | 21 | 93 |
| 31 | 50% acetone | 10.4 | SD | button-early | 21 | 99 |
| 31 | 50% acetone | 5.2 | SD | button-early | 21 | 79 |
| 31 | 50% acetone | 2.6 | SD | button-early | 21 | 5 |
| 31 | diethanolamine | 32 | FS | full | 35 | 24 |
| 124 | salt solution | | | | | |
| 31 | " | 32 | SD | full | 35 | 14 |
| 124 | potassium | | | | | |
| 31 | salt solution | 40 | FS | full | 35 | 3 |
| 31 | " | 20 | SD | full | 35 | 0 |
| 64 | diethanolamine | 43.2 | FS | early | 42 | 100 |
| 120 | salt solution | 32 | FS | early | 35 | 89 |
| | | 16 | FS | early | 35 | 45 |
| | | 8 | FS | full | 35 | 0 |
| | | 16 | SD | early | 35 | 68 |
| 64 | diethanol amine | 43.2 | SD | early | 42 | 99 |
| 120 | salt solution | | | | | |
| 64 | potassium salt | 20 | SD | full | 35 | 33 |
| 113 | solution | | | | | |
| 67 | EC | 43.2 | FS | full | 42 | 100 |
| | EC | 21.6 | FS | full | 42 | 100 |
| | EC | 10.8 | FS | full | 42 | 100 |
| MH[2] | diethanol amine | 20.8 | FS | button-early | 21 | 35 |
| (MH-30) ®[3] | salt solution | 5.2 | FS | button-early | 21 | 0 |
| (Royal MH-30) ®[4] | Potassium salt | 41.6 | FS | early | 35 | 97 |
| | solution | 83.2 | FS | early | 35 | 100 |
| | | 85.5 | FS | full | 42 | 99 |
| OST[5] | EC | 10 ml 4% | FS | | 35 | 8 |

[1]EC = Emulsifiable concentrate.
[2]MH = Maleic hydrazide.
[3]MH-30 ® = Diethanolamine salt of maleic hydrazide.
[4]Royal MH-30 ® = Potassium salt of maleic hydrazide.
[5]OST = Off-shoot-T ®, a commercial standard.
[6]A.I. Dosage mg/plant = Active ingredient dosage; milligram/plant.
[7]FS = Foliar spray.
SD — Soil drench.
[8]button-early = Button to early flower stage of tobacco development.
early = Early flower stage.
full = Full flower stage.

TABLE XXVI*

Sucker control activity of selected diphenylpyridazinones their formulations in burley tobacco.

| Compound Example No. | Formulation | A.I. Dosage mg/plant[6] | Method of application[7] | Treatment stage[8] | Treatment Period (days) | Control of top 5 suckers (%) |
|---|---|---|---|---|---|---|
| 30 | 50% acetone | 5.2 | FS | button-early | 21 | 72 |
| | 50% acetone | 20.8 | SD | button-early | 21 | 99 |
| | emulsifiable concentrate | 2.7 | FS | button | 31 | 43 |
| | emulsifiable concentrate | 5.4 | FS | button | 31 | 100 |
| | emulsifiable concentrate | 21.6 | FS | button | 31 | 100 |
| 31 | 50% acetone | 20.8 | FS | button-early | 21 | 100 |
| | 50% acetone | 10.4 | SD | button-early | 21 | 86 |
| 124 | diethanolamine salt | 10.4 | FS | button | 31 | 11 |
| 64 | diethanolamine salt | 5.2 | FS | button | 31 | 61 |
| 120 | solution | 10.4 | FS | button | 31 | 88 |
| 67 | emulsifiable concentrate | 2.7 | FS | button | 31 | 84 |
| | | 5.4 | FS | button | 31 | 85 |
| | | 10.8 | FS | button | 31 | 100 |
| | | 21.6 | FS | button | 31 | 100 |
| MH[2] | potassium salt | 42.8 | FS | button | 31 | 99 |
| (Royal MH-30) ®[4] | solution | 85.5 | FS | button | 31 | 100 |

*See footnotes of Table XXV.

Greenhouse Screening of Selected Diphenylpyridazinones for Tobacco Sucker Control Activity Flue-cured tobacco plants were grown in the greenhouse until maturity. Two plants were topped at the button stage (a tobacco developmental stage showing flower bud formation) and grown for 6–8 days until the top-most leaf span reached 6–8 inches and the top-most sucker growth reached 1–3 inches. The plants at this stage are very similar to field-grown plants in the early flower stage. If the plants at the button stage are not topped but grown further in the greenhouse, they will reach the early flower stage in 6–8 days. These plants are referred to as early topped early flower stage plants.

Another two plants at the button stage of tobacco development were topped before chemical application.

The selected pyridazinone compounds were formulated as a 6% EC (emulsifiable concentrate). One early topped early flower stage plant and one button stage plant were sprayed with each compound at 1.5 mg or 3 mg per plant, except the compound of Example 38 (sprayed at 3 mg or 6 mg per plant). Each compound to be tested was formulated into a 10 ml emulsified solution with a constant surfactant concentration for both rates of application. The test formulations were sparyed with a Hudson Hydragun ® on the center of each plant. The nozzle of the Hydragun was adjusted to generate a coarse spray.

Sucker control was evaluated 5 weeks after treatment. Suckers from the top 5 nodes were counted and fresh weights of the sucker from the control (topped check) and the treated were determined. Also malformation of top 3 leaves of plants sprayed at the button stage was evaluated as follows:

| Rating Number | Degree of Malformation |
| --- | --- |
| 0 | None |
| 1 | Very Slight |
| 2 | Slight |
| 3 | Moderate |
| 4 | Severe |
| 5 | Very Severe |

% sucker control was calculated as follows:

$$\% \text{ control} = \frac{TNS - TR + |TNS - TR|}{2\ TNS} \times 100$$

(This formula defined on page 113.)

Results for the selected compounds and the test parameters are summarized in Table XXXI which follows.

TABLE XXXI

Tobacco Sucker Control and the Respective Malformation for Selected Diphenylpyridazinones

| Compound Example No. | A.I. Dosage mg/plant[1] | Control of top 5 suckers (%) | Malformation |
| --- | --- | --- | --- |
| 30 | 3 | 55 | 3 |
|  | 1.5 | 20 | 3 |
| 39 | 3 | 39 | 3 |
|  | 1.5 | 21 | 0 |
| 44 | 3 | 50 | 1 |
|  | 1.5 | 43 | 3 |
| 37 | 3 | 60 | 5 |
|  | 1.5 | 67 | 0 |
| 56 | 3 | 66 | 1 |
|  | 1.5 | 13 | 3 |
| 41 | 3 | 45 | 3 |
|  | 1.5 | 40 | 3 |
| 33 | 3 | 16 | 0 |
|  | 1.5 | 34 | 3 |
| 45 | 3 | 78 | 0 |
|  | 1.5 | 32 | 0 |
| 68 | 3 | 83 | 3 |
|  | 1.5 | 44 | 3 |
| 60 | 3 | 54 | 3 |
|  | 1.5 | 29 | 0 |
| 204 | 3 | 48 | 0 |
|  | 1.5 | 22 | 0 |
| 73 | 3 | 71 | 0 |
|  | 1.5 | 70 | 0 |
| 74 | 3 | 61 | 5 |
|  | 1.5 | 75 | 3 |
| 40 | 3 | 37 | 0 |
|  | 1.5 | 35 | 0 |
| 191 | 3 | 50 | 0 |

TABLE XXXI-continued

Tobacco Sucker Control and the Respective Malformation for Selected Diphenylpyridazinones

| Compound Example No. | A.I. Dosage mg/plant[1] | Control of top 5 suckers (%) | Malformation |
| --- | --- | --- | --- |
|  | 1.5 | 53 | 0 |
| 82 | 3 | 44 | 3 |
|  | 1.5 | 45 | 3 |
| 38 | 6 | 74 | 0 |
| 193 | 3 | 66 | 3 |
|  | 1.5 | 49 | 0 |
| 195 | 3 | 53 | 0 |
|  | 1.5 | 49 | 0 |

[1]A.I. Dosage mg/plant = Active Ingredient Dosage; in milligrams/plant

Turfgrass Retardation

The maintenance of turfgrasses and other ground covers employed for functional and esthetic purposes for residential buildings, institutions, golf courses, highways and other areas includes regular mowing by mechanical devices. mechanical mowing requires a considerable amount of labor and fuel costs. Both labor and fuel requirements can be saved significantly by chemical grass retardation. The compounds employed in this invention show novel compositions in that none of the structures disclosed in prior art act as turfgrass retardants.

Compounds that exhibit good turfgrass retardant activity from the primary screen (the petri dish test) were subject to a secondary pan test. Six to 10 week old turfgrasses (a Kentucky bluegrass and a creeping fine fescue) were cut to 2 cm and treated with test formulations. A test formulation consisted of 50% acetone in water, active ingredient, and 0.025% Triton X-155. The test formulation was sprayed on leaves or soil-drenched at 460 gal/A carrier volume. Inhibition of height growth and phytotoxicity were evaluated 4 weeks after treatment. Percent height inhibition was calculated by the formula:

$$\% \text{ height inhibition} = \frac{\Delta HC - \Delta HT}{\Delta HC} \times 100$$

where $\Delta$ HC is an increase in average height of a check turfgrass and $\Delta$ HT is an increase in average height of a treated turfgrass. Retardant activity and also phytotoxicity will depend on type of formulation, application volume, method of application, kinds and concentration of additives in the final formulation, treatment period, type of turfgrasses and various other factors known to those skilled in the art.

The compounds tested, including a commercial standard (Embark, registered trademark of 3M Company), the test species, application rates and results are summarized in Table XXVII below.

TABLE XXVII

Turfgrass retardant activity of selected diphenylpyridazinones for four weeks.

| | % Height Inhibition (phytotoxicity 0–5)[1] | | | |
| --- | --- | --- | --- | --- |
| | Test Species | | | |
| | Kentucky Bluegrass | | Creeping Fine Fescue | |
| Compound | Rate (kg/ha) | | | |
| Example No. | 1 | 0.5 | 1 | 0.5 |
| 74 | 84 (3) | 47 (0) | 79 (1) | 64 (0) |
| 64 | 79 (3) | 74 (1) | 86 (1) | 86 (0) |
| 80 | 89 (3) | 79 (1) | 86 (1) | 79 (0) |
| 67 | 79 (1) | 68 (0) | 86 (1) | 79 (0) |

TABLE XXVII-continued

Turfgrass retardant activity of selected diphenylpyridazinones for four weeks.

| Compound Example No. | % Height Inhibition (phytotoxicity 0-5)[1] | | | |
|---|---|---|---|---|
| | Test Species | | | |
| | Kentucky Bluegrass | | Creeping Fine Fescue | |
| | Rate (kg/ha) | | | |
| | 1 | 0.5 | 1 | 0.5 |
| 75 | 89 (2) | 47 (1) | 93 (1) | 86 (0) |
| 78 | 84 (2) | 84 (1) | 71 (1) | 79 (1) |
| EmbarK* ® | 84 (3) | 79 (2) | 86 (2) | 71 (1) |

*Commercial Standard
Phytotoxicity Ratings are as follows:
0 = no phytotoxicity
1 = slight leaf tip burn
2 = severe tip burn
3 = 25–50% leaf dead
4 = 50–75% leaf dead
5 = 75–100% leaf dead

The Effect of Selected Diphenylpyridazinones on Woody Perennial Growth

It has been discovered that diphenylpyridazinones of the present invention can be useful for controlling the growth an morphology of woody perennial plant species. As plant growth regulants, these agents may act to chemically prune woody ornamental species. With an enhancement of foliar uptake, these pyridazinones may effectively control the growth of brush in right-of-way applications.

Testing was performed to provide information concerning the effects of selected diphenylpyridazinones on woody perennial growth. A tree and a shrub species were selected along with two diphenylpyridazinone acids for greehouse experimental models.

Thirty, seven to nine foot tall hybrid poplars and thirty red twig dogwoods (*Cornus sericea*) were obtained for this test. The poplars, stored barerooted over winter, were repotted in a soil-potting blend mixture in 11 inch plastic pots. Each tree was trimmed to a six foot height where no buds had yet broken. Likewise, the fresh field-dug dogwoods were potted and trimmed back to a 24 inch branch length. One tablespoon of Peter's slow release fertilizer (Osmocote) was added to each pot. The plants were watered for ten minutes every two hours using an aerial sprinkler system.

After one month in the greenhouse, selected plants were treated with either the compound of Example 31 or the compound of Example 64 by application as soil drenches. Treatment solutions of 200 ml were prepared using 10% (W/W) flowable concentrates. Chemical treatments at 8, 2 or 0.4 lb/A were based on a pot area of $1.4 \times 10^{-5}$ acres. Following the treatments, the plants were placed outside the greenhouses. The treatments applied to the different species and number of each species is set out in Table XXXII which follows:

TABLE XXXII

| Compound Example No. | Rate | Test Species | |
|---|---|---|---|
| | | Poplars | Dogwoods |
| 31 | 8 | 4 | 4 |
| | 2 | 4 | 4 |
| | 0.4 | 3 | 4 |
| 64 | 8 | 4 | 4 |
| | 2 | 4 | 4 |
| | 0.4 | 3 | 4 |
| Control | — | 5 | 6 |

Chemical treatments were reapplied a month later to ensure thorough chemical exposure.

Four months following the initial treatment, growth of the individual poplars was measured. For the poplars, total branch length, total branch dry weight and total number of branches were measured. Since the growth measurement of the dogwoods was more complex, an estimate of the total shrub volume was taken. The maximum width in perpendicular directions in the same plane was measured along with the height above the crown 19 weeks posttreatment.

The results for this testing are set out in Table XXXIII and Table XXXIV that follow.

TABLE XXXIII

Poplar Tree Growth as Influenced by Selected Diphenylpyridazinone Soil Drenches

| Compound[1] Example No. | Rate (lb/A) | Branch | | |
|---|---|---|---|---|
| | | Number | Length (m) | Dry Weight (GM) |
| Control | 0 | 16.5 | 12.7 | 140 |
| 64 | 8.0 | 18.2 | 11.2 | 116 |
| 64 | 2.0 | 12.8 | 9.27 | 98 |
| 64 | 0.5 | 15.3 | 12.9 | 158 |
| 31 | 8.0 | 11.3 | 3.08[2] | 27[2] |
| 31 | 2.0 | 16.5 | 12.8 | 137 |
| 31 | 0.5 | 18.0 | 13.1 | 132 |

[1]Formulated as a 10% (W/W) flowable
[2]Statistically significant difference from that of the check at 95% confidence level using DNMR

TABLE XXXIV

Dogwood Shrub Growth as Influenced by Selected Diphenylpyridazinone Soil Drenches

| Compound[1] Example No. | Rate (lb/A) | Shrub Volume ($m^3$) Average | Inhibition % |
|---|---|---|---|
| Control | 0 | 2.05 | (0) |
| 64 | 8.0 | 0.50 | 76 |
| 64 | 2.0 | 1.45 | 29 |
| 64 | 0.5 | 2.41 | −18 |
| 31 | 8.0 | 0.46 | 88 |
| 31 | 2.0 | 0.83 | 59 |
| 31 | 0.5 | 1.08 | 47 |

[1]Formulated as 10% (W/W) flowable
[2]Reduced root development

As is evident from the data set forth herein, the compounds of the present invention demonstrate excellent herbicidal activity and broad spectrum plant growth regulant activity at relatively low application rates. Other than the seven plant growth regulant utilities illustrated previously, the compounds of the present invention can have plant growth regulant utility in numerous other areas among which there may be especially mentioned stimulation of cotton boll opening for yield enhancement and harvest efficiency improvement, tree growth retardation for reduced pruning and reduction of maintenance, sugar cane growth regulation for increased sugar content, control of bud-breaking in fruit trees for reduced damage from frost, sprout control for onions, potatoes and other stored vegetables to improve quality, growth regulation of corn and small grains for yield enhancement and growth regulation of the potato plant for yield enhancement. Also, compounds of the invention can find use for sugar beet bolting control to increase the sugar beet yield as well as the sugar content; and, in addition, to control the weed beet plant. Similar to the concept for tobacco sucker control, control of the sugar beet flower bud can increase the size of the sugar beet root and the sugar content in the root. Also by controlling flower and seed head formation, control of weed beets, which is a severe problem in current sugar beet production in Europe, can be accomplished during the next growing season.

Other areas where the compounds of the present invention may find use are banana sucker control, to increase yield of the mother plant and to speed up growth of a daughter plant; tree and hedge growth retardation and brush control for industrial areas and under powerlines; growth retardation of ground covers for park, railroads, highways, fence rows, airports, ditches, industrial open areas, and the like; growth retardation of cover crops in orchards, no-till farmlands and soil conservation; yield enhancement for such crops as (a) alfalfa—increase in branching, (b) small grains—reduced stature and reduced lodging, (c) sugarcane—inhibition of flowering, (d) peanut—inhibition of unnecessary vegetative growth, and (e) sunflower—reduced stature and reduced lodging; malesterilant or gametocyte for hybrid seed production; tree sucker control; chemical flower and fruit thinning; stem thickening for bean sprouts, asparagas, etc.; vine control for grapes; inhibition of rhizomes; and control of seed germination. Clearly, the biologist working in this field of technology will recognize the wide plant growth regulant utilities for these compounds.

While the invention has been described and illustrated with reference to certain preferred embodiments thereof, those skilled in the art will appreciate that various changes, modifications and substitutions can be made therein without departing from the spirit of the invention. For example, application rates other than those preferred ranges set forth hereinabove may be applicable due to variations in soils and planting characteristics, etc. Moreover, the specific results observed with respect to broadleaf and grass weed control as well as crop selectivity may vary depending on the specific active compounds selected and whether same are used alone or in combination with each other, i.e., mixture, or other known agents. Also, the specific formulation and the manner of applying same, e.g., soil drench, foliar spray, etc., may affect results. Accordingly, such expected changes and variations in results are contemplated in accordance with the objects and practices of the present invention. It is intended, therefore, that the invention be limited only by the scope of the claims which follow.

What is claimed is:

1. A herbicidal composition comprising a herbicidally acceptable carrier substance and a herbicidally effective amount of at least one active compound of the formula:

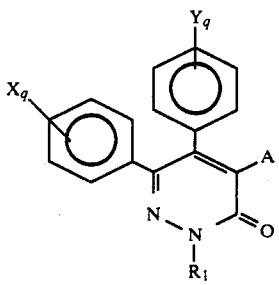

or the salts and the water hydrates thereof wherein the active compound is selected from the group consisting of Ethanol, 2-(5-cyano-1,6-dihydro-6-oxo-3,4-diphenyl-pyridazin-1-yl); Acetic Acid, 5-cyano-1,6-dihydro-6-oxo-3,4-diphenyl-pyridazin-1-yl; Acetic Acid, 5-cyano-1,6-dihydro-6-oxo-3,4,-diphenylpyridazin-1-yl ethyl ester, Propionic Acid, 3-(5-cyano-1,6-dihydro-6-oxo-3,4-diphenylpyridazin-1-yl); Propionic Acid, 3-(5-cyano-1,6-dihydro-6-oxo-3,4-diphenyypyridazin-1-yl)-ethyl ester; Propionic Acid, 3-(5-cyano-1,6-dihydro-6-oxo-3,4-diphenylpyridazin-1-yl)ethoxy ethyl ester; Acetic Acid, 5-cyano-1,6-dihydro-6-oxo-3,4-diphenyl-pyridazin-yl-methoxy ethyl ester; Acetic Acid, 5-cyano-1,6-dihydro-6-oxo-3,4-diphenylpyridazin-yl-2-propenyl ester; Acetic Acid, 5-cyano-1,6-dihydro-6-oxo-3,4-diphenylpyridazin-1-yl-3-methoxy-1-butyl ester; 1-Pyridazineacetylchloride, 5-cyano-1,6-dihydro-6-oxo-3,4-diphenyl; Acetic Acid, 5-cyano-1,6-dihydro-6-oxo-3,4-diphenylpyridazin-1-yl-1-pentyl ester; Acetic Acid, 5-cyano-1,6-dihydro-6-oxo-3,4-diphenylpyridazin-1-yl-2-methyl-2-propenyl ester; Acetic Acid, 5-cyano-1,6-dihydro-6-oxo-3,4-diphenylpyridazin-1-yl-1-butyl ester; Acetic Acid, 5-cyano-1,6-dihydro-6-oxo-3,4-diphenylpyridazin-1-yl-2-ethyl-butyl ester; Acetic Acid, 5-cyano-1,6-dihydro-6-oxo-3,4-diphenylpyridazin-1-yl cyclohexyl ester; Acetic Acid, 5-cyano-1,6-dihydro-6-oxo-3,4-diphenylpyridazin-1-yl-3-methyl-3-butenyl ester; Acetic Acid, 5-cyano-1,6-dihydro-6-oxo-3,4-diphenylpyridazin-1-yl diethanol amine salt; Propionic Acid, 3-(5-cyano-1,6-dihydro-6-oxo-3,4-diphenyl-pyridazin-1-yl)potassium salt; Ethanol, 2-(5-cyano-1,6-dihydro-6-oxo-3,4-diphenylpyridazin-1-yl)phenylether; Acetic Acid, 5-cyano-1,6-dihydro-6-oxo-3,4-diphenyl-pyridazin-1-yl-2-propynyl ester; and Acetic Acid, 5-cyano-1,6-dihydro-6-oxo-3,4-diphenylpyridazin-1-yl-1-hexadecyl ester.

2. The composition of claim 1 wherein said herbicidally effective amount ranges from about 0.06 kg/hectare to 4.00 kg/hectare.

3. A method for controlling undesirable plants by applying to the situs thereof a herbicidally effective amount of at least one active compound having the basic formula:

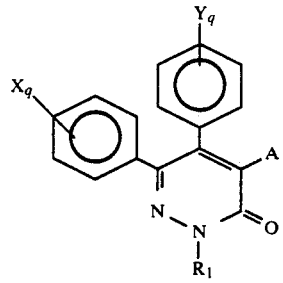

or the salts and water hydrates thereof wherein said active compound is selected from the group consisting of Ethanol, 2-(5-cyano-1,6-dihydro-6-oxo-3,4-diphenyl-pyridazin-1-yl); Acetic Acid, 5-cyano-1,6-dihydro-6-oxo-3,4-diphenylpyridazin-1-yl; Acetic Acid, 5-cyano-1,6-dihydro-6-oxo-3,4-diphenylpyridazin-1-yl ethyl ester; Propionic Acid, 3-(5-cyano-1,6-dihydro-6-oxo-3,4-diphenylpyridazin-1-yl); Propionic Acid, 3-(5-cyano-1,6-dihydro-6-oxo-3,4-diphenylpyridazin-1-yl)-ethyl ester; Propionic Acid, 3-(5-cyano-1,6-dihydro-6-oxo-3,4-diphenylpyridazin-1-yl)ethoxy ethyl ester; Acetic Acid, 5-cyano-1,6-dihydro-6-oxo-3,4-diphenylpyridazin-1-yl-methoxy ethyl ester; Acetic Acid, 5-cyano-1,6-dihydro-6-oxo-3,4-diphenylpyridazin-1-yl-2-propenyl ester; Acetic Acid, 5-cyano-1,6-dihydro-6-oxo-3,4- diphenylpyridazin-1-yl-3-methoxy-1-butyl ester; 1-Pyridazineacetylchloride, 5-cyano-1,6-dihydro-6-oxo-3,4,-diphenyl; Acetic Acid, 5-cyano-1,6-dihydro-6-oxo-3,4-diphenylpyridazin-1-yl-1-pentyl ester; Acetic Acid, 5-cyano-1,6-dihydro-6-oxo-3,4-diphenylpyridazin-1-yl-2-methyl-2-propenyl ester; Acetic Acid, 5-cyano-1,6-dihydro-6-oxo-3,4,-diphenylpyridazin-1-yl-1-butyl ester; Acetic Acid, 5-cyano-1,6-dihydro-6-oxo-3,4-diphenylpyridazin-1-yl-2-ethyl-1-butyl ester; Acetic Acid, 5-cyano-1,6-dihydro-6-oxo-3,4-diphenylpyridazin-1-yl cyclohexyl ester; Acetic Acid, 5-cyano-1,6-dihydro-6-oxo-3,4,-diphenlypyridazin-1-yl-3-methly-3-butenyl ester; Acetic Acid, 5-cyano-1,6-dihydro-6-oxo-3,4-diphneylpyridazin-1-yl-diethanol amine salt; Propionic Acid, 3-(5-cyano-1,6-dihydro-6-oxo-3,4-diphenylpyridazin-1-yl)potassium salt; Ethanol, 2-(5-cyano-1,6-dihydro-6-oxo-3,4-diphenylpyridazin-1-yl)phenylether; Acetic Acid, 5-cyano-1,6-dihydro-6-oxo-3,4-diphenylpyridazin-1-yl-2-propynyl ester; and Acetic Acid, 5-cyano-1,6-dihydro-6-oxo-3,4,-diphenylpyridazin-1-yl-1-hexadecyl ester.

4. The method of claim 3 wherein application is by soil drench and the amount of said active compound applied ranges from about 0.06 kg/hectare to about 4.00 kg/hectare.

5. A plant growth regulant composition comprising an effective plant growth regulant amount of at least one active compound of the formula:

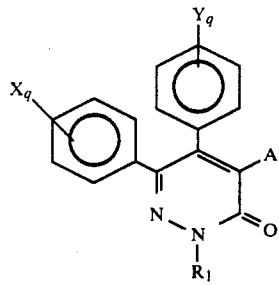

or the salts and water hydrates thereof wherein said active compound is selected from the group consisting of Acetic Acid, 5-cyano-1,6-dihydro-6-oxo-3,4-diphenylpyridazin-1-yl; Acetic Acid, 5-cyano-1,6-dihydro-6-oxo-3,4-diphenylpyridazin-1-yl ethyl ester; Propionic Acid, 3-(5-cyano-1,6-dihydro-6-oxo-3,4-diphenylpyridazin-1-yl); Propionic Acid, 3-(5-cyano-1,6-dihydro-6-oxo-3,4-diphenylpyridazin-1-yl)ethyl ester; Propionic Acid, 3-(5-cyano-1,6-dihydro-6-oxo-3,4-diphenylpyridazin-1-yl)-1-propyl ester; Propionic Acid, 3-(5-cyano-1,6-dihydro-6-oxo-3,4-diphenylpyridazin-1-yl)diethanol amine salt; Acetic Acid, 5-cyano-1,6-dihydro-6-oxo-3,4-diphenylpyridazin-1-yl diethanol amine salt; Propionic Acid, 3-(5-cyano-1,6-dihydro-6-oxo-3,4-diphenylpyridazin-1-yl)methoxy ethyl ester; Propionic Acid, 3-(5-cyano-1,6-dihydro-6-oxo-3,4-diphenylpyridazin-1-yl)sodium salt; Acetic Acid, 5-cyano-1,6-dihydro-6-oxo-3,4-diphenylpyridazin-1-yl sodium salt; Propionic Acid, 3-(5-cyano-1,6-dihydro-6-oxo-3,4-diphenylpyridazin-1-yl)potassium salt; Acetic Acid, 5-cyano-1,6-dihydro-6-oxo-3,4-diphenylpyridazin-1-yl potassium salt; Propionic Acid, 3-(5-cyano-1,6-dihydro-6-oxo-3,4-diparafluorophenylpyridazon-1-yl)ethyl ester; Acetic Acid, 5-cyano-1,6-dihydro-6-oxo-3,4-diphenylpyridazin-1-yl methyl ester; Acetic Acid, 5-cyano-1,6-dihydro-6-oxo-3,4-diphenylpyridazin-1-yl isobutyl ester; Acetic Acid, 5-cyano-1,6-dihydro-6-oxo-3,4-diphenylpyridazin-1-yl n-propyl ester; Acetic Acid, 5-cyano-1,6-dihydro-6-oxo-3,4-diphenylpyridazin-1-yl methoxy ethyl ester; Acetic Acid, 5-cyano-1,6-dihydro-6-oxo-3,4-diphenylpyridazin-1-yl-2-propenyl ester; Acetic Acid, 5-cyano-1,6-dihydro-6-oxo-3,4-diphenylpyridazin-1-yl-3-methoxy-1-butyl ester; Acetic acid, 5-cyano-1,6-dihydro-6-oxo-3,4-diphenylpyridazin-1-yl-methoxymethyleneoxy ethyl ester; Acetic Acid, 5-cyano-1,6-dihydro-6-oxo-3,4-diphenylpyridazin-1-yl-1-pentyl ester; Acetic Acid, 5-cyano-1,6-dihydro-6-oxo-3,4-diphenylpyridazin-1-yl-1-butyl ester; Acetic Acid, 5-cyano-1,6-dihydro-6-oxo-3,4-diphenylpyridazin-1-yl-1-hexadecyl ester; Acetic Acid, 5-cyano-1,6-dihydro-6-oxo-3,4-diphenylpyridazin-1-yl-hexyl ester; Acetic Acid, 5-cyano-1,6-dihydro-6-oxo-3,4-diphenylpyridazin-1-yl-4-chloro-1-butyl ester; Acetic Acid, 5-cyano-1,6-dihydro-6-oxo-3,4-diphenylpyridazin-1-yl-ethoxy ethyl ester; and Acetic Acid, 5-cyano-1,6-hydro-6-oxo-3,4-diphenylpyridazin-1-yl-phenoxy ethyl ester.

6. A plant growth regulant composition comprising an effective plant growth regulant amount of at least one active compound of the formula:

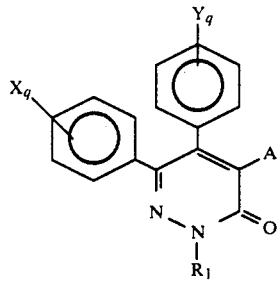

or the salts and the water hydrates thereof wherein said active compound is selected from the group consisting of Acetic Acid, 5-cyano-1,6-dihydro-6-oxo-3,4-diphenylpyridazin-1-yl ethyl ester; Propionic Acid, 3-(5-cyano-1,6-dihydro-6-oxo-3,4-diparafluorophenyl-pyridazin-1-yl)ethyl ester; Acetic Acid, 5-cyano-1,6-dihydro-6-oxo-3,4-diphenylpyridazin-1-yl metyl ester; Acetic Acid, 5-cyano-1,6-dihydro-6-oxo-3,4-diphenylpyridazin-1-yl-isobutyl ester; Acetic Acid, 5-cyano-1,6-dihydro-6-oxo-3,4-diphenylpyridazin-1-yl n-propyl ester; Acetic Acid, 5-cyano-1,6-dihydro-6-oxo-3,4-diphenylpyridazin-1-yl-methoxy ethyl ester; Acetic Acid, 5-cyano-1,6-dihydro-6-oxo-3,4-diphenylpyridazin-1-yl-2-propenyl ester; Acetic Acid, 5-cyano-1,6-dihydro-6-oxo-3,4-diphenylpyridazin-1-yl-3-methoxy-1-butyl ester; Acetic Acid, 5-cyano-1,6-dihydro-6-oxo-3,4-diphenylpyridazin-1-yl-methoxymethylneneoxy ethyl ester; Acetic Acid, 5-cyano-1,6-dihydro-6-oxo-3,4-diphenylpyridazin-1-yl-1-pentyl ester; Acetic Acid, 5-cyano-1,6-dihydro-6-oxo-3,4-diphenylpyridazin-1-yl-1-butyl ester; Acetic Acid, 5-cyano-1,6-dihydro-6-oxo-3,4-diphenylpyridazin-1-yl-1-hexadecyl ester; Acetic Acid, 5-cyano-1,6-dihydro-6-oxo-3,4-diphenylpyridazin-1-yl-1-hexyl ester; Acetic Acid, 5-cyano-1,6-dihydro-6-oxo-3,4-diphenylpyridazin-1-yl-4-chloro-1-butyl ester; Acetic Acid, 5-cyano-1,6-dihydro-6-oxo-3,4-diphenylpyridazin-1-yl-ethoxy ethyl ester; and Acetic Acid, 5-cyano-1,6-dihydro-6-oxo-3,4-diphenylpyridazin-1-yl-phenoxy ethyl ester.

7. The composition of claim 4 wherein said active compound is Acetic Acid, 5-cyano-1,6-dihydro-6-oxo-3,4-diphenylpyridazin-1-yl ethyl ester.

8. The composition of claims 3, 4, 5 or 6 wherein said plant growth regulant amount ranges from about 0.01 kg/hectare to about 2.00 kg/hectare.

* * * * *